(12) United States Patent
Nickolaus

(10) Patent No.: US 8,877,758 B2
(45) Date of Patent: Nov. 4, 2014

(54) COMBINATIONS OF MEDICAMENTS, CONTAINING PDE4-INHIBITORS AND EP4-RECEPTOR-ANTAGONISTS

(75) Inventor: Peter Nickolaus, Warthausen (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

(21) Appl. No.: 13/639,626

(22) PCT Filed: Apr. 1, 2011

(86) PCT No.: PCT/EP2011/055072
§ 371 (c)(1),
(2), (4) Date: Nov. 26, 2012

(87) PCT Pub. No.: WO2011/124524
PCT Pub. Date: Oct. 13, 2011

(65) Prior Publication Data
US 2013/0237527 A1 Sep. 12, 2013

(30) Foreign Application Priority Data
Apr. 8, 2010 (EP) .................................... 10159382

(51) Int. Cl.
| | |
|---|---|
| A61K 31/497 | (2006.01) |
| A61K 31/519 | (2006.01) |
| A61K 31/44 | (2006.01) |
| A61K 31/40 | (2006.01) |
| A61K 31/437 | (2006.01) |
| C07D 495/04 | (2006.01) |
| A61K 45/06 | (2006.01) |
| A61K 31/498 | (2006.01) |
| A61K 31/4745 | (2006.01) |
| A61K 31/55 | (2006.01) |

(52) U.S. Cl.
CPC ............. *A61K 31/519* (2013.01); *A61K 31/437* (2013.01); *A61K 31/44* (2013.01); *C07D 495/04* (2013.01); *A61K 45/06* (2013.01); *A61K 31/498* (2013.01); *A61K 31/4745* (2013.01); *A61K 31/55* (2013.01)
USPC .................... 514/252.16; 514/260.1; 514/292; 514/411

(58) Field of Classification Search
USPC .......................... 514/252.16, 260.1, 292, 411
See application file for complete search history.

(56) References Cited

U.S. PATENT DOCUMENTS

| | | |
|---|---|---|
| 2004/0142969 A1 | 7/2004 | Elworthy |
| 2004/0254233 A1 | 12/2004 | Araldi et al. |
| 2010/0305102 A1 | 12/2010 | Pouzet et al. |
| 2011/0021501 A1 | 1/2011 | Pouzet et al. |
| 2013/0225609 A1 | 8/2013 | Nickolaus |

FOREIGN PATENT DOCUMENTS

| | | | |
|---|---|---|---|
| GB | 2330307 A | * | 4/1999 |
| WO | WO 0164647 A1 | * | 9/2001 |
| WO | 02092097 A1 | | 11/2002 |
| WO | 2006122403 A1 | | 11/2006 |
| WO | 2009050242 A2 | | 4/2009 |
| WO | 2009050248 A1 | | 4/2009 |
| WO | 2011124525 A1 | | 10/2011 |

OTHER PUBLICATIONS

Hertz, Angie, L., et al; Elevated Cyclic AMP and PDE4 Inhibition Induce Chemokine Expression in Human Monocyte-Derived Macrophages; PNAS (2009) vol. 106, No. 51 pp. 21978-21983.
International Search Report for PCT/EP2011/055072 mailed Jul. 19, 2011.
Rehal, Sonia, et al; Characterization of Biosynthesis and Modes of Action of Prostaglandin E2 and prostacyclin in guinea pig mesenteric lymphatic vessels; British Journal of Pharmacology (2009) vol. 158, No. 8 pp. 1961-1970.
Sastre, B. et al; Prostaglandin E2 May Decrease Airway Inflamation and Muscular Hyperplasia in Eosinophilic Bronchitis Patients Through Prostanoid Receptors EP2 and EP4; Allergy (2009) vol. 64, No. 90 pp. 135-136.

(Continued)

*Primary Examiner* — Kevin E Weddington
(74) *Attorney, Agent, or Firm* — Michael P. Morris; Timothy X. Witkowski

(57) ABSTRACT

The present invention relates to new medicament combinations which contain in addition to one or more PDE4-inhibitors (1) at least one EP4 receptor antagonist (2), as well as the use thereof for the treatment of preferably respiratory complaints such as particularly COPD, chronic sinusitis and asthma.

The invention relates in particular to those medicament combinations which contain at least one EP4 receptor antagonist (2), in addition to one or more, preferably one, PDE4 inhibitor of general formula 1

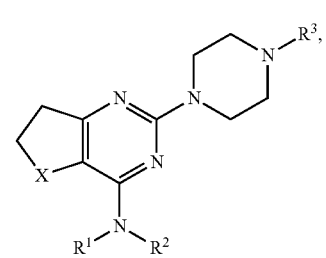

wherein X is SO or $SO_2$, but preferably SO, and wherein $R^3$ denotes an optionally substituted, mono- or bicyclic, unsaturated, partly saturated or saturated heterocyclic group or an optionally substituted, mono- or bicyclic heteroaryl
and wherein $R^1$ and $R^2$ have the meanings given in claim 1, the preparation thereof and the use thereof for the treatment of respiratory complaints.

20 Claims, 8 Drawing Sheets

(56) References Cited

OTHER PUBLICATIONS

Clark, "MF498(N-(($-(5-9-Diethoxy-6-oxo-6,8-dihydro-7H-pyrrolo(3,4-g)guinolin-7-yl)-3-methylbenzyl)sulfonyl)-2-(2-methoxyphenyl) acetamide Selective E Prostanoid Receptor 4 Antagonist", Journal of Pharmacology and Experimental Therapeutics, 2008, vol. 325, No. 2, p. 424-434.

Sugimoto, Prostaglandin E Receptors, Journal of Biological Chemistry, 2001, vol. 282, No. 16, p. 11613-11617.

Aoki, "A novel Phosphiedeterase Type 4 Inhibitor", Journal of Pharmacology and Experimental Therapeutics, 2000, vol. 295, No. 1, p. 255-260.

International Search Report for PCT/EP2011/055074 mailed Jul. 20, 2011.

Buckley, Thorax, "EP4 receptor as a new target for bronchodilator therapy", vol. 66, No. 12, 2011, p. 1029-1035.

Benyahia, "PGE3 receptor agonsists: Potent Dilators of human bronchi and future asthma therapy?", Pulmonary Pharmacology and Therapeutics, vol. 25, No. 11, 2012.

Okumura, "Effects of the Selective EP4 Antagonist CJ-023,423 o chronic Inflammation and bone destruction in rat adjuvant-induced arthritis", Journal of Pharmacy and Pharmacology, vol. 60, No. 6, 2008, p. 723-730.

Xinrong, "Prostaglandin E receptor EP4 antagonism inhibits breast cancer metastasis", Cancer Research, American Association for Cancer Research, vol. 66, 2006, p. 2923-2927.

* cited by examiner

COMBINATIONS OF MEDICAMENTS, CONTAINING PDE4-INHIBITORS AND EP4-RECEPTOR-ANTAGONISTS

The present invention relates to new medicament combinations which contain in addition to one or more PDE4-inhibitors (1) at least one EP4 receptor antagonist (2), processes for preparing them and their use for the treatment of in particular respiratory complaints such as for example COPD, chronic sinusitis and asthma.

The invention relates in particular to those medicament combinations which comprise, in addition to one or more, preferably one, PDE4-inhibitor of general formula 1

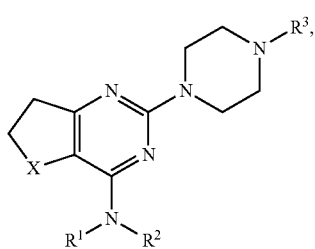

wherein X denotes SO or $SO_2$, but preferably SO, and wherein
$R^3$ denotes an optionally substituted, mono- or bicyclic, unsaturated, partly saturated or saturated heterocyclic group or an optionally substituted, mono- or bicyclic heteroaryl
and wherein $R^1$ and $R^2$ have the meanings given in claim 1, at least one EP4 receptor antagonist (2), the preparation thereof and the use thereof for the treatment of respiratory complaints.

PRIOR ART

WO2009050242 discloses heterocyclic group-substituted piperazino dihydrothienopyrimidines of formula 1 as PDE4-inhibitors, the preparation thereof as well as the use thereof for the treatment of respiratory complaints.

It is also known that many "1st generation" PDE4-inhibitors such as for example rolipram lead to undesirable side effects. Consequently, it was an objective of the present invention to provide a medicament or a medicament combination containing a PDE4 inhibitor which has a low side-effect profile. Surprisingly it has been found that an EP4 receptor antagonist that is administered simultaneously with a PDE4 inhibitor or a few hours (at most 6 hours) before or after a PDE4 inhibitor, greatly reduces the typical side effects of a PDE4 inhibitor, without having any appreciable side effects in long-term therapy.

EP4-receptor-antagonists such as for example [N-{[4-(5,9-diethoxy-6-oxo-6,8-dihydro-7H-pyrrolo[3,4-g]quinolin-7-yl)-3-methylbenzyl]sulphonyl}-2-(2-methoxyphenyl)acetamide] (also known as MF498) were indeed already known for example from Clark et al; The Journal of Pharmacology and Experimental Therapeutics; Vol. 325, No. 2; pages 425-434, but it was not known that typical PDE4-mediated side effects are significantly reduced by EP4-receptor-antagonists of this kind.

The present invention therefore relates to a novel medicament combination which includes at least one EP4 receptor antagonist (2) in addition to one or more PDE4-inhibitors (1). The present invention preferably relates to those medicament combinations which contain in addition to one or more PDE4-inhibitors (1) at least one EP4 receptor antagonist (2) and wherein at least one EP4-receptor-antagonist (2) is an EP4-specific antagonist.

A preferred embodiment of the present invention relates to one of the above mentioned medicament combinations, wherein the at least one EP4 receptor antagonist is selected from among
[N-{[4-(5,9-diethoxy-6-oxo-6,8-dihydro-7H-pyrrolo[3,4-g]quinolin-7-yl)-3-methylbenzyl]sulphonyl}-2-(2-methoxyphenyl)acetamide](2.1);
5-butyl-2,4-dihydro-4-[[2'-[N-(3-methyl-2-thiophene-carbonyl)sulphamoyl]biphenyl-4-yl]methyl]-2-[(2-trifluoromethyl)phenyl]-1,2,4-triazol-3-one (2.2);
(4-{(1S)-1-[({5-chloro-2-[(4-fluorophenyl)oxy]phenyl}carbonyl)amino]ethyl}benzoic acid (2.3);
N-[({2-[4-(2-ethyl-4,6-dimethyl-1H-imidazo[4,5-c]pyridin-1-yl)phenyl]ethyl}amino)carbonyl]-4-methylbenzene sulphonamide (2.4);
4-[[4-(5-methoxy-2-pyridinyl)phenoxy]methyl]-5-methyl-N-[(2-methylphenyl)sulphonyl]-2-furancarboxamide (2.5);
methyl 11alpha,15alpha-dihydroxy-16-(3-methoxymethylphenyl)-9-oxo-17,18,19,20-tetranor-5-thia-13(E) prostanoate (2.6);
4-cyano-2-[[2-(4-fluoro-1-naphthalenyl)-1-oxopropyl]amino]-benzenebutanoic acid (2.7) and
N-{2-[4-(4,9-diethoxy-1-oxo-1,3-dihydro-2H-benzo[f]isoindol-2-yl)phenyl]acetyl}benzene sulphonamide (2.8).

A particularly preferred embodiment of the present invention relates to one of the above mentioned medicament combinations, which comprises at least one EP4 receptor antagonist (2), in addition to one or more, preferably one, PDE4 inhibitor (1) of general formula 1

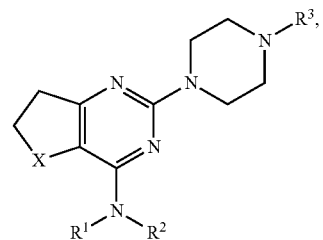

wherein
X denotes SO or $SO_2$,
$R^1$ denotes H, $C_{1-6}$-alkyl,
$R^2$ is H or a group selected from among $C_{1-10}$-alkyl and $C_{2-6}$-alkenyl, which may optionally be substituted by one or more groups selected from halogen and $C_{1-3}$-fluoroalkyl or which is optionally substituted by one or more groups selected from among $OR^{2.1}$, $COOR^{2.1}$, $CONR^{2.2}R^{2.3}$, $SR^{2.1}$, $SO-R^{2.1}$, $SO_2-R^{2.1}$, $C_{6-10}$-aryl, a het, a hetaryl, a mono- or bicyclic $C_{3-10}$-cycloalkyl, $CH_2-NR^{2.2}R^{2.3}$ and $NR^{2.2}R^{2.3}$, which in turn may optionally be substituted by one or more groups selected from among OH, halogen, $OR^{2.1}$, oxo, $CF_3$, $CHF_2$, $CH_2F$, $C_{1-6}$-alkyl, $C_{1-6}$-alkanol, $C_{6-10}$-aryl, $COOR^{2.1}$, $CH_2-NR^{2.2}R^{2.3}$ and $NR^{2.2}R^{2.3}$,
wherein $R^{2.1}$ is H or a group selected from among $C_{1-6}$-alkyl, $C_{1-6}$-alkanol, $C_{1-3}$-haloalkyl, mono- or bicyclic $C_{3-10}$-cycloalkyl, $C_{6-10}$-aryl-$C_{1-6}$-alkylene, mono- or bicyclic hetaryl-$C_{1-6}$-alkylene, het-$C_{1-6}$-alkylene, $C_{3-10}$-cycloalkyl-$C_{1-6}$-alkylene, a mono- or bicyclic $C_{6-10}$-aryl, a hetaryl and a het, which may optionally be substituted by one or more groups selected from among OH, O—($C_{1-3}$-alkyl), halogen, $C_{1-6}$-alkyl and $C_{6-10}$-aryl,
wherein $R^{2.2}$ and $R^{2.3}$ independently of one another denote H or a group selected from among $C_{1-6}$-alkyl, mono- or bicyclic $C_{3-10}$ cycloalkyl, $C_{6-10}$-aryl-$C_{1-6}$-alkylene, hetaryl-$C_{1-6}$-alkylene, mono- or bicyclic $C_{6-10}$-aryl, het, hetaryl, CO—$NH_2$, CO—$NHCH_3$, CO—$N(CH_3)_2$, $SO_2$—($C_1$-$C_2$-alkyl), CO—$R^{2.1}$ and $COOR^{2.1}$, which may optionally be substituted by one or more groups selected from among OH, halogen, $C_{1-6}$-alkyl, $C_{6-10}$-aryl and $COOR^{2.1}$, wherein het is a three- to eleven-membered, mono- or bicyclic, saturated or partly saturated, optionally annellated or optionally bridged heterocyclic group, which contains 1, 2, 3 or 4 heteroatoms selected independently of one another from among N, S or O, and wherein hetaryl is a five- to eleven-membered, mono- or bicyclic, optionally annellated heteroaryl, which contains 1, 2, 3 or 4 heteroatoms selected independently of one another from among N, S or O, and wherein cycloalkyl may be saturated or partly saturated, or $R^2$ denotes a mono- or polycyclic $C_{3-10}$ cycloalkyl, which may optionally be singly or multiply bridged by $C_{1-3}$-alkyl groups and which may optionally be substituted by a group selected from among branched or unbranched $C_{1-6}$-alkanol, $C_{1-3}$-fluoroalkyl, $C_{1-3}$-alkylene-$OR^{2.1}$, $OR^{2.1}$, $COOR^{2.1}$, $SO_2$—$NR^{2.2}R^{2.3}$, het, $C_{6-10}$-aryl, $C_{1-6}$-alkyl, $C_{6-10}$-aryl-$C_{1-6}$-alkylene, hetaryl-$C_{1-6}$-alkylene, mono- or bicyclic $C_{3-10}$ cycloalkyl and $NR^{2.2}R^{2.3}$, which may optionally be substituted by one or more groups selected from among OH, $OR^{2.1}$, oxo, halogen, $CF_3$, $CHF_2$, $CH_2F$, $C_{1-6}$-alkyl, $C_{6-10}$-aryl and $NR^{2.2}R^{2.3}$, or $R^2$ denotes a mono- or polycyclic $C_{6-10}$-aryl, which may optionally be substituted by OH, SH or halogen or by one or more groups selected from among $OR^{2.1}$, $COOR^{2.1}$, $NR^{2.2}R^{2.3}$, $CH_2$—$NR^{2.2}R^{2.3}$, $C_{3-10}$-cycloalkyl, het, —$C_{1-6}$-alkyl, $C_{1-3}$-fluoroalkyl, $C_{6-10}$-aryl-$C_{1-6}$-alkylene, het-$C_{1-6}$-alkylene, hetaryl-$C_{1-6}$-alkylene, $C_{6-10}$-aryl, $SO_2$—$CH_3$, $SO_2$—$CH_2CH_3$ and $SO_2$—$NR^{2.2}R^{2.3}$, which in turn may optionally be substituted by one or more or several groups selected from among OH, $OR^{2.1}$, $CF_3$, $CHF_2$, $CH_2F$, oxo, halogen, $CF_3$, $CHF_2$, $CH_2F$, $C_{1-6}$-alkyl, $C_{6-10}$-aryl and $NR^{2.2}R^{2.3}$, or $R^2$ denotes a group selected from among het and hetaryl, which may optionally be substituted by one or more groups selected from among halogen, OH, oxo, $CF_3$, $CHF_2$ and $CH_2F$ or by one or more groups selected from among $OR^{2.1}$, $C_{1-3}$-alkylene-$OR^{2.1}$, $SR^{2.1}$, SO—$R^{2.1}$ and $SO_2$—$R^{2.1}$, $COOR^{2.1}$, $COR^{2.1}$, $C_{1-6}$-alkanol, $C_{3-10}$-cycloalkyl, $C_{6-10}$-aryl, $C_{1-6}$-alkyl, $C_{6-10}$-aryl-$C_{1-6}$-alkylene, hetaryl-$C_{1-6}$-alkylene, het, hetaryl, $C_{1-3}$-alkylene-$OR^{2.1}$ and $NR^{2.2}R^{2.3}$, which in turn may optionally be substituted by one or more groups selected from among OH, $OR^{2.1}$, oxo, halogen, $CF_3$, $CHF_2$, $CH_2F$, $C_{1-6}$-alkyl, $C_{6-10}$-aryl and $NR^{2.2}R^{2.3}$, or wherein $NR^1R^2$ together denotes a heterocyclic four- to seven-membered ring which may optionally be bridged, which contains 1, 2 or 3 heteroatoms selected from among N, O and S and which may optionally be substituted by one or more groups selected from among OH, $OR^{2.1}$, $C_{1-3}$-alkylene-$O^{R.1}$, oxo, halogen, $C_{1-6}$-alkyl, $C_{6-10}$-aryl, $COOR^{2.1}$, $CH_2$—$NR^{2.2}$—COO—$R^{2.1}$, $CH_2$—$NR^{2.2}$—CO—$R^{2.1}$, $CH_2$—$NR^{2.2}$—CO—$CH_2$—$NR^{2.2}R^{2.3}$, $CH_2$—$NR^{2.2}$—$SO_2$—$C_{1-3}$-alkyl, $CH_2$—$NR^{2.2}$—$SO_2$—$NR^{2.2}R^{2.3}$, $CH_2$—$NR^{2.2}$—CO—$NR^{2.2}R^{2.3}$, CO—$NR^{2.2}R^{2.3}$, $CH_2$—$NR^{2.2}R^{2.3}$ and $NR^{2.2}R^{2.3}$, and wherein $R^3$ is a group selected from among a het and a hetaryl, which may optionally be substituted by one or more groups selected from among halogen, $C_{1-3}$-fluoroalkyl, CN, OH, oxo, —$C_{1-6}$-alkyl, —O—$R^{2.1}$, —$COOR^{2.1}$, SO—$R^{2.1}$, $SO_2$—$R^{2.1}$, $C_{6-10}$-aryl, $C_{1-3}$-alkylene-$C_{6-10}$-aryl, —$C_{1-3}$-alkylene-$NR^{2.2}R^{2.3}$, —$NR^{2.2}R^{2.3}$, a $C_{3-10}$-cycloalkyl, a $C_{1-3}$-alkylene-$C_{3-10}$-cycloalkyl, a het, a hetaryl, $C_{1-3}$-alkylene-hetaryl, and $C_{1-3}$-alkylene-het, which in turn may optionally be substituted by one or more groups selected from among OH, halogen, —$C_{1-3}$-fluoroalkyl, $C_{1-6}$-alkyl, $C_{6-10}$-aryl, —$COO(C_{1-3}$-alkyl) and O—($C_{1-3}$-alkyl).

Also preferred are medicament combinations which comprise at least one EP4 receptor antagonist (2), in addition to one or more, preferably one, PDE4 inhibitor of general formula 1, wherein X is SO, $R^1$ is H $R^2$ is H or $C_{1-6}$-alkyl, which may optionally be substituted by one or more groups selected from F, $CF_3$, $CHF_2$ or $CH_2F$ or which may optionally be substituted by one or more groups selected from among $OR^{2.1}$, $COOR^{2.1}$, $CONR^{2.2}R^{2.3}$, $SR^{2.1}$, SO—$R^{2.1}$, $SO_2$—$R^{2.1}$, phenyl, a het, a hetaryl, a monocyclic $C_{3-7}$-cycloalkyl, $CH_2$—$NR^{2.2}R^{2.3}$ and $NR^{2.2}R^{2.3}$, which in turn may optionally be substituted by one or more groups selected from among OH, F, Cl, Br, $CF_3$, $CHF_2$, $CH_2F$, $OR^{2.1}$, oxo, methyl, ethyl, propyl, isopropyl, $C_{1-2}$-alkanol, phenyl, $COOR^{2.1}$, $CH_2$—$NR^{2.2}R^{2.3}$ and $NR^{2.2}R^{2.3}$, wherein $R^{2.1}$ is H or a group selected from among methyl, ethyl, propyl, isopropyl, monocyclic $C_{3-7}$ cycloalkyl, phenyl-$C_{1-2}$-alkylene, hetaryl-$C_{1-2}$-alkylene, het-$C_{1-2}$-alkylene, $C_{3-7}$-cycloalkyl-$C_{1-2}$-alkylene, phenyl, a hetaryl and a het, which may optionally be substituted by one or more groups selected from among OH, halogen, methyl, ethyl, propyl, isopropyl, O-methyl, O-ethyl, O-propyl, O-isopropyl and phenyl, wherein $R^{2.2}$ and $R^{2.3}$ independently of one another denote H or a group selected from among methyl, ethyl, propyl, isopropyl, monocyclic $C_{3-7}$-cycloalkyl, phenyl-$C_{1-3}$-alkylene, hetaryl-$C_{1-3}$-alkylene, phenyl, het, hetaryl, CO—$NH_2$, CO—$NHCH_3$, $CON(CH_3)_2$, $SO_2$—($C_1$-$C_2$-alkyl), CO—$R^{2.1}$ and $COOR^{2.1}$, which may optionally be substituted by one or more groups selected from among OH, F, Cl, Br, methyl, ethyl, propyl, isopropyl, phenyl and $COOR^{2.1}$, wherein het is a three- to seven-membered, monocyclic, saturated or partly saturated heterocyclic group which contains 1, 2 or 3 heteroatoms selected independently of one another from among N, S or O, and wherein hetaryl is a five- to six-membered, monocyclic, aromatic heteroaryl, which contains 1, 2 or 3 heteroatoms selected independently of one another from among N, S or O, and wherein cycloalkyl may be saturated or partly saturated, or $R^2$ denotes a monocyclic $C_{3-7}$ cycloalkyl, which may optionally be substituted by a group selected from among branched or unbranched $C_{1-2}$-alkanol, $C_{1-3}$-fluoroalkyl, $C_{1-3}$-alkylene-$OR^{2.1}$, $OR^{2.1}$, $COOR^{2.1}$, $SO_2$—$NR^{2.2}R^{2.3}$, het, methyl, ethyl, propyl, isopropyl, phenyl, phenyl-$C_{1-2}$-alkylene, hetaryl-$C_{1-2}$-alkylene, monocyclic $C_{3-7}$ cycloalkyl and $NR^{2.2}R^{2.3}$, which may optionally be substituted by one or more groups selected from among OH, $OR^{2.1}$, oxo, halogen, $CF_3$, $CHF_2$, $CH_2F$, methyl, ethyl, propyl, isopropyl, phenyl and $NR^{2.2}R^{2.3}$, or $R^2$ denotes a phenyl which may optionally be substituted by OH, SH, F, Cl or Br or by one or more groups selected from among $OR^{2.1}$, $COOR^{2.1}$, $NR^{2.2}R^{2.3}$, $CH_2$—$NR^{2.2}R^{2.3}$, $C_{3-7}$-cycloalkyl, het, methyl, ethyl, propyl, isopropyl, $CF_3$, $CHF_2$, $CH_2F$, phenyl-$C_{1-2}$-alkylene, het-$C_{1-2}$-alkylene, hetaryl-$C_{1-2}$-alkylene, phenyl, $SO_2$—$CH_3$, $SO_2$—$CH_2CH_3$ and $SO_2$—$NR^{2.2}R^{2.3}$, which in turn may optionally be substituted by one or more or several groups selected from among OH, $OR^{2.1}$, oxo, F, Cl, Br, $CF_3$, $CHF_2$, $CH_2F$, methyl, ethyl, propyl, isopropyl, phenyl and $NR^{2.2}R^{2.3}$, or $R^2$ denotes a group selected from among a het and a hetaryl, which may optionally be substituted by one or more groups selected from among F, Cl, Br, OH, oxo, $CF_3$, $CHF_2$, $CH_2F$ and SH or by one or more groups selected from among $OR^{2.1}$, $C_{1-3}$-alkylene-$OR^{2.1}$, $SR^{2.1}$, SO—$R^{2.1}$, $SO_2$—$R^{2.1}$, $COOR^{2.1}$, $COR^{2.1}$, $C_{1-2}$-alkanol, $C_{3-10}$-cycloalkyl, phenyl, methyl, ethyl, propyl, isopropyl, phenyl-$C_{1-2}$-alkylene, hetaryl-$C_{1-2}$-alkylene, het, hetaryl, $C_{1-2}$-alkanol and $NR^{2.2}R^{2.3}$, which may in turn optionally be substituted by one or more groups selected from among OH, $OR^{2.1}$, oxo, F, Cl, Br, $CF_3$, $CHF_2$, $CH_2F$, $C_{1-6}$-alkyl, phenyl and $NR^{2.2}R^{2.3}$, and wherein $R^3$ denotes a group selected from among a saturated or partly saturated, monocyclic three- to seven-membered heterocyclic group, a saturated or partly saturated, bicyclic five- to eleven-membered heterocyclic group, a monocyclic, five- to six-membered heteroaryl and a bicyclic, seven- to eleven-membered heteroaryl, which contains in each case 1, 2, 3 or 4 heteroatoms selected independently of one another from among N, O and S and which may optionally be substituted in each case by one or more groups selected from among halogen, $C_{1-3}$-fluoroalkyl, CN, OH, oxo, —$C_{1-6}$-alkyl, —O—$R^{2.1}$, —$COOR^{2.1}$, SO—$R^{2.1}$, $SO_2$—$R^{2.1}$, $C_{6-10}$-aryl, $C_{1-3}$-alkylene-$C_{6-10}$-aryl, —$C_{1-3}$-alkylene-$NR^{2.2}R^{2.3}$, —$NR^{2.2}R^{2.3}$, a $C_{3-10}$-cycloalkyl, a $C_{1-3}$-alkylene-$C_{3-10}$-cycloalkyl, het, a hetaryl, $C_{1-3}$-alkylene-hetaryl, and $C_{1-3}$-alkylene-het, which in turn may optionally be substituted by one or more groups selected from among OH, halogen, —$C_{1-3}$-fluoroalkyl, $C_{1-6}$-alkyl, $C_{6-10}$-aryl, —$COO(C_{1-3}$-alkyl) and O—($C_{1-3}$-alkyl).

In another particularly preferred aspect the invention relates to those of the above mentioned medicament combinations which contain at least one EP4 receptor antagonist (2), in addition to one or more, preferably one PDE4 inhibitor of general formula 1, wherein $R^2$ is a group according to formula 3

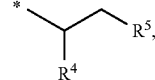

3 wherein $R^5$ is OH or $NH_2$ and wherein $R^4$ denotes a group selected from among $C_{1-4}$-alkyl, hetaryl and phenyl, which may optionally be substituted by one or more groups selected from among OH, F, Br, $OR^{2.1}$, oxo, methyl, ethyl, $C_{1-2}$-alkanol, phenyl, $COOR^{2.1}$, $CH_2$—$NR^{2.2}R^{2.3}$ and $NR^{2.2}R^{2.3}$.

In another particularly preferred embodiment the present invention relates to those of the above mentioned medicament combinations which comprise in addition to one or more, preferably one, PDE4 inhibitor of general formula 1, wherein $R^2$ is a group according to formula 3

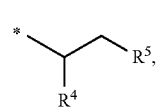

3 wherein $R^5$ is OH or $NH_2$ and wherein $R^4$ denotes methyl, ethyl, propyl or isopropyl, at least one EP4 receptor antagonist (2).

The present invention also preferably relates to those of the above medicament combinations which comprise in addition to one or more, preferably one, PDE4 inhibitor of general formula 1, wherein $R^2$ is a monocyclic three, four, five, six or seven-membered cycloalkyl ring which may optionally be substituted in the spiro position by a group selected from among —$CH_2$—$OR^{2.1}$, branched or unbranched $C_{2-6}$-alkylene-$OR^{2.1}$, methyl, ethyl, propyl, isopropyl, butyl, isobutyl, cyclopropyl, —$CF_3$, $CHF_2$, $CH_2F$ and $C_{2-4}$-fluoroalkyl, wherein $R^{2.1}$ is selected from among methyl, ethyl, propyl, isopropyl, butyl, isobutyl, at least one EP4 receptor antagonist (2).

In another particularly preferred embodiment the present invention relates to those of the above mentioned medicament combinations which comprise in addition to one or more, preferably one, PDE4 inhibitor of general formula 1, wherein $R^2$ is a phenyl which is optionally substituted in one or both meta positions by one or more groups selected from among methyl, ethyl, propyl, isopropyl, cyclopropyl, F, Cl, Br, OH, $OR^{2.1}$, $COOR^{2.1}$, $CF_3$, $CHF_2$, $CH_2F$, $NH_2$ and $N(CH_3)_2$, wherein $R^{2.1}$ may be H, methyl or ethyl, at least one EP4 receptor antagonist (2).

In another preferred aspect the present invention relates to those of the above mentioned medicament combinations which comprise, in addition to one or more, preferably one PDE4 inhibitor of general formula 1, wherein $R^2$ is a monocyclic, saturated three-, four-, five-, six- or seven-membered heterocyclic group with 1, 2 or 3 heteroatoms selected in each case from among N, O and S, which may optionally be substituted by one or more groups selected from among fluorine, chlorine, bromine, $CF_3$, $CHF_2$, $CH_2F$, OH, oxo and SH or by one or more groups selected from among $OR^{2.1}$, $C_{1-3}$-alkylene-$OR^{2.1}$, $SR^{2.1}$, SO—$R^{2.1}$, $SO_2$—$R^{2.1}$, $COOR^{2.1}$, $COR^{2.1}$, $C_{1-6}$-alkanol, $C_{3-10}$-cycloalkyl, phenyl, $C_{1-6}$-alkyl, phenyl-$C_{1-6}$-alkylene, hetaryl-$C_{1-6}$-alkylene, het, hetaryl and $NR^{2.2}R^{2.3}$, which in turn may optionally be substituted by one or more groups selected from among OH, $OR^{2.1}$, oxo, F, Cl, $CF_3$, $CHF_2$, $CH_2F$, $C_{1-6}$-alkyl, phenyl and $NR^{2.2}R^{2.3}$, at least one EP4 receptor antagonist (2).

Within the scope of the present invention one of the above medicament combinations which contains at least one EP4 receptor antagonist (2) in addition to one or more, preferably one PDE4 inhibitor of general formula 1, wherein $R^2$ is a monocyclic, saturated, six-membered heterocyclic group with a heteroatom selected from among N, O and S, which may optionally be substituted by one or more groups selected from among F, Cl, Br, $CF_3$, $CHF_2$, $CH_2F$, OH, oxo, $NH_2$, $NHCH_3$, $N(CH_3)_2$, methyl, ethyl, propyl, isopropyl, cyclopropyl, methoxy and ethoxy, is also particularly preferred.

In another particularly preferred aspect the invention relates to a medicament combination which contains at least one EP4 receptor antagonist (2) in addition to one or more, preferably one PDE4 inhibitor of general formula 1, wherein $R^2$ denotes a group selected from among piperidine or tetrahydropyran, which may optionally be substituted by one or more groups selected from among F, Cl, Br, OH, $CF_3$, $CHF_2$, $CH_2F$, $NH_2$, $NHCH_3$, $N(CH_3)_2$, oxo, methyl and methoxy.

Also particularly preferred is one of the above medicament combinations, which comprises at least one EP4 receptor antagonist (2) in addition to one or more, preferably one, PDE4 inhibitor of general formula 1, wherein $R^3$ is a monocyclic five- or six-membered heteroaryl ring which may optionally be substituted by one or more groups selected from among F, Cl, Br, $CF_3$, $CHF_2$, $CH_2F$, CN, OH, -methyl, ethyl, propyl, isopropyl, —O-methyl, O-ethyl, —COOmethyl, —COOethyl, $SO_2$—$(CH_3)$, SO—$(CH_3)$, $SO_2$—$(CH_2CH_3)$, SO—$(CH_2CH_3)$, phenyl, -methylene-phenyl, -ethylene-phenyl, —$NH_2$, —$NH(CH_3)$, $N(CH_3)_2$, -methylene-$NH_2$, -methylene-$NH(CH_3)$, -methylene-N$(CH_3)_2$, a $C_{3-6}$-cycloalkyl, a methylene-$C_{3-6}$-cycloalkyl, a saturated or partly saturated, five- to six-membered heterocyclic group, a five- or six-membered heteroaryl, -methylene-hetaryl, and -methylene-het, which in turn may optionally be substituted by one or more groups selected from among OH, F, Cl, Br, $CF_3$, $CHF_2$, $CH_2F$, methyl, ethyl, propyl, isopropyl, phenyl, —COO($CH_3$), —O-methyl and —O-ethyl.

In another particularly preferred aspect the invention relates to one of the above mentioned medicament combinations, which comprises at least one EP4 receptor antagonist (2), in addition to one or more, preferably one, PDE4 inhibitor of general formula 1, wherein $R^3$ is a bicyclic 9- to 11-membered saturated, unsaturated or partly saturated heterocyclic group, which may optionally be substituted by one or more groups selected from among F, Cl, Br, $CF_3$, $CHF_2$, $CH_2F$, CN, OH, -methyl, ethyl, propyl, isopropyl, —O-methyl, O-ethyl, —COOmethyl, —COOethyl, $SO_2$—$(CH_3)$, SO—$(CH_3)$, $SO_2$—$(CH_2CH_3)$, SO—$(CH_2CH_3)$, phenyl, -methylene-phenyl, -ethylene-phenyl, —$NH_2$, —$NH(CH_3)$, $N(CH_3)_2$, -methylene-$NH_2$, -methylene-$NH(CH_3)$, -methylene-N$(CH_3)_2$, a —$C_{3-6}$-cycloalkyl, a -methylene-$C_{3-6}$-cycloalkyl, a saturated, partly saturated or unsaturated 5- to 6-membered heterocyclic group, a 5- to 6-membered heteroaryl, -methylene-hetaryl, and -methylene-het, which in turn may optionally be substituted by one or more groups selected from among OH, F, Cl, Br, $CF_3$, $CHF_2$, $CH_2F$, methyl, ethyl, propyl, isopropyl, phenyl, —COO($CH_3$), —O-methyl and —O-ethyl.

Also particularly preferred is one of the above medicament combinations, which comprises at least one EP4 receptor antagonist (2) in addition to one or more, preferably one, PDE4 inhibitor of general formula 1, wherein $R^3$ is a monocyclic five- or six-membered heteroaryl ring selected from among pyrrole, pyrazole, furan, thiophene, thiazole, imidazole, oxazole, pyridazine, pyrimidine, pyrazine, thiadiazole, oxadiazole, triazine, isoxazole, isothiazole and pyridine, which may optionally be substituted by one or more groups selected from among F, Cl, Br, $CF_3$, $CHF_2$, $CH_2F$, CN, OH, -methyl, ethyl, propyl, isopropyl, —O-methyl, O-ethyl, —COOmethyl, —COOethyl, $SO_2$—$(CH_3)$, $SO_2$—$(CH_2CH_3)$, phenyl, -methylene-phenyl, -ethylene-phenyl, —$NH_2$, —$NH(CH_3)$, $N(CH_3)_2$, -methylene-$NH_2$, -methylene-$NH(CH_3)$, -methylene-N$(CH_3)_2$, a $C_{3-6}$-cycloalkyl, a methylene-$C_{3-6}$-cycloalkyl, a het, a hetaryl, -methylene-hetaryl, and -methylene-het, which in turn may optionally be substituted by one or more groups selected from among OH, F, Cl, Br, $CF_3$, $CHF_2$, $CH_2F$, methyl, ethyl, propyl, isopropyl, phenyl, —COO($CH_3$), —O-methyl and —O-ethyl.

In another particularly preferred aspect the invention relates to one of the above mentioned medicament combinations, which comprises at least one EP4 receptor antagonist (2), in addition to one or more, preferably one, PDE4 inhibitor of general formula 1, wherein $R^3$ denotes a bicyclic 9- to 11-membered heterocyclic group selected from among benzoxazole, benzodioxole, dihydrobenzodioxin, benzodioxin, benzisoxazole, benzothiazole, benzisothiazole, thienopyrimidine, furopyrimidine, thienopyridine, furopyridine, indole, isoindole, quinoxaline, naphthyridine, pyridopyrazine, pyridopyrimidine, quinoline, isoquinoline, benzoimidazole, 6,7,8,9-tetrahydro-5H-pyrazino[2,3-d]azepin, benzothiophene, benzofuran, quinazoline, indazole, isobenzofuran and pteridine, which may optionally be substituted by one or more groups selected from among F, Cl, Br, $CF_3$, $CHF_2$, $CH_2F$, CN, OH, -methyl, ethyl, propyl, isopropyl, —O-methyl, O-ethyl, —COOmethyl, —COOethyl, $SO_2$—$(CH_3)$, $SO_2$—$(CH_2CH_3)$, phenyl, -methylene-phenyl, -ethylene-phenyl, —$NH_2$, —$NH(CH_3)$, $N(CH_3)_2$, -methylene-$NH_2$, -methylene-$NH(CH_3)$, -methylene-N$(CH_3)_2$, a $C_{3-6}$-cycloalkyl, a methylene-$C_{3-6}$-cycloalkyl, a het, a hetaryl, -methylene-hetaryl, and -methylene-het, which in turn may optionally be substituted by one or more groups selected from among OH, F, Cl, Br, $CF_3$, $CHF_2$, $CH_2F$, methyl, ethyl, propyl, isopropyl, phenyl, —COO($CH_3$), —O-methyl and —O-ethyl.

Also particularly preferred is one of the above medicament combinations, which comprises at least one EP4 receptor antagonist (2) in addition to one or more, preferably one, PDE4 inhibitor of general formula 1, wherein $R^1$ is H, $R^2$ is a group selected from among

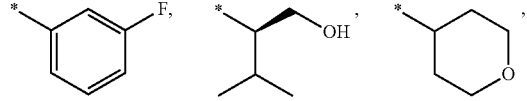

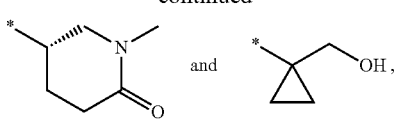

R³ is a group selected from among

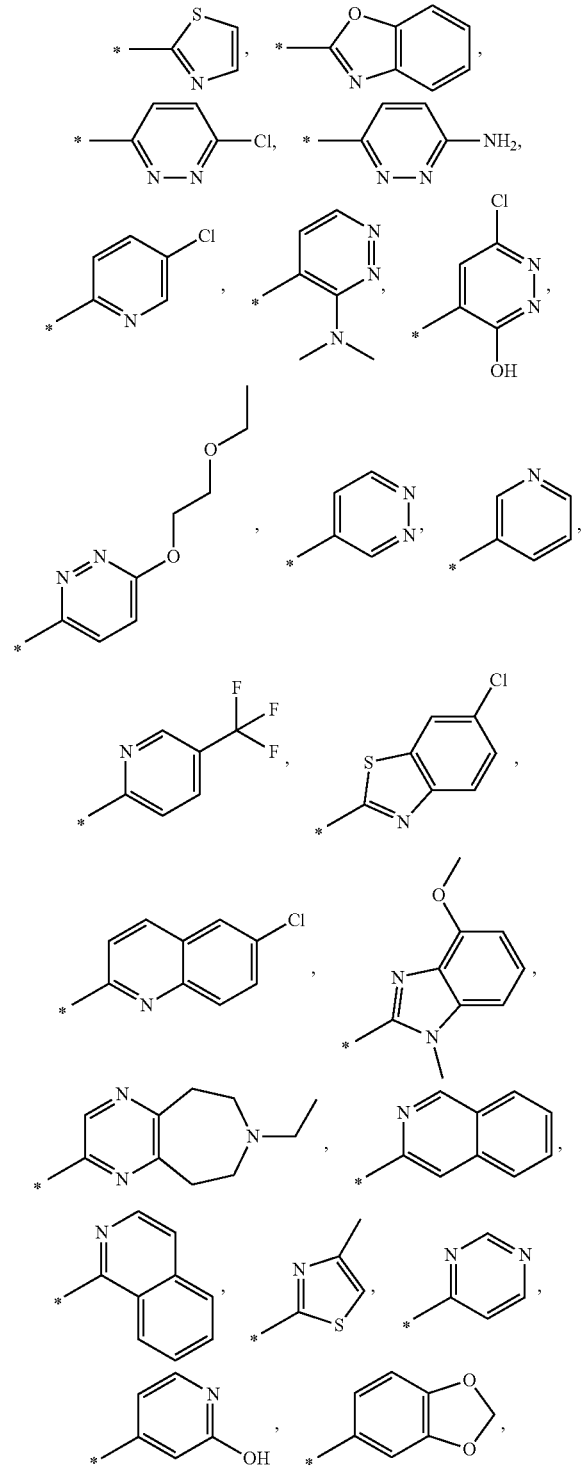

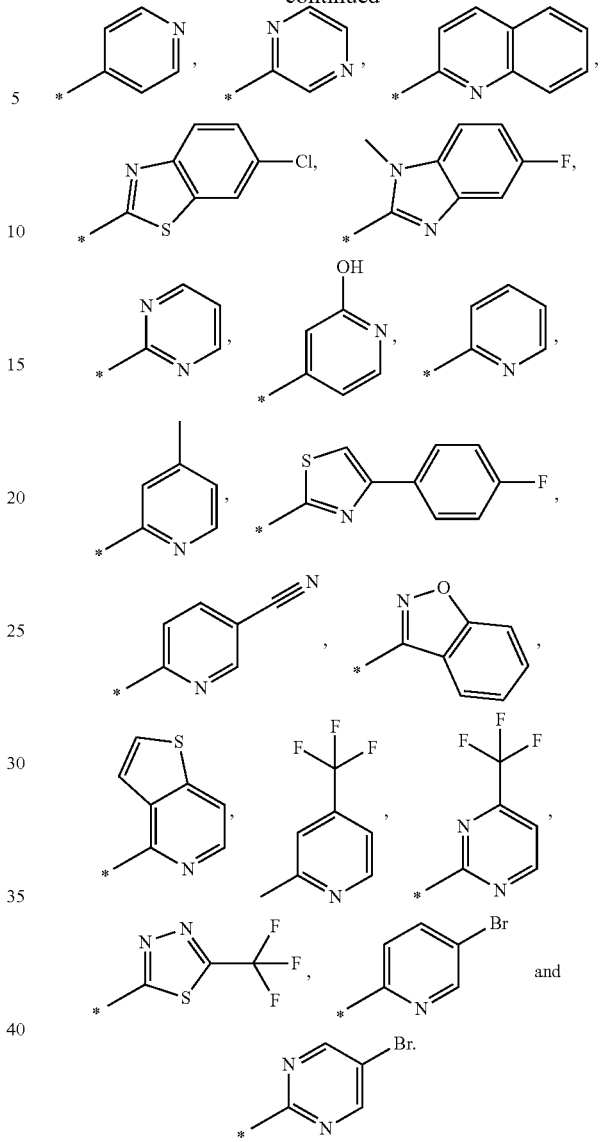

In another particularly preferred aspect the invention relates to one of the above mentioned medicament combinations, which comprises at least one EP4 receptor antagonist (2) in addition to one or more, preferably one, PDE4 inhibitor of general formula 1 selected from among:

1.1 (3-fluorophenyl)-[5-oxo-2-(4-thiazol-2-yl-piperazin-1-yl)-6,7-dihydro-5H-5λ⁴-thieno[3,2-d]pyrimidin-4-yl]-amine 1.2 (R)-3-methyl-2-[5-oxo-2-(4-thiazol-2-yl-piperazin-1-yl)-6,7-dihydro-5H-5λ⁴-thieno[3,2-d]pyrimidin-4-ylamino]-butan-1-ol 1.3 [2-(4-benzoxazol-2-yl-piperazin-1-yl)-5-oxo-6,7-dihydro-5H-5λ⁴-thieno[3,2-d]pyrimidin-4-yl]-(3-fluorophenyl)-amine 1.4 [2-(4-benzoxazol-2-yl-piperazin-1-yl)-5-oxo-6,7-dihydro-5H-5λ⁴-thieno[3,2-d]pyrimidin-4-yl]-(tetrahydropyran-4-yl)-amine 1.5 (R)-2-{2-[4-(6-chloropyridazin-3-yl)-piperazin-1-yl]-5-oxo-6,7-dihydro-5H-5λ⁴-thieno[3,2-d]pyrimidin-4-ylamino}-3-methylbutan-1-ol 1.6 {2-[4-(6-chloropyridazin-3-yl)-piperazin-1-yl]-5-oxo-6,7-dihydro-5H-5λ⁴-thieno[3,2-d]pyrimidin-4-yl}-(3-fluorophenyl)-amine 1.7 (R)-2-[2-(4-benzoxazol-2-yl-piperazin-1-yl)-5-oxo-6,7-dihydro-5H-5λ⁴-thieno[3,2-d]pyrimidin-4-ylamino]-3-methylbutan-1-ol 1.8 (1-{2-[4-(5-chloropyridin-2-yl)-piperazin-1-yl]-5-oxo-6,7-dihydro-5H-5λ⁴-thieno[3,2-d]pyrimidin-4-ylamino}-cyclopropyl)-methanol 1.9 {2-[4-(5-chloropyridin-2-yl)-piperazin-1-yl]-5-oxo-6,7-dihydro-5H-5λ⁴-thieno[3,2-d]pyrimidin-4-yl}-(tetrahydropyran-4-yl)-amine 1.10 {2-[4-(3-dimethylaminopyridazin-4-yl)-piperazin-1-yl]-5-oxo-6,7-dihydro-5H-5λ⁴-thieno[3,2-d]pyrimidin-4-yl}-(3-fluorophenyl)-amine 1.11 6-chloro-4-{4-[4-(3-fluorophenylamino)-5-oxo-6,7-dihydro-5H-5λ⁴-thieno[3,2-d]pyrimidin-2-yl]-piperazin-1-yl}-pyridazin-3-ol 1.12 2-{4-[6-(2-ethoxyethoxy)-pyridazin-3-yl]-piperazin-1-yl}-5-oxo-6,7-dihydro-5H-5λ⁴-thieno[3,2-d]pyrimidin-4-yl)-(3-fluorophenyl)-amine 1.13 (3-fluorophenyl)-[5-oxo-2-(4-pyridazin-4-yl-piperazin-1-yl)-6,7-dihydro-5H-5λ⁴-thieno[3,2-d]pyrimidin-4-yl]-amine 1.14 (R)-2-{2-[4-(4-methoxy-1-methyl-1H-benzimidazol-2-yl)-piperazin-1-yl]-5-oxo-6,7-dihydro-5H-5λ⁴-thieno[3,2-d]pyrimidin-4-ylamino}-3-methylbutan-1-ol 1.15 (R)-2-{2-[4-(7-ethyl-6,7,8,9-tetrahydro-5H-pyrazino[2,3-d]azepin-2-yl)-piperazin-1-yl]-5-oxo-6,7-dihydro-5H-5λ⁴-thieno[3,2-d]pyrimidin-4-ylamino}-3-methylbutan-1-ol 1.16 (R)-3-methyl-2-[5-oxo-2-(4-pyrimidin-4-yl-piperazin-1-yl)-6,7-dihydro-5H-5λ⁴-thieno[3,2-d]pyrimidin-4-ylamino]-butan-1-ol 1.17 4-{4-[4-((R)-1-hydroxymethyl-2-methylpropylamino)-5-oxo-6,7-dihydro-5H-5λ⁴-thieno[3,2-d]pyrimidin-2-yl]-piperazin-1-yl}-pyridin-2-ol 1.18 (R)-3-methyl-2-[5-oxo-2-(4-pyridin-4-yl-piperazin-1-yl)-6,7-dihydro-5H-5λ⁴-thieno[3,2-d]pyrimidin-4-ylamino]-butan-1-ol 1.19 (R)-2-{2-[4-(3-dimethylaminopyridazin-4-yl)-piperazin-1-yl]-5-oxo-6,7-dihydro-5H-5λ⁴-thieno[3,2-d]pyrimidin-4-ylamino}-3-methylbutan-1-ol 1.20 6-chloro-4-{4-[4-((R)-1-hydroxymethyl-2-methylpropylamino)-5-oxo-6,7-dihydro-5H-5λ⁴-thieno[3,2-d]pyrimidin-2-yl]-piperazin-1-yl}-pyridazin-3-ol 1.21 (R)-2-(2-{4-[6-(2-ethoxyethoxy)-pyridazin-3-yl]-piperazin-1-yl}-5-oxo-6,7-dihydro-5H-5λ⁴-thieno[3,2-d]pyrimidin-4-ylamino)-3-methylbutan-1-ol 1.22 (R)-3-methyl-2-[5-oxo-2-(4-pyridazin-4-yl-piperazin-1-yl)-6,7-dihydro-5H-5λ⁴-thieno[3,2-d]pyrimidin-4-ylamino]-butan-1-ol 1.23 {1-[5-oxo-2-(4-pyrimidin-4-yl-piperazin-1-yl)-6,7-dihydro-5H-5λ⁴-thieno[3,2-d]pyrimidin-4-ylamino]-cyclopropyl}-methanol 1.24 {1-[5-oxo-2-(4-pyridin-4-yl-piperazin-1-yl)-6,7-dihydro-5H-5λ⁴-thieno[3,2-d]pyrimidin-4-ylamino]-cyclopropyl}-methanol 1.25 (S)-1-methyl-5-[5-oxo-2-(4-pyrimidin-4-yl-piperazin-1-yl)-6,7-dihydro-5H-5λ⁴-thieno[3,2-d]pyrimidin-4-ylamino]-piperidin-2-one 1.26 {2-[4-(5-fluoro-1-methyl-1H-benzoimidazol-2-yl)-piperazin-1-yl]-5-oxo-6,7-dihydro-5H-5λ⁴-thieno[3,2-d]pyrimidin-4-yl}-(tetrahydropyran-4-yl)-amine 1.27 [5-oxo-2-(4-pyridin-4-yl-piperazin-1-yl)-6,7-dihydro-5H-5λ⁴-thieno[3,2-d]pyrimidin-4-yl]-(tetrahydropyran-4-yl)-amine 1.28 (3-fluorophenyl)-{2-[4-(4-methoxy-1-methyl-1H-benzimidazol-2-yl)-piperazin-1-yl]-5-oxo-6,7-dihydro-5H-5λ⁴-thieno[3,2-d]pyrimidin-4-yl}-amine 1.29 {2-[4-(7-ethyl-6,7,8,9-tetrahydro-5H-pyrazino[2,3-d]azepin-2-yl)-piperazin-1-yl]-5-oxo-6,7-dihydro-5H-5λ⁴-thieno[3,2-d]pyrimidin-4-yl}-(3-fluorophenyl)-amine 1.30 (3-fluorophenyl)-[5-oxo-2-(4-pyrimidin-4-yl-piperazin-1-yl)-6,7-dihydro-5H-5λ⁴-thieno[3,2-d]pyrimidin-4-yl]-amine 1.31 4-{4-[4-(3-fluorophenylamino)-5-oxo-6,7-dihydro-5H-5λ⁴-thieno[3,2-d]pyrimidin-2-yl]-piperazin-1-yl}-pyridin-2-ol 1.32 (3-fluorophenyl)-[5-oxo-2-(4-pyridin-4-yl-piperazin-1-yl)-6,7-dihydro-5H-5λ⁴-thieno[3,2-d]pyrimidin-4-yl]-amine 1.33 (3-fluorophenyl)-(2-{4-[4-(4-fluorophenyl)-thiazol-2-yl]-piperazin-1-yl}-5-oxo-6,7-dihydro-5H-5λ⁴-thieno[3,2-d]pyrimidin-4-yl)-amine 1.34 [2-(4-benzo[d]isoxazol-3-yl-piperazin-1-yl)-5-oxo-6,7-dihydro-5H-5λ⁴-thieno[3,2-d]pyrimidin-4-yl]-(3-fluorophenyl)-amine 1.35 (R)-2-(2-{4-[4-(4-fluorophenyl)-thiazol-2-yl]-piperazin-1-yl}-5-oxo-6,7-dihydro-5H-5λ⁴-thieno[3,2-d]pyrimidin-4-ylamino)-3-methylbutan-1-ol 1.36 (R)-2-[2-(4-benzo[d]isoxazol-3-yl-piperazin-1-yl)-5-oxo-6,7-dihydro-5H-5λ⁴-thieno[3,2-d]pyrimidin-4-ylamino]-3-methylbutan-1-ol.

The above mentioned compounds of formula 1 are prepared as described in detail in the synthesis instructions.

Particularly preferred within the scope of the present invention are those of the above mentioned medicament combinations that are selected from among 2.1 and 1.1; 2.1 and 1.2; 2.1 and 1.3, 2.1 and 1.4; 2.1 and 1.5; 2.1 and 1.6; 2.1 and 1.7; 2.1 and 1.8, 2.1 and 1.9; 2.1 and 1.10; 2.1 and 1.11; 2.1 and 1.12; 2.1 and 1.13, 2.1 and 1.14; 2.1 and 1.15; 2.1 and 1.16; 2.1 and 1.17; 2.1 and 1.18, 2.1 and 1.19; 2.1 and 1.20; 2.1 and 1.21; 2.1 and 1.22; 2.1 and 1.23, 2.1 and 1.24; 2.1 and 1.25; 2.1 and 1.26; 2.1 and 1.27; 2.1 and 1.28, 2.1 and 1.29; 2.1 and 1.30; 2.1 and 1.31; 2.1 and 1.32; 2.1 and 1.33, 2.1 and 1.34; 2.1 and 1.35; 2.1 and 1.36;

2.2 and 1.1; 2.2 and 1.2; 2.2 and 1.3, 2.2 and 1.4; 2.2 and 1.5; 2.2 and 1.6; 2.2 and 1.7; 2.2 and 1.8, 2.2 and 1.9; 2.2 and 1.10; 2.2 and 1.11; 2.2 and 1.12; 2.2 and 1.13, 2.2 and 1.14; 2.2 and 1.15; 2.2 and 1.16; 2.2 and 1.17; 2.2 and 1.18, 2.2 and 1.19; 2.2 and 1.20; 2.2 and 1.21; 2.2 and 1.22; 2.2 and 1.23, 2.2 and 1.24; 2.2 and 1.25; 2.2 and 1.26; 2.2 and 1.27; 2.2 and 1.28, 2.2 and 1.29; 2.2 and 1.30; 2.2 and 1.31; 2.2 and 1.32; 2.2 and 1.33, 2.2 and 1.34; 2.2 and 1.35; 2.2 and 1.36;

2.3 and 1.1; 2.1 and 1.3; 2.1 and 1.3, 2.3 and 1.4; 2.3 and 1.5; 2.3 and 1.6; 2.3 and 1.7; 2.3 and 1.8, 2.3 and 1.9; 2.3 and 1.10; 2.3 and 1.11; 2.3 and 1.12; 2.3 and 1.13, 2.3 and 1.14; 2.3 and 1.15; 2.3 and 1.16; 2.3 and 1.17; 2.3 and 1.18, 2.3 and 1.19; 2.3 and 1.20; 2.3 and 1.21; 2.3 and 1.22; 2.3 and 1.23, 2.3 and 1.24; 2.3 and 1.25; 2.3 and 1.26; 2.3 and 1.27; 2.3 and 1.28, 2.3 and 1.29; 2.3 and 1.30; 2.3 and 1.31; 2.3 and 1.32; 2.3 and 1.33, 2.3 and 1.34; 2.3 and 1.35; 2.3 and 1.36;

2.4 and 1.1; 2.4 and 1.2; 2.4 and 1.3, 2.4 and 1.4; 2.4 and 1.5; 2.4 and 1.6; 2.4 and 1.7; 2.4 and 1.8, 2.4 and 1.9; 2.4 and 1.10; 2.4 and 1.11; 2.4 and 1.12; 2.4 and 1.13, 2.4 and 1.14; 2.4 and 1.15; 2.4 and 1.16; 2.4 and 1.17; 2.4 and 1.18, 2.4 and 1.19; 2.4 and 1.20; 2.4 and 1.21; 2.4 and 1.22; 2.4 and 1.23, 2.4 and 1.24; 2.4 and 1.25; 2.4 and 1.26; 2.4 and 1.27; 2.4 and 1.28, 2.4 and 1.29; 2.4 and 1.30; 2.4 and 1.31; 2.4 and 1.32; 2.4 and 1.33, 2.4 and 1.34; 2.4 and 1.35; 2.4 and 1.36;

2.5 and 1.1; 2.5 and 1.2; 2.5 and 1.3; 2.5 and 1.4; 2.5 and 1.5; 2.5 and 1.6; 2.5 and 1.7; 2.5 and 1.8; 2.5 and 1.9; 2.5 and 1.10; 2.5 and 1.11; 2.5 and 1.12; 2.5 and 1.13, 2.5 and 1.14; 2.5 and 1.15; 2.5 and 1.16; 2.5 and 1.17; 2.5 and 1.18, 2.5 and 1.19; 2.5 and 1.20; 2.5 and 1.21; 2.5 and 1.22; 2.5 and 1.23, 2.5 and 1.24; 2.5 and 1.25; 2.5 and 1.26; 2.5 and 1.27; 2.5 and 1.28, 2.5 and 1.29; 2.5 and 1.30; 2.5 and 1.31; 2.5 and 1.32; 2.5 and 1.33, 2.5 and 1.34; 2.5 and 1.35; 2.5 and 1.36;

2.6 and 1.1; 2.6 and 1.2; 2.6 and 1.3, 2.6 and 1.4; 2.6 and 1.5; 2.6 and 1.6; 2.6 and 1.7; 2.6 and 1.8, 2.6 and 1.9; 2.6 and 1.10; 2.6 and 1.11; 2.6 and 1.12; 2.6 and 1.13, 2.6 and 1.14; 2.6 and 1.15; 2.6 and 1.16; 2.6 and 1.17; 2.6 and 1.18, 2.6 and 1.19; 2.6 and 1.20; 2.6 and 1.21; 2.6 and 1.22; 2.6 and 1.23, 2.6 and 1.24; 2.6 and 1.25; 2.6 and 1.26; 2.6 and 1.27; 2.6 and 1.28, 2.6 and 1.29; 2.6 and 1.30; 2.6 and 1.31; 2.6 and 1.32; 2.6 and 1.33, 2.6 and 1.34; 2.6 and 1.35; 2.6 and 1.36;

2.7 and 1.1; 2.7 and 1.2; 2.7 and 1.3, 2.7 and 1.4; 2.7 and 1.5; 2.7 and 1.6; 2.7 and 1.7; 2.7 and 1.8, 2.7 and 1.9; 2.7 and 1.10; 2.7 and 1.11; 2.7 and 1.12; 2.7 and 1.13, 2.7 and 1.14; 2.7 and 1.15; 2.7 and 1.16; 2.7 and 1.17; 2.7 and 1.18, 2.7 and 1.19; 2.7 and 1.20; 2.7 and 1.21; 2.7 and 1.22; 2.7 and 1.23, 2.7 and 1.24; 2.7 and 1.25; 2.7 and 1.26; 2.7 and 1.27; 2.7 and 1.28, 2.7 and 1.29; 2.7 and 1.30; 2.7 and 1.31; 2.7 and 1.32; 2.7 and 1.33, 2.7 and 1.34; 2.7 and 1.35; 2.7 and 1.36;

2.8 and 1.1; 2.8 and 1.2; 2.8 and 1.3, 2.8 and 1.4; 2.8 and 1.5; 2.8 and 1.6; 2.8 and 1.7; 2.8 and 1.8, 2.8 and 1.9; 2.8 and 1.10; 2.8 and 1.11; 2.8 and 1.12; 2.8 and 1.13, 2.8 and 1.14; 2.8 and 1.15; 2.8 and 1.16; 2.8 and 1.17; 2.8 and 1.18, 2.8 and 1.19; 2.8 and 1.20; 2.8 and 1.21; 2.8 and 1.22; 2.8 and 1.23, 2.8 and 1.24; 2.8 and 1.25; 2.8 and 1.26; 2.8 and 1.27; 2.8 and 1.28, 2.8 and 1.29; 2.8 and 1.30; 2.8 and 1.31; 2.8 and 1.32; 2.8 and 1.33, 2.8 and 1.34; 2.8 and 1.35; 2.8 and 1.36.

Also particularly preferred is one of the above medicament combinations in which the PDE4 inhibitor (1) is contained in a daily dose of 0.01 mg to 50 mg, preferably 0.1 mg to 10 mg.

In another particularly preferred aspect the invention relates to one of the above mentioned medicament combinations, in which the EP4-receptor-antagonist (2) is used in a daily dose of 0.001 to 100 mg/kg body weight, preferably 0.01 to 50 mg/kg body weight, more preferably 0.1 to 10 mg/kg body weight.

Also particularly preferred is one of the above medicament combinations wherein the EP4-receptor antagonist (2) and the PDE4 inhibitor (1) are used in a ratio by weight of 1:1 to 200:1, preferably in a ratio by weight of 10:1 to 150:1, particularly preferably in a ratio by weight of 30:1 to 100:1.

The present invention further relates to the use of an EP4-receptor-antagonist (2) for reducing the side effects of one or more PDE4-inhibitors in the treatment of a disease selected from among respiratory complaints, pulmonary diseases, gastrointestinal complaints, diseases such as inflammatory diseases of the joints, skin or eyes, cancers and diseases of the peripheral or central nervous system.

The present invention further relates to the use of a combination containing one or more PDE4-inhibitors (1) and at least one EP4 receptor antagonist (2) for the treatment of a disease selected from among respiratory complaints, pulmonary diseases, gastrointestinal complaints, diseases such as inflammatory diseases of the joints, skin or eyes, cancers and diseases of the peripheral or central nervous system.

In another preferred aspect the present invention relates to one of the above mentioned uses, wherein the or each PDE4-inhibitor is a compound of general formula 1, wherein X, $R^1$, $R^2$ and $R^3$ are as hereinbefore defined.

The present invention further relates to the above-mentioned uses of an EP4-receptor-antagonist (2) or a combination containing one or more PDE4-inhibitors (1) and at least one EP4 receptor antagonist (2) for the treatment of a disease selected from COPD, chronic sinusitis, asthma, Crohn's disease and ulcerative colitis.

In a variant of the above-mentioned uses the PDE4 inhibitor (1) and the at least one EP4-receptor antagonist (2) are administered simultaneously in a single common formulation.

In another variant of the above-mentioned uses the PDE4 inhibitor (1) and the at least one EP4-receptor antagonist (2) may, however, also be administered in two separate formulations offset from one another within a time interval of 0 to 6 hours.

In this separate administration in two separate formulations the formulation containing the PDE4 inhibitor—particularly the PDE4 inhibitor of formula 1—may be an oral or inhalative formulation, but is preferably an oral formulation, and the formulation containing the at least one EP4 receptor antagonist (2) is preferably an oral formulation.

Moreover, when the combination is used in separate formulations for preparing a medicament combination for the treatment of the above mentioned diseases the formulation containing the PDE4 inhibitor—particularly the PDE4 inhibitor of formula 1—is preferably administered once a day and the formulation containing the at least one EP4 receptor antagonist (2) is preferably administered either once or twice a day.

It is also preferable to use the combination containing one or more PDE4-inhibitors—particularly one or more of the PDE4-inhibitors according to formula 1—and containing at least one EP4 receptor antagonist (2) to prepare a medicament combination for the treatment of the above mentioned diseases, using PDE4-inhibitors of general formula 1 wherein $R^1$ is H, $R^2$ is a group selected from among R³ is a group selected from among

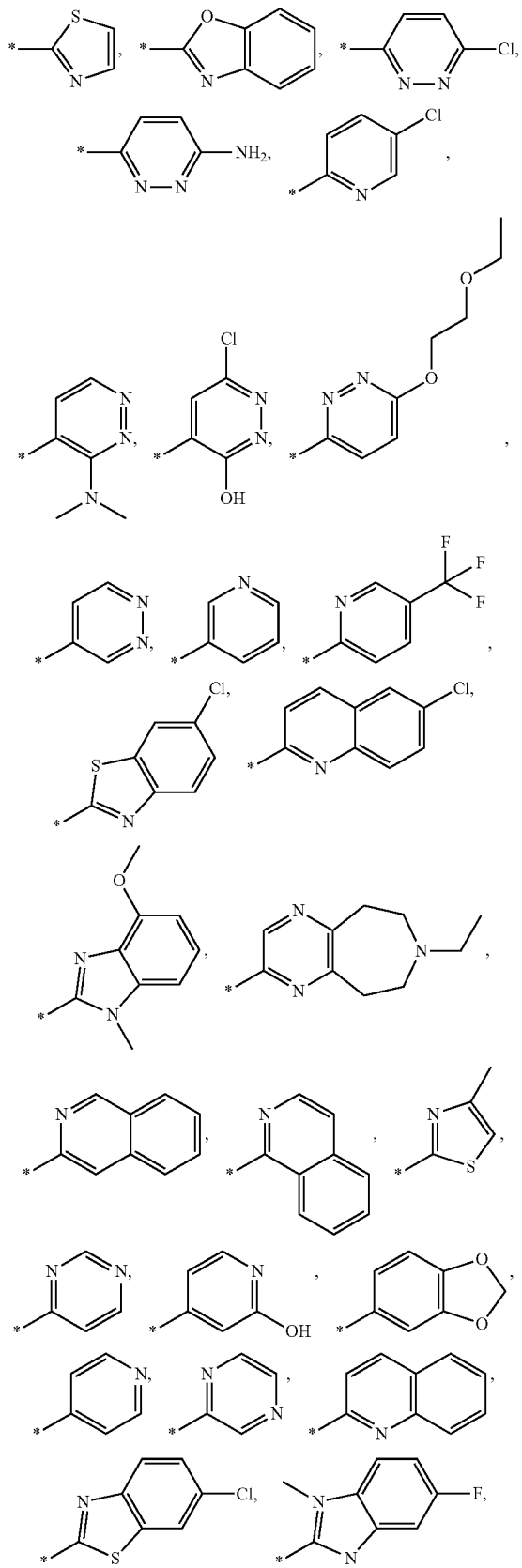

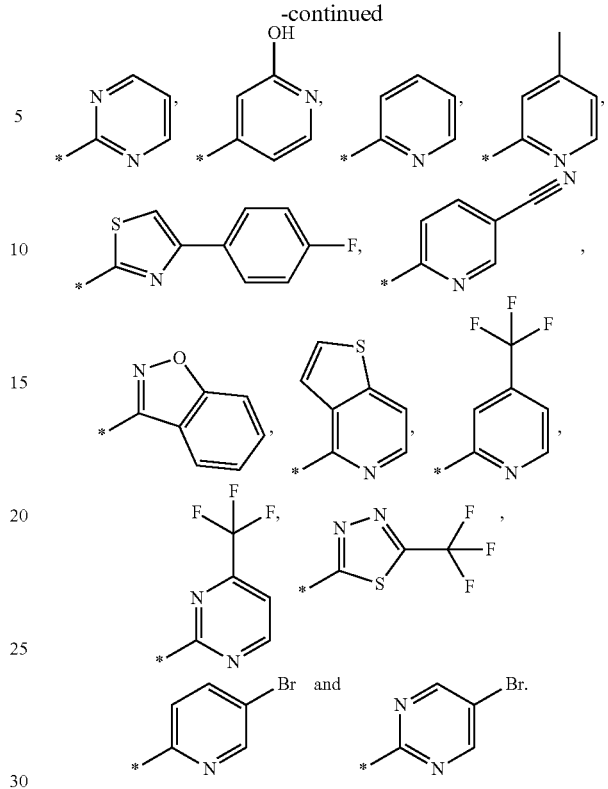

In particular, in the above mentioned uses, the PDE4-inhibitors of formula 1 are selected from:

1.1 (3-fluorophenyl)-[5-oxo-2-(4-thiazol-2-yl-piperazin-1-yl)-6,7-dihydro-5H-5λ⁴-thieno[3,2-d]pyrimidin-4-yl]-amine 1.2 (R)-3-methyl-2-[5-oxo-2-(4-thiazol-2-yl-piperazin-1-yl)-6,7-dihydro-5H-5λ⁴-thieno[3,2-d]pyrimidin-4-ylamino]-butan-1-ol 1.3 [2-(4-benzoxazol-2-yl-piperazin-1-yl)-5-oxo-6,7-dihydro-5H-5λ⁴-thieno[3,2-d]pyrimidin-4-yl]-(3-fluorophenyl)-amine 1.4 [2-(4-benzoxazol-2-yl-piperazin-1-yl)-5-oxo-6,7-dihydro-5H-5λ⁴-thieno[3,2-d]pyrimidin-4-yl]-(tetrahydropyran-4-yl)-amine 1.5 (R)-2-{2-[4-(6-chloropyridazin-3-yl)-piperazin-1-yl]-5-oxo-6,7-dihydro-5H-5λ⁴-thieno[3,2-d]pyrimidin-4-ylamino}-3-methylbutan-1-ol 1.6 {2-[4-(6-chloropyridazin-3-yl)-piperazin-1-yl]-5-oxo-6,7-dihydro-5H-5λ⁴-thieno[3,2-d]pyrimidin-4-yl}-(3-fluorophenyl)-amine 1.7 (R)-2-[2-(4-benzoxazol-2-yl-piperazin-1-yl)-5-oxo-6,7-dihydro-5H-5λ⁴-thieno[3,2-d]pyrimidin-4-ylamino]-3-methylbutan-1-ol 1.8 (1-{2-[4-(5-chloropyridin-2-yl)-piperazin-1-yl]-5-oxo-6,7-dihydro-5H-5λ⁴-thieno[3,2-d]pyrimidin-4-ylamino}-cyclopropyl)-methanol 1.9 {2-[4-(5-chloropyridin-2-yl)-piperazin-1-yl]-5-oxo-6,7-dihydro-5H-5λ⁴-thieno[3,2-d]pyrimidin-4-yl}-(tetrahydropyran-4-yl)-amine 1.10 {2-[4-(3-dimethylaminopyridazin-4-yl)-piperazin-1-yl]-5-oxo-6,7-dihydro-5H-5λ⁴-thieno[3,2-d]pyrimidin-4-yl}-(3-fluorophenyl)-amine 1.11 6-chloro-4-{4-[4-(3-fluorophenylamino)-5-oxo-6,7-dihydro-5H-5λ⁴-thieno[3,2-d]pyrimidin-2-yl]-piperazin-1-yl}-pyridazin-3-ol 1.12  2-{4-[6-(2-ethoxyethoxy)-pyridazin-3-yl]-piperazin-1-yl}-5-oxo-6,7-dihydro-5H-5$\lambda^4$-thieno[3,2-d]pyrimidin-4-yl)-(3-fluorophenyl)-amine 1.13  (3-fluorophenyl)-[5-oxo-2-(4-pyridazin-4-yl-piperazin-1-yl)-6,7-dihydro-5H-5$\lambda^4$-thieno[3,2-d]pyrimidin-4-yl]-amine 1.14  (R)-2-{2-[4-(4-methoxy-1-methyl-1H-benzimidazol-2-yl)-piperazin-1-yl]-5-oxo-6,7-dihydro-5H-5$\lambda^4$-thieno[3,2-d]pyrimidin-4-ylamino}-3-methylbutan-1-ol 1.15  (R)-2-{2-[4-(7-ethyl-6,7,8,9-tetrahydro-5H-pyrazino[2,3-d]azepin-2-yl)-piperazin-1-yl]-5-oxo-6,7-dihydro-5H-5$\lambda^4$-thieno[3,2-d]pyrimidin-4-ylamino}-3-methylbutan-1-ol 1.16  (R)-3-methyl-2-[5-oxo-2-(4-pyrimidin-4-yl-piperazin-1-yl)-6,7-dihydro-5H-5$\lambda^4$-thieno[3,2-d]pyrimidin-4-ylamino]-butan-1-ol 1.17  4-{4-[4-((R)-1-hydroxymethyl-2-methylpropylamino)-5-oxo-6,7-dihydro-5H-5$\lambda^4$-thieno[3,2-d]pyrimidin-2-yl]-piperazin-1-yl}-pyridin-2-ol 1.18  (R)-3-methyl-2-[5-oxo-2-(4-pyridin-4-yl-piperazin-1-yl)-6,7-dihydro-5H-5$\lambda^4$-thieno[3,2-d]pyrimidin-4-ylamino]-butan-1-ol 1.19  (R)-2-{2-[4-(3-dimethylaminopyridazin-4-yl)-piperazin-1-yl]-5-oxo-6,7-dihydro-5H-5$\lambda^4$-thieno[3,2-d]pyrimidin-4-ylamino}-3-methylbutan-1-ol 1.20  6-chloro-4-{4-[4-((R)-1-hydroxymethyl-2-methylpropylamino)-5-oxo-6,7-dihydro-5H-5$\lambda^4$-thieno[3,2-d]pyrimidin-2-yl]-piperazin-1-yl}-pyridazin-3-ol 1.21  (R)-2-(2-{4-[6-(2-ethoxyethoxy)-pyridazin-3-yl]-piperazin-1-yl}-5-oxo-6,7-dihydro-5H-5$\lambda^4$-thieno[3,2-d]pyrimidin-4-ylamino)-3-methylbutan-1-ol 1.22  (R)-3-methyl-2-[5-oxo-2-(4-pyridazin-4-yl-piperazin-1-yl)-6,7-dihydro-5H-5$\lambda^4$-thieno[3,2-d]pyrimidin-4-ylamino]-butan-1-ol 1.23  {1-[5-oxo-2-(4-pyrimidin-4-yl-piperazin-1-yl)-6,7-dihydro-5H-5$\lambda^4$-thieno[3,2-d]pyrimidin-4-ylamino]-cyclopropyl}-methanol 1.24  {1-[5-oxo-2-(4-pyridin-4-yl-piperazin-1-yl)-6,7-dihydro-5H-5$\lambda^4$-thieno[3,2-d]pyrimidin-4-ylamino]-cyclopropyl}-methanol 1.25  (S)-1-methyl-5-[5-oxo-2-(4-pyrimidin-4-yl-piperazin-1-yl)-6,7-dihydro-5H-5$\lambda^4$-thieno[3,2-d]pyrimidin-4-ylamino]-piperidin-2-one 1.26  {2-[4-(5-fluoro-1-methyl-1H-benzoimidazol-2-yl)-piperazin-1-yl]-5-oxo-6,7-dihydro-5H-5$\lambda^4$-thieno[3,2-d]pyrimidin-4-yl}-(tetrahydropyran-4-yl)-amine 1.27  [5-oxo-2-(4-pyridin-4-yl-piperazin-1-yl)-6,7-dihydro-5H-5$\lambda^4$-thieno[3,2-d]pyrimidin-4-yl]-(tetrahydropyran-4-yl)-amine 1.28  (3-fluorophenyl)-{2-[4-(4-methoxy-1-methyl-1H-benzimidazol-2-yl)-piperazin-1-yl]-5-oxo-6,7-dihydro-5H-5$\lambda^4$-thieno[3,2-d]pyrimidin-4-yl}-amine 1.29  {2-[4-(7-ethyl-6,7,8,9-tetrahydro-5H-pyrazino[2,3-d]azepin-2-yl)-piperazin-1-yl]-5-oxo-6,7-dihydro-5H-5$\lambda^4$-thieno[3,2-d]pyrimidin-4-yl}-(3-fluorophenyl)-amine 1.30  (3-fluorophenyl)-[5-oxo-2-(4-pyrimidin-4-yl-piperazin-1-yl)-6,7-dihydro-5H-5$\lambda^4$-thieno[3,2-d]pyrimidin-4-yl]-amine 1.31  4-{4-[4-(3-fluorophenylamino)-5-oxo-6,7-dihydro-5H-5$\lambda^4$-thieno[3,2-d]pyrimidin-2-yl]-piperazin-1-yl}-pyridin-2-ol 1.32  (3-fluorophenyl)-[5-oxo-2-(4-pyridin-4-yl-piperazin-1-yl)-6,7-dihydro-5H-5$\lambda^4$-thieno[3,2-d]pyrimidin-4-yl]-amine 1.33  (3-fluorophenyl)-(2-{4-[4-(4-fluorophenyl)-thiazol-2-yl]-piperazin-1-yl}-5-oxo-6,7-dihydro-5H-5$\lambda^4$-thieno[3,2-d]pyrimidin-4-yl)-amine 1.34  [2-(4-benzo[d]isoxazol-3-yl-piperazin-1-yl)-5-oxo-6,7-dihydro-5H-5$\lambda^4$-thieno[3,2-d]pyrimidin-4-yl]-(3-fluorophenyl)-amine 1.35  (R)-2-(2-{4-[4-(4-fluorophenyl)-thiazol-2-yl]-piperazin-1-yl}-5-oxo-6,7-dihydro-5H-5$\lambda^4$-thieno[3,2-d]pyrimidin-4-ylamino)-3-methylbutan-1-ol 1.36  (R)-2-[2-(4-benzo[d]isoxazol-3-yl-piperazin-1-yl)-5-oxo-6,7-dihydro-5H-5$\lambda^4$-thieno[3,2-d]pyrimidin-4-ylamino]-3-methylbutan-1-ol.

In these above mentioned uses the EP4-receptor-antagonists (2) are preferably selected from among:

[N-{[4-(5,9-diethoxy-6-oxo-6,8-dihydro-7H-pyrrolo[3,4-g]quinolin-7-yl)-3-methylbenzyl]sulphonyl}-2-(2-methoxyphenyl)acetamide](2.1);

5-butyl-2,4-dihydro-4-[[2'-[N-(3-methyl-2-thiophene-carbonyl)sulphamoyl]biphenyl-4-yl]methyl]-2-[(2-trifluoromethyl)phenyl]-1,2,4-triazol-3-one (2.2);

(4-{(1S)-1-[({5-chloro-2-[(4-fluorophenyl)oxy]phenyl}carbonyl)amino]ethyl}benzoic acid (2.3);

N-[({2-[4-(2-ethyl-4,6-dimethyl-1H-imidazo[4,5-c]pyridin-1-yl)phenyl]ethyl}amino)carbonyl]-4-methylbenzene sulphonamide (2.4);

4-[[4-(5-methoxy-2-pyridinyl)phenoxy]methyl]-5-methyl-N-[(2-methylphenyl)sulphonyl]-2-furancarboxamide (2.5);

methyl 11alpha,15alpha-dihydroxy-16-(3-methoxymethylphenyl)-9-oxo-17,18,19,20-tetranor-5-thia-13(E) prostanoate (2.6);

4-cyano-2-[[2-(4-fluoro-1-naphthalenyl)-1-oxopropyl]amino]-benzenebutanoic acid (2.7) and N-{2-[4-(4,9-diethoxy-1-oxo-1,3-dihydro-2H-benzo[f]isoindol-2-yl)phenyl]acetyl}benzene sulphonamide (2.8)

In a particularly preferred embodiment of the invention, in these above mentioned uses the PDE4 inhibitor of general formula 1 is used in a daily dose of 0.01 mg to 50 mg.

In another particularly preferred embodiment of the invention in these above mentioned uses the EP4-receptor antagonist (2) is used in a daily dose of 0.001 to 100 mg/kg body weight, preferably in a daily dose of 0.01 to 50 mg/kg body weight, more preferably in a daily dose of 0.1 to 10 mg/kg body weight.

In another particularly preferred embodiment of the invention in these above mentioned uses the EP4-receptor antagonist (2) and the PDE4 inhibitor (1) are used in a ratio by weight of 1:1 to 200:1, preferably in a ratio by weight of 10:1 to 150:1, particularly preferably in a ratio by weight of 30:1 to 100:1.

In particular, the invention relates to the above mentioned uses, wherein the or at least one or more of the PDE4 inhibitor-mediated side effects in considerably reduced or totally prevented, compared with the sole administration of the PDE4 inhibitor used in the medicament combination.

In particular, the invention further relates to the use of EP4-receptor-antagonists, preferably as hereinbefore defined and according to the preferred definition, for reducing or preventing one or more PDE4 inhibitor-mediated side effects.

These PDE4 inhibitor-mediated side effects are preferably selected from loss of body weight, spleen weight loss, leukocytosis, neutrophilia, nausea, vomiting, diarrhoea and mesenteric vasculitis. These PDE4 inhibitor-mediated side effects are more preferably selected from loss of body weight, spleen weight loss, leukocytosis, neutrophilia and mesenteric vasculitis.

Synthesis Instructions

The compounds of general formula (I) may be prepared according to the following general synthesis scheme, wherein the substituents of general formulae (I), (II), (III) and (IV)

have the meanings given hereinbefore. These methods are to be understood as being an explanation of the invention without restricting it to their subject-matter.

GENERAL SYNTHESIS SCHEME

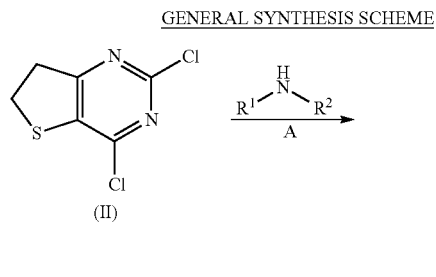

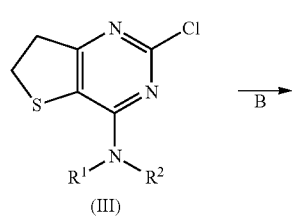

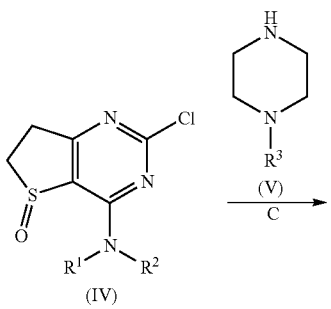

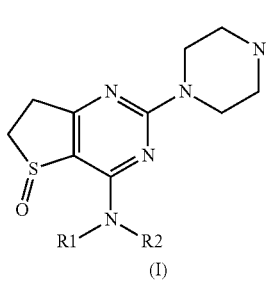

For the preparation of (II) see WO06111549

1. SYNTHESIS OF (3-FLUOROPHENYL)-[5-OXO-2-(4-THIAZOL-2-YL-PIPERAZIN-1-YL)-6,7-DIHYDRO-5H-5λ⁴-THIENO[3,2-d]PYRIMIDIN-4-YL]-AMINE (EXAMPLE 1.1)

1.1 (2-chloro-6,7-dihydrothieno[3,2-d]pyrimidin-4-yl)-(3-fluorophenyl)-amine (III-1)

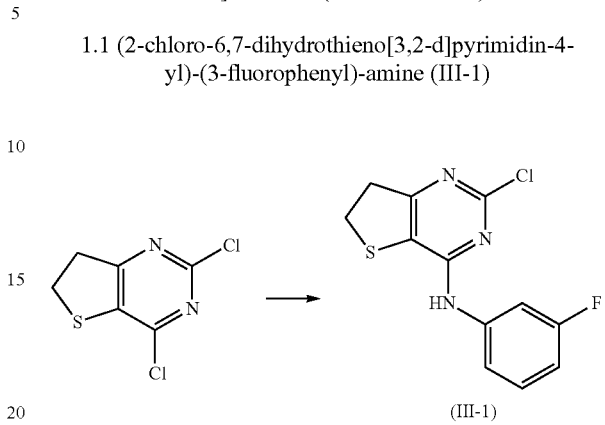

4 g (II) are placed in 15 ml dimethylformamide, then 4.5 ml diisopropylethylamine and then 2.5 ml 3-fluorophenylamine are added. The reaction mixture is heated to 120° C., until there is no further reaction, and after cooling evaporated down. The residue is mixed with water. The product is extracted with dichloromethane and purified by chromatography (silica gel, petroleum ether/ethyl acetate 80/20 to 60/40). 2.6 g (III-1) are obtained as a solid. Analytical HPLC (method A): RT=3.27 min.

1.2 2-chloro-5-oxo-6,7-dihydro-5H-5λ⁴-thieno[3,2-d]pyrimidin-4-yl)-(3-fluorophenyl)-amine (IV-1)

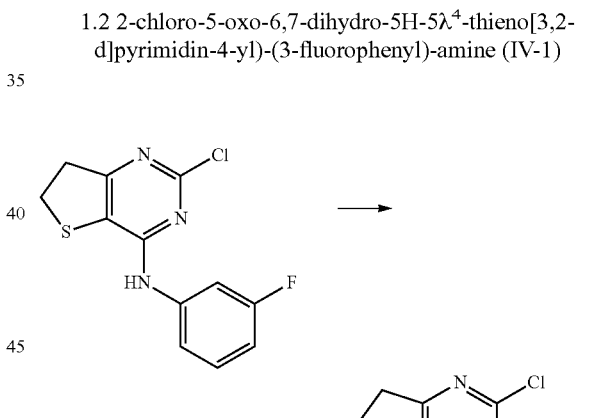

0.102 g S-(−)-1,1'-bi-2-naphthol are placed under argon in 0.5 ml chloroform, then 0.052 ml titanium(IV)isopropoxide and 0.064 ml of water are added. The reaction mixture is stirred for 45 minutes at ambient temperature. Then a suspension of 0.5 g (III-1) in 25 ml chloroform is added. The reaction mixture is cooled to −2°/−4° C. and after 20 minutes 0.323 ml tert-butylhydroperoxide 5-6 M in decane are added dropwise. The reaction mixture is stirred further at −2/−4° C. until there is no further reaction and mixed with water. The product is extracted with dichloromethane and purified by chromatography (silica gel, dichloromethane/methanol 100/0 to 95/5). 0.47 g (IV-1) are obtained as a solid. Analytical HPLC-MS (method A): RT=1.16 min.

1.3 (3-fluorophenyl)-[5-oxo-2-(4-thiazol-2-yl-piperazin-1-yl)-6,7-dihydro-5H-5λ⁴-thieno[3,2-d]pyrimidin-4-yl]-amine (Example 1.1)

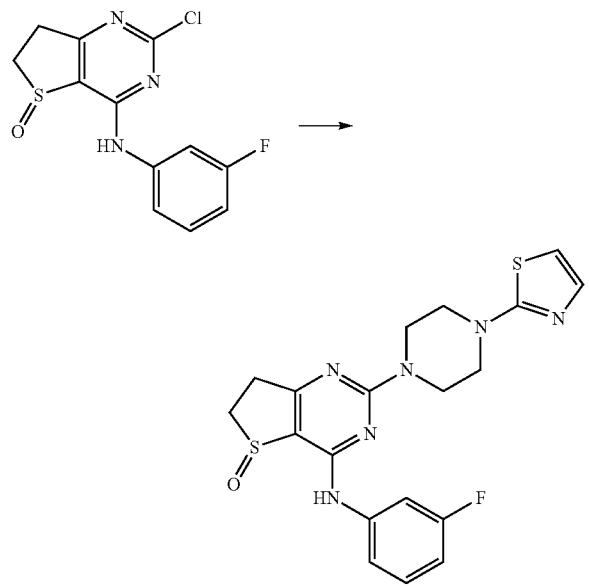

Example 1.1

0.2 g (IV-1) is placed in 3 ml dioxane, 240 μl diisopropylethylamine and 0.24 g 1-thiazol-2-yl-piperazine are added. The reaction mixture is heated to 120° C. in the microwave until there is no further reaction and mixed with water. The precipitated solid is suction filtered and purified by chromatography (silica gel, ethyl acetate/methanol 100/0 to 80/20). 0.17 g Example 1.1 are obtained as a solid. Analytical HPLC-MS (method A): RT=1.07 min.

2. SYNTHESIS OF (R)-3-METHYL-2-[5-OXO-2-(4-THIAZOL-2-YL-PIPERAZIN-1-YL)-6,7-DIHYDRO-5H-5λ⁴-THIENO[3,2-d]PYRIMIDIN-4-YLAMINO]-BUTAN-1-OL (EXAMPLE 1.2)

2.1 (R)-2-(2-chloro-6,7-dihydro-thieno[3,2-d]pyrimidin-4-ylamino)-3-methyl-butan-1-ol (III-2)

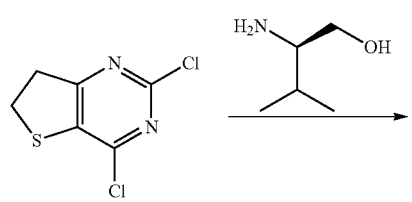

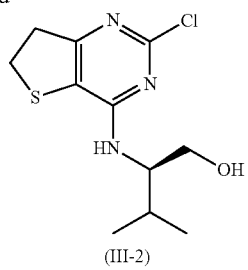

7.2 g 2,4-dichloro-6,7-dihydro-thieno[3,2-d]pyrimidine (II) are placed in 36 ml dioxane, then 18 ml diisopropylethylamine and then 6.1 g (R)-(−)-2-amino-3-methyl-1-butanol are added. The reaction mixture is heated to 100° C. until there is no further reaction and after cooling it is evaporated down. The residue is treated with petroleum ether/ethyl acetate 9:1 in the ultrasound bath and the solid is suction filtered and dried. 8.3 g (III-2) are obtained as a solid. Analytical HPLC (method A): RT=2.75 min

2.2 (R)-2-(2-chloro-5-oxo-6,7-dihydro-5H-5λ⁴-thieno[3,2-d]pyrimidin-4-ylamino)-3-methyl-butan-1-ol (IV-2)

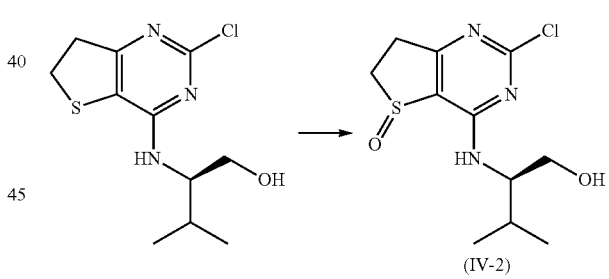

4.1 g S-(−)-1,1'-bi-2-naphthol are placed under argon in 15 ml chloroform, then 0.44 ml titanium(IV)isopropoxide and 0.54 ml of water are added. The reaction mixture is stirred for 1 hour at ambient temperature. Then a suspension of 4.1 g (III-2) in 107 ml dichloromethane is added. The reaction mixture is cooled to −2° C. and after 30 minutes 2.7 ml tert-butylhydroperoxide 5-6 M in decane are added dropwise. The reaction mixture is stirred further at −2° C. until there is no further reaction, and made basic with NH₄OH. The product is extracted with dichloromethane and purified by chromatography (silica gel, ethyl acetate/methanol 100/0 to

2.3 (R)-3-methyl-2-[5-oxo-2-(4-thiazol-2-yl-piperazin-1-yl)-6,7-dihydro-5H-5λ⁴-thieno[3,2-d]pyrimidin-4-ylamino]-butan-1-ol (Example 1.2)

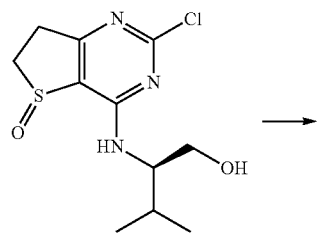

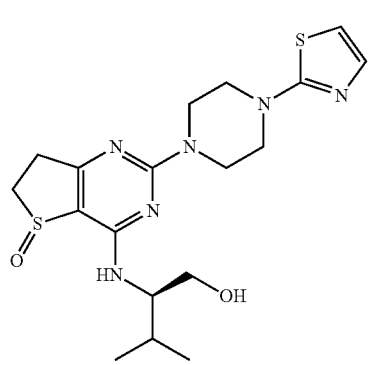

Example 1.2

Starting from 0.2 g (IV-2) and 0.245 g 1-thiazol-2-yl-piperazine 0.13 g Example 1.2 are prepared analogously to Example 1.1 (see 1.3). The reaction mixture is mixed with water and the product is extracted with dichloromethane and purified by chromatography (silica gel, dichloromethane/methanol 100/0 to 90/10). Analytical HPLC-MS (method A): RT=0.87 min.

3. SYNTHESIS OF [2-(4-BENZOXAZOL-2-YL-PIPERAZIN-1-YL)-5-OXO-6,7-DIHYDRO-5H-5λ⁴-THIENO[3,2-d]PYRIMIDIN-4-YL]-(3-FLUOROPHENYL)-AMINE (EXAMPLE 1.3)

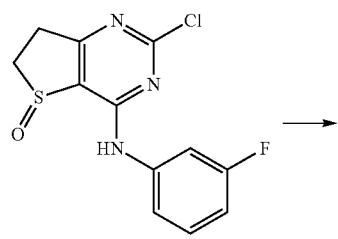

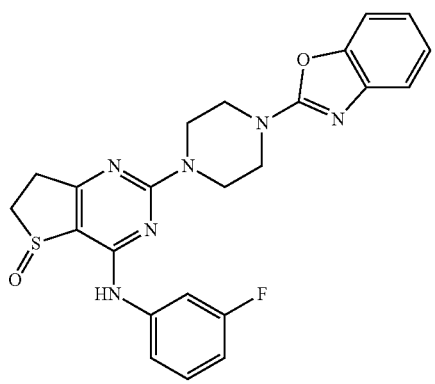

Example 1.3

Starting from 0.2 g (IV-1) (see 1.2) and 0.287 g 2-piperazin-1-yl-benzoxazole 0.31 g Example 1.3 are prepared analogously to Example 1.1 (see 1.3). The reaction mixture is mixed with water and the product is suction filtered. Analytical HPLC-MS (method A): RT=1.23 min.

4. SYNTHESIS OF [2-(4-BENZOXAZOL-2-YL-PIPERAZIN-1-YL)-5-OXO-6,7-DIHYDRO-5H-5λ⁴-THIENO[3,2-d]PYRIMIDIN-4-YL]-(TETRAHYDROPYRAN-4-YL)-AMINE (EXAMPLE 1.4)

4.1 (2-chloro-6,7-dihydrothieno[3,2-d]pyrimidin-4-yl)-(tetrahydropyran-4-yl)-amine (III-3)

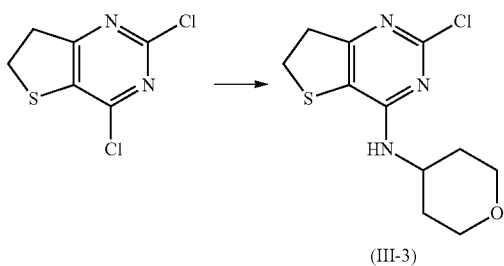 [SMILES: Clc1nc(Cl)c2c(n1)CCS2 ; Clc1nc2c(c(NC3CCOCC3)n1)SCC2 ; "(III-3)"]

(III-3)

0.68 g (II) are placed in 6 ml dioxane, then 1.72 ml diisopropylethylamine followed by 0.6 g 4-aminotetrahydropyran are added. The reaction mixture is heated to 130° C. until there is no further reaction and after cooling evaporated down. The product is treated with water in the ultrasound bath and the solid is suction filtered and dried. 0.66 g (III-3) are obtained. Analytical HPLC-MS (method A): RT=1.08 min.

4.2 (2-chloro-5-oxo-6,7-dihydro-5H-5λ⁴-thieno[3,2-d]pyrimidin-4-yl)-(tetrahydropyran-4-yl)-amine (IV-3)

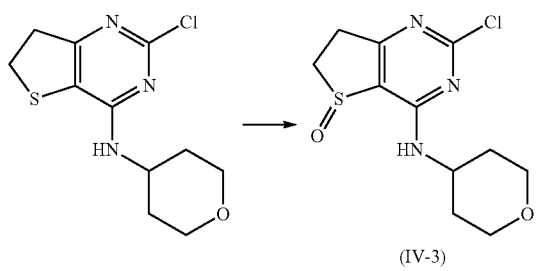 [SMILES: Clc1nc2c(c(NC3CCOCC3)n1)SCC2 ; O=S1CCc2nc(Cl)nc(NC3CCOCC3)c21 ; "(IV-3)"]

0.14 g S-(−)-1,1'-bi-2-naphthol are placed under argon in 5 ml chloroform, then 0.072 ml titanium(IV)isopropoxide and 0.087 ml of water are added. The reaction mixture is stirred for 45 minutes at ambient temperature. Then a suspension of 0.66 g (III-3) in 25 ml chloroform is added. The reaction mixture is cooled to −10° C. and after 60 minutes 0.444 ml tert-butylhydroperoxide 5-6 M in decane are added dropwise. The reaction mixture is stirred further at −10 to −4° C., until there is no further reaction, and mixed with water. The product is extracted with dichloromethane and purified by chromatography (silica gel, ethyl acetate/methanol 100/0 to 80/20). 0.42 g (IV-3) are obtained as a solid. Analytical HPLC-MS (method A): RT=0.94 min.

4.3 [2-(4-benzoxazol-2-yl-piperazin-1-yl)-5-oxo-6,7-dihydro-5H-5λ⁴-thieno[3,2-d]pyrimidin-4-yl]-(tetrahydropyran-4-yl)-amine (Example 1.4)

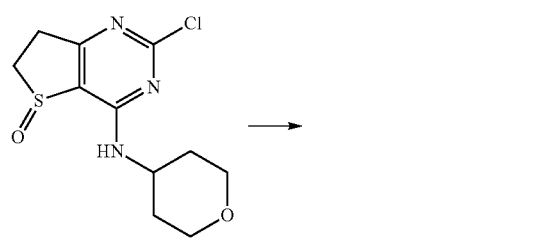

Example 1.4

Starting from 0.2 g (IV-3) and 0.315 g 2-piperazin-1-yl-benzoxazole 0.3 g Example 1.4 are prepared and worked up analogously to Example 1.3 (see 3.). Analytical HPLC-MS (method A): RT=1.04 min.

5. SYNTHESIS OF (R)-2-{2-[4-(6-CHLOROPYRIDAZIN-3-YL)-PIPERAZIN-1-YL]-5-OXO-6,7-DIHYDRO-5H-5λ⁴-THIENO[3,2-d]PYRIMIDIN-4-YLAMINO}-3-METHYLBUTAN-1-OL (EXAMPLE 1.5)

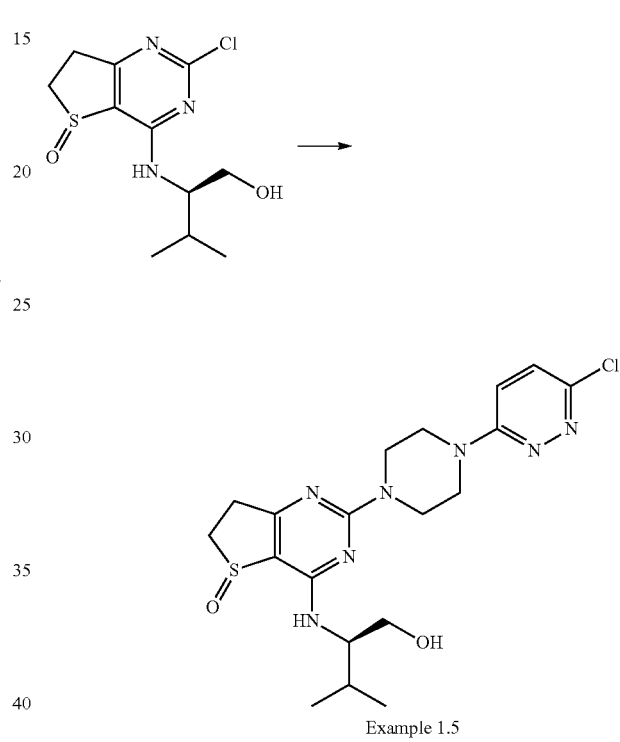

Example 1.5

Starting from 0.2 g (IV-2) (see 2.2) and 0.287 g 3-chloro-6-piperazin-1-yl-pyridazine, 0.257 g of Example 1.5 are prepared and worked up analogously to Example 1.3 (see 3.). Analytical HPLC-MS (method A): RT=0.98 min.

6. SYNTHESIS OF {2-[4-(6-CHLOROPYRIDAZIN-3-YL)-PIPERAZIN-1-YL]-5-OXO-6,7-DIHYDRO-5H-5λ⁴-THIENO[3,2-d]PYRIMIDIN-4-YL}-(3-FLUOROPHENYL)-AMINE (EXAMPLE 1.6)

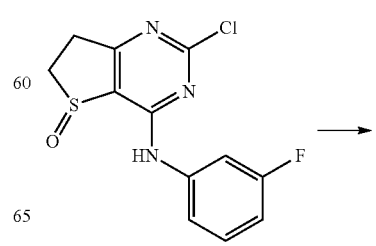

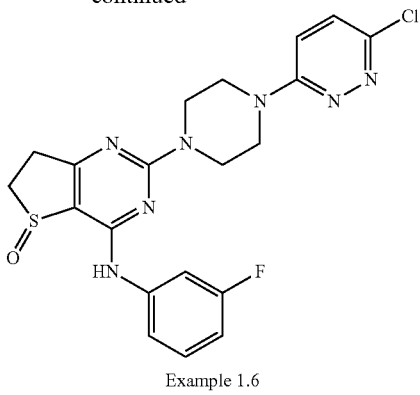

Example 1.6

Starting from 0.2 g (IV-1) (see 1.2) and 0.28 g 3-chloro-6-piperazin-1-yl-pyridazine, 0.31 g of Example 1.6 are prepared analogously to Example 1.3 (see 3.). Analytical HPLC-MS (method A): RT=1.12 min.

7. SYNTHESIS OF (R)-2-[2-(4-BENZOXAZOL-2-YL-PIPERAZIN-1-YL)-5-OXO-6,7-DIHYDRO-5H-5λ⁴-THIENO[3,2-d]PYRIMIDIN-4-YLAMINO]-3-METHYLBUTAN-1-OL (EXAMPLE 1.7)

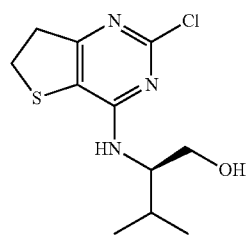

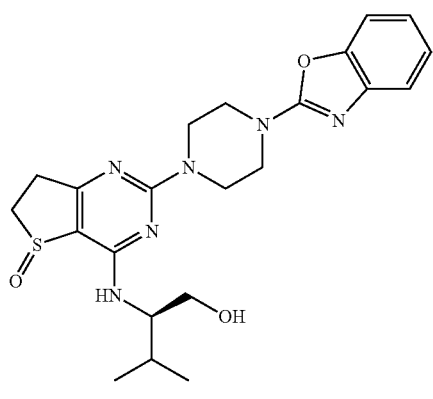

Example 1.7

Starting from 0.2 g (IV-2) (see 2.2) and 0.313 g 2-piperazin-1-yl-benzoxazole 0.16 g Example 1.7 are prepared analogously to Example 1.1 (see 1.3). The reaction mixture is mixed with water and the product is extracted with dichloromethane and purified by chromatography (silica gel, ethyl acetate/methanol 100/0 to 80/20). Analytical HPLC-MS (method A): RT=1.06 min.

8. SYNTHESIS OF (1-{2-[4-(5-CHLOROPYRIDIN-2-YL)-PIPERAZIN-1-YL]-5-OXO-6,7-DIHYDRO-5H-5λ⁴-THIENO[3,2-d]PYRIMIDIN-4-YLAMINO}-CYCLOPROPYL)-METHANOL (EXAMPLE 1.8)

8.1 tert-butyl (1-hydroxymethylcyclopropyl)-carbamidate

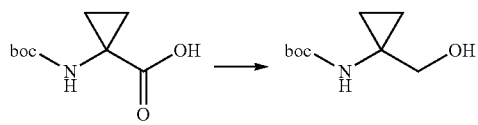

1 g 1-(BOC-amino)-cyclopropanecarboxylic acid is dissolved in 20 ml dimethoxyethane and cooled to −70° C. Then 0.65 ml N-methylmorpholine are added and 0.71 ml isobutylchloroformate in 5 ml dimethoxyethan are added dropwise. The reaction mixture is heated to −5° C. The precipitate is suction filtered. The eluate is cooled to −15° C. and 0.303 g sodium borohydride are slowly added. The reaction mixture is then stirred for 30 minutes at ambient temperature, mixed with water and the product is extracted with dichloromethane. The organic phase is dried and evaporated to dryness. 1.04 g product are obtained as a solid. $^1$H NMR (400 MHz, DMSO): 1.36 (9H, s); 0.61 (2H, t); 0.52 (2H, t).

8.2 1-aminocyclopropanemethanol

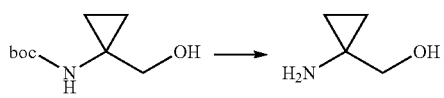

1.04 g tert-butyl (1-hydroxymethylcyclopropyl)-carbamidate are placed in 5 ml dioxane. 2.5 ml of HCl in dioxane (4 mol/l) are added dropwise. The reaction mixture is stirred for 15 h at ambient temperature. The solvent is evaporated down by half and the precipitated solid is suction filtered. 0.5 g product are obtained as the hydrochloride. $^1$H NMR (400 MHz, DMSO): 5.27 (1H, t); 0.91 (2H, t); 0.71 (2H, t).

8.3 [1-(2-chloro-6,7-dihydrothieno[3,2-d]pyrimidin-4-ylamino)-cyclopropyl]-methanol (III-4)

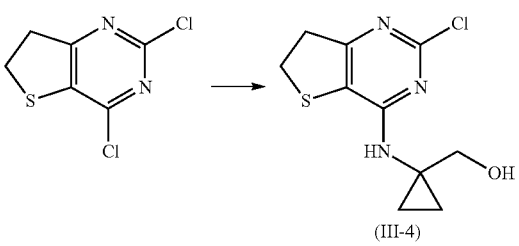

(III-4)

1.4 g (II) are placed in 10 ml dioxane, first 3.6 ml diisopropylethylamine, then 1 g of 1-aminocyclopropanmethanol (see 8.2) are added. The reaction mixture is heated to 160° C. until there is no further reaction and after cooling evaporated down.

The residue is treated with cyclohexane/ethyl acetate (8:2) in the ultrasound bath and the solid is suction filtered and dried. 1.24 g (III-4) are obtained as a solid. Analytical HPLC-MS (method A): RT=1.01 min.

8.4 [1-(2-chloro-5-oxo-6,7-dihydro-5H-5λ⁴-thieno[3,2-d]pyrimidin-4-ylamino)-cyclopropyl]-methanol (IV-4)

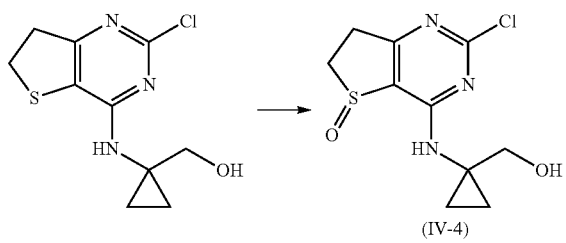

(IV-4)

0.28 g S-(−)-1,1'-bi-2-naphthol are placed in 20 ml chloroform under argon, then 0.14 ml titanium(IV)isopropoxide and 0.17 ml of water are added. The reaction mixture is stirred for 1 hour at ambient temperature. Then a suspension of 1.2 g (III-4) in 40 ml dichloromethane and 2 ml of methanol is added. The reaction mixture is cooled to −5° C. and after 30 minutes 0.91 ml tert-butylhydroperoxide 5-6 M in decane are added dropwise. The reaction mixture is stirred further at −5° C. until there is no further reaction, and made basic with NH₄OH. The aqueous phase is washed with dichloromethane and freeze-dried. 1 g (IV-4) is obtained as a solid. Analytical HPLC-MS (method A) RT=0.85 min.

8.5 (1-{2-[4-(5-chloropyridin-2-yl)-piperazin-1-yl]-5-oxo-6,7-dihydro-5H-5λ⁴-thieno[3,2-d]pyrimidin-4-ylamino}-cyclopropyl)-methanol (Example 1.8)

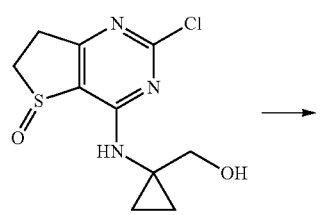

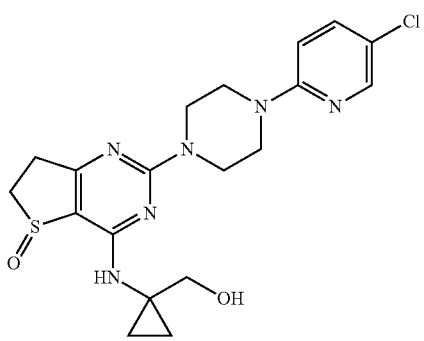

Example 1.8

0.1 g (IV-4) is placed in 3 ml N-methyl-2-pyrrolidone, then 182 μl diisopropylethylamine and 0.08 g 1-(5-chloropyridin-2-yl)-piperazine are added. The reaction mixture is heated to 120° C. in the microwave until there is no further reaction. The product is purified by chromatography (preparative HPLC, method A). Analytical HPLC-MS (method B): RT=1.09 min.

9. SYNTHESIS OF {2-[4-(5-CHLOROPYRIDIN-2-YL)-PIPERAZIN-1-YL]-5-OXO-6,7-DIHYDRO-5H-5λ⁴-THIENO[3,2-d]PYRIMIDIN-4-YL}-(TETRAHYDROPYRAN-4-YL)-AMINE (EXAMPLE 1.9)

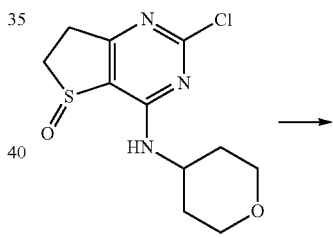

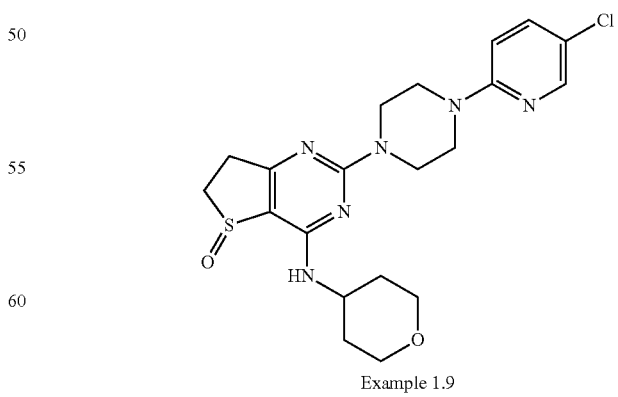

Example 1.9

Starting from 0.11 g (IV-3) (see 4.2) and 0.083 g 1-(5-chloropyridin-2-yl)-piperazine, 0.14 g of Example 1.9 are prepared and purified analogously to Example 1.8 (see 8.5). Analytical HPLC-MS (method B): RT=1.14 min.

10. SYNTHESIS OF {2-[4-(3-DIMETHYLAMI-NOPYRIDAZIN-4-YL)-PIPERAZIN-1-YL]-5-OXO-6,7-DIHYDRO-5H-5λ⁴-THIENO[3,2-d]PYRIMIDIN-4-YL}-(3-FLUOROPHENYL)-AMINE (EXAMPLE 1.10)

10.1 3,4,6-trichloropyridazine

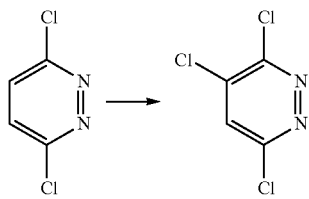 [SMILES: Clc1ccc(Cl)nn1 ; Clc1cc(Cl)c(Cl)nn1]

44 g 3,6-dichloropyridazine and 22 g aluminium trichloride are heated to 140° C. At this temperature 10.6 l chlorine are piped into the reaction mixture over 4 hours. After cooling the product is extracted with toluene, washed with a 10% sodium chloride solution and distilled (bp=127-129° C.). 44.1 g of product are obtained.

10.2 3,6-dichloro-4-piperazin-1-yl-pyridazine

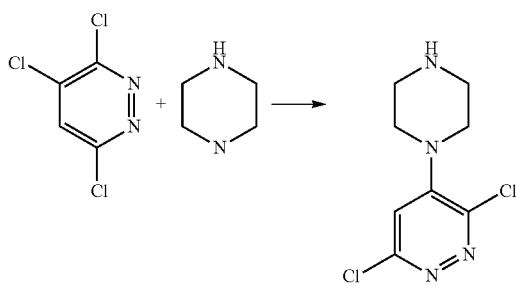

18 g 3,4,6-trichloro-pyridazine and 34 g piperazine are suspended in 100 ml of ethanol and stirred for 30 minutes at ambient temperature. The precipitated solid is suction filtered. 500 ml of water are added to the mother liquor and the precipitated product is suction filtered. 14 g product are obtained as a solid. M.p=111-115° C.

10.3 (6-chloro-4-piperazin-1-yl-pyridazin-3-yl)-dimethylamine

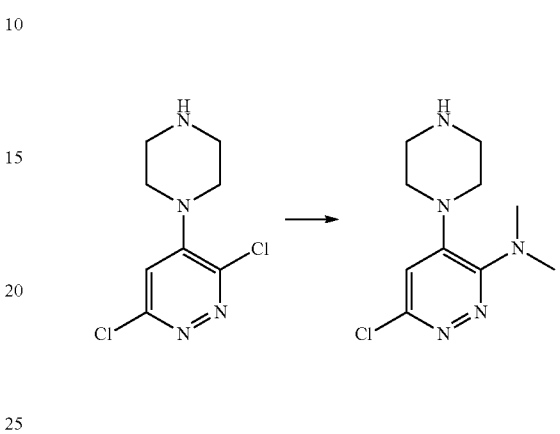

23 g 3,6-dichloro-4-piperazin-1-yl-pyridazine and 45 g dimethylamine are suspended in 200 ml of methanol and the mixture is autoclaved for 4 hours at 100° C. The reaction mixture is evaporated to dryness and the product is extracted with chloroform and washed with sodium hydroxide solution. The hydrochloride is precipitated with an ethereal HCl solution. 27 g product are obtained. M.p.=291° C.

10.4 dimethyl-(4-piperazin-1-yl-pyridazin-3-yl)-amine (V-1)

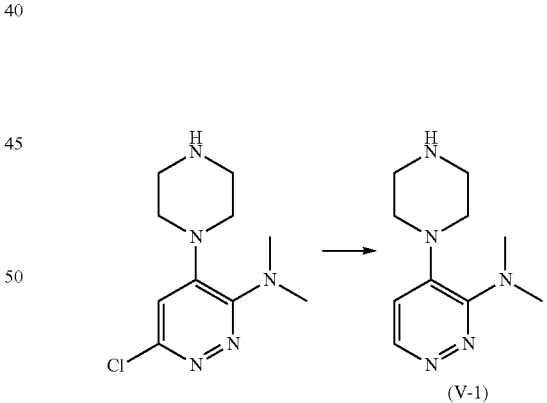

9.4 g (6-chloro-4-piperazin-1-yl-pyridazin-3-yl)-dimethylamine hydrochloride and 7.3 g sodium acetate are suspended in 150 ml of methanol and hydrogenated with 1 g Pd/C 10% at ambient temperature. The catalyst is suction filtered, the filtrate is evaporated to dryness and the product is extracted with chloroform and washed with sodium hydroxide solution. The hydrochloride is precipitated with an ethereal HCl solution. 7 g (V-1) are obtained. M.p=335° C.

10.5 {2-[4-(3-dimethylaminopyridazin-4-yl)-piperazin-1-yl]-5-oxo-6,7-dihydro-5H-5λ⁴-thieno[3,2-d]pyrimidin-4-yl}-(3-fluorophenyl)-amine (Example 1.10)

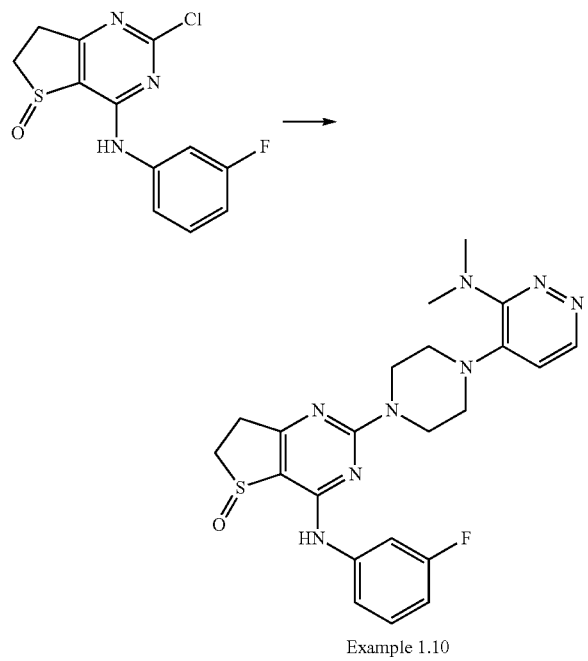

Example 1.10

(IV-1) (see 1.2) (0.1 mmol) is placed in 750 μl N-methyl-2-pyrrolidone (NMP) and 50 μl diisopropylethylamine, mixed with a solution of (V-1) (0.1 mmol) in 400 μl NMP and heated to 120° C. for 30 min in the microwave. Then 600 μL DMF are added, the reaction solution is purified by chromatography (preparative HPLC-MS, method A) and the product fractions are freeze-dried. Example 1.10 is obtained as the trifluoroacetate. Analytical HPLC-MS (method C): RT=1.61 min.

11. SYNTHESIS OF 6-CHLORO-4-{4-[4-(3-FLUOROPHENYLAMINO)-5-OXO-6,7-DIHYDRO-5H-5λ⁴-THIENO[3,2-d]PYRIMIDIN-2-YL]-PIPERAZIN-1-YL}-PYRIDAZIN-3-OL (EXAMPLE 1.11)

11.1 (6-chloro-4-piperazin-1-yl-pyridazin-3-yloxy)-ethanol

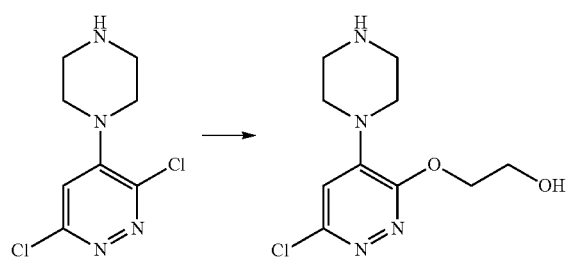 [SMILES: Clc1cc(N2CCNCC2)c(Cl)nn1 ; OCCOc1nnc(Cl)cc1N1CCNCC1]

23 g 3,6-dichloro-4-piperazin-1-yl-pyridazine (see 10.2) are suspended in 100 ml ethyleneglycol and added dropwise to a suspension of 2.3 g sodium in 100 ml ethyleneglycol. The reaction mixture is heated to 100° C. for 3 hours and evaporated to dryness. The residue is suspended in acetonitrile and the solid is suction filtered. The mother liquor is evaporated to dryness, the product is extracted with dichloromethane and washed with conc. NaOH. The product is suspended in ethanol and precipitated as the fumarate with fumaric acid. 13 g product are obtained. M.p=179° C.

11.2 6-chloro-4-piperazin-1-yl-pyridazin-3-ol (V-2)

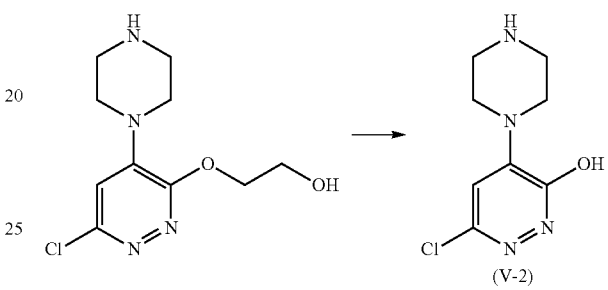

(V-2)

15 g (6-chloro-4-piperazin-1-yl-pyridazin-3-yloxy)-ethanol fumarate are suspended in 90 ml hydrogen bromide (48%). The reaction mixture is stirred for 1 hour at reflux temperature and evaporated to dryness. 19 g product are obtained as the hydrobromide. M.p=35° C.

11.3 6-chloro-4-{4-[4-(3-fluorophenylamino)-5-oxo-6,7-dihydro-5H-5λ⁴-thieno[3,2-d]pyrimidin-2-yl]-piperazin-1-yl}-pyridazin-3-ol (Example 1.11)

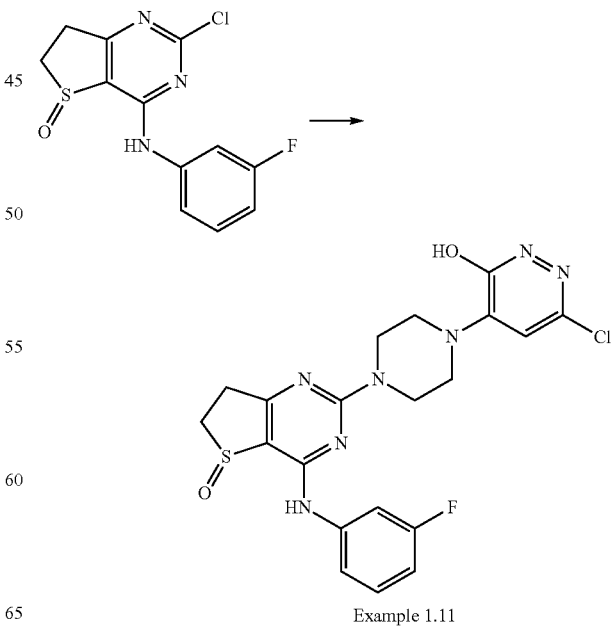

Example 1.11

Starting from (IV-1) (see 1.2) and (V-2) Example 1.11 is prepared and purified analogously to Example 1.10 (see 10.5). Analytical HPLC-MS (method C): RT=1.86 min.

12. SYNTHESIS OF (2-{4-[6-(2-ETHOXY-ETHOXY)-PYRIDAZIN-3-YL]-PIPERAZIN-1-YL}-5-OXO-6,7-DIHYDRO-5H-5λ⁴-THIENO[3,2-d]PYRIMIDIN-4-YL)-(3-FLUOROPHENYL)-AMINE (EXAMPLE 1.12)

12.1 3-ethoxyethoxy-6-piperazin-1-yl-pyridazine (V-3)

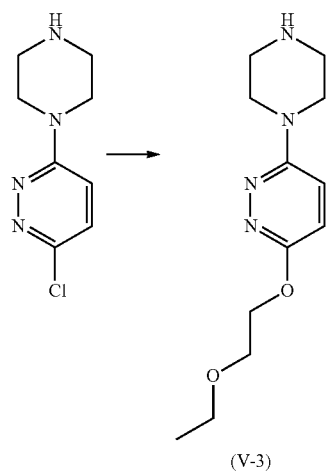

18 g 3-chloro-6-piperazin-1-yl-pyridazine and 30 g potassium hydroxide in 30 ml of water are suspended in 180 ml ethylglycol and stirred for 4 hours at reflux temperature. The reaction mixture is evaporated to dryness. The product is extracted with diethyl ether, washed with a concentrated potassium carbonate solution and distilled (bp=190° C.). 18 g (V-3) are obtained.

12.2 (2-{4-[6-(2-ethoxyethoxy)-pyridazin-3-yl]-piperazin-1-yl}-5-oxo-6,7-dihydro-5H-5λ⁴-thieno[3,2-d]pyrimidin-4-yl)-(3-fluorophenyl)-amine (Example 1.12)

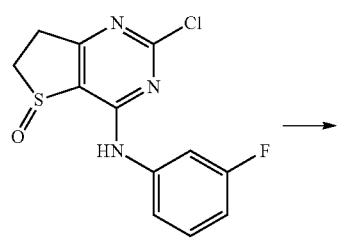

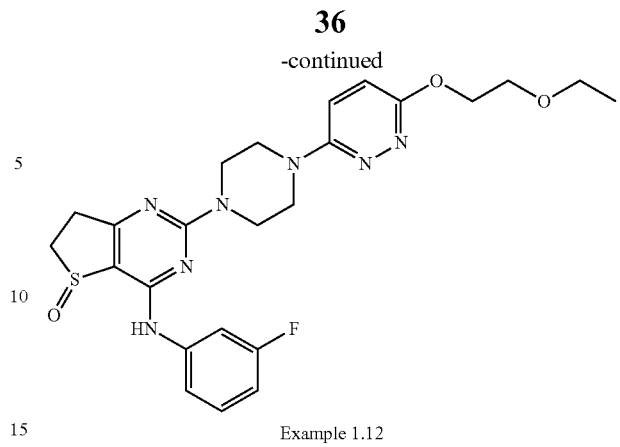

Example 1.12

Starting from (IV-1) (see 1.2) and (V-3) Example 1.12 is prepared and purified as the trifluoroacetate analogously to Example 1.10 (see 10.5). Analytical HPLC-MS (method C): Rt=1.66 min.

13. SYNTHESIS OF (3-FLUOROPHENYL)-[5-OXO-2-(4-PYRIDAZIN-4-YL-PIPERAZIN-1-YL)-6,7-DIHYDRO-5H-5λ⁴-THIENO[3,2-d]PYRIMIDIN-4-YL]-AMINE (EXAMPLE 1.13)

13.1 4-piperazin-1-yl-pyridazine (V-4)

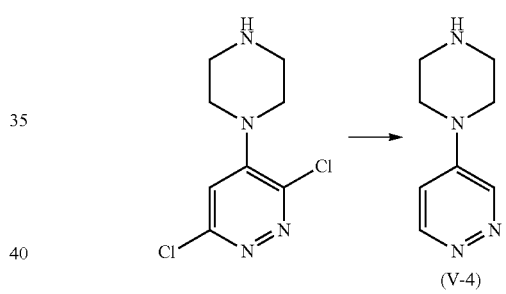

9.3 g of 3,6-dichloro-4-piperazin-1-yl-pyridazine (see 10.2) and 6.5 g sodium acetate are suspended in 100 ml of methanol and hydrogenated with 1 g Pd/C 10% and ambient temperature. The catalyst is suction filtered and the filtrate evaporated to dryness. The product is extracted with chloroform, washed with sodium hydroxide solution and precipitated as the hydrochloride with an ethereal HCl solution. 8.6 g of (V-4) are obtained. M.p>300° C.

13.2 (3-fluorophenyl)-[5-oxo-2-(4-pyridazin-4-yl-piperazin-1-yl)-6,7-dihydro-5H-5λ⁴ thieno[3,2-d]pyrimidin-4-yl]-amine (Example 1.13)

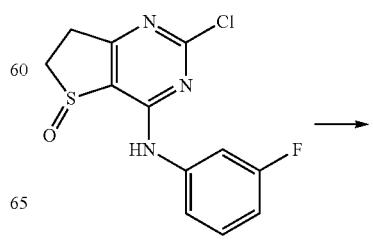

-continued

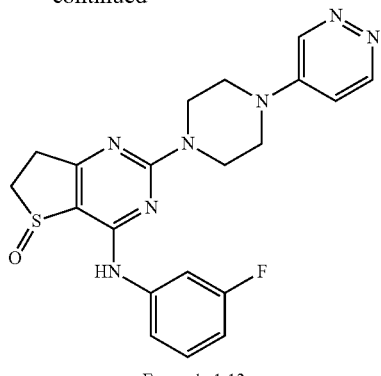
Example 1.13

Starting from (IV-1) (see 1.2) and (V-4) Example 1.13 is prepared and purified as the trifluoroacetate analogously to Example 1.10 (see 10.5). Analytical HPLC-MS (method C): RT=1.54 min.

14. SYNTHESIS OF (R)-2-{2-[4-(4-METHOXY-1-METHYL-1H-BENZIMIDAZOL-2-YL)-PIPER-AZIN-1-YL]-5-OXO-6,7-DIHYDRO-5H-5$\lambda^4$-THIENO[3,2-d]PYRIMIDIN-4-YLAMINO}-3-METHYLBUTAN-1-OL TRIFLUOROACETATE (EXAMPLE 1.14)

14.1 tert-butyl (3-methoxy-2-nitrophenyl)-carbamidate

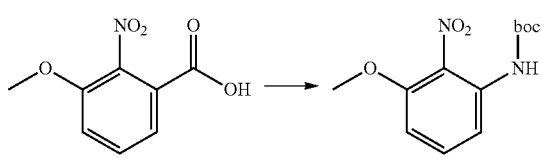

10 g 3-methoxy-2-nitrobenzoic acid and 7 ml triethylamine are placed in 100 ml tert-butanol and 11 ml diphenylphosphorylazide are added dropwise. The reaction mixture is then stirred for 6 hours at reflux temperature and evaporated to dryness. The product is extracted with ethyl acetate, washed with a 10% citric acid, a saturated sodium hydrogen carbonate and a saturated sodium chloride solution. 12.4 g product are obtained as a solid. M.p=90° C.

14.2 tert-butyl (3-methoxy-2-nitrophenyl)-methyl-carbamidate

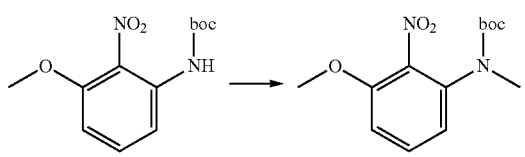

12.2 g tert-butyl (3-methoxy-2-nitrophenyl)-methyl-carbamidate are placed in 80 ml dimethylformamide and cooled at 0° C. 2.4 g sodium hydride (50% in mineral oil) are slowly added. The reaction mixture is stirred for 30 minutes at 0° C. Then 3.1 ml methyl iodide are added dropwise. The reaction mixture is stirred for 2 hours at ambient temperature and mixed with water. The product is extracted with ethyl acetate. 12.5 g product are obtained as an oil.

14.3 (3-methoxy-2-nitrophenyl)-methylamine

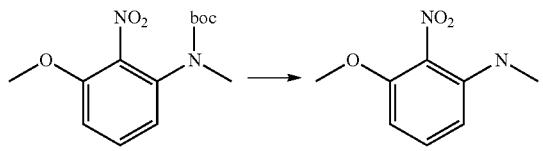

12.5 g tert-butyl (3-methoxy-2-nitrophenyl)-methyl-carbamidate and 78 ml hydrochloric acid (4 M) are suspended in 300 ml of ethyl acetate and heated to 60° C. for 5 hours. The reaction mixture is evaporated to dryness, the residue is combined with a saturated sodium hydrogen carbonate solution and the product is extracted with ethyl acetate. 7.5 g product are obtained as a solid. M.p=58-59° C.

14.4 3-methoxy-$N^1$-methylbenzene-1,2-diamine

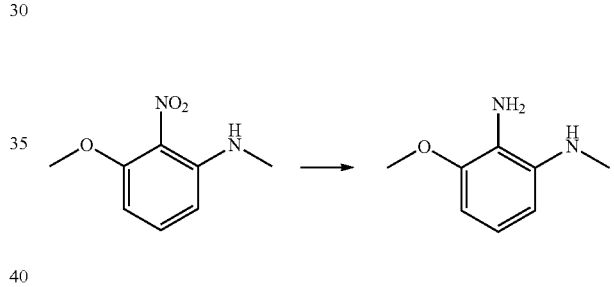

7.4 g (3-methoxy-2-nitrophenyl)-methylamine are suspended in 150 ml of ethyl acetate and hydrogenated with 1 g Pd/C 10% at a pressure of 50 psi and ambient temperature. After 4.5 hours the catalyst is suction filtered and the filtrate is evaporated to dryness. 5.9 g of the product are obtained as an oil.

14.5 4-methoxy-1-methyl-1,3-dihydrobenzimidazol-2-one

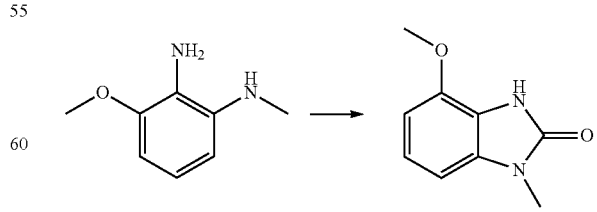

5.9 g 3-methoxy-N1-methylbenzene-1,2-diamine are suspended in 70 ml of tetrahydrofuran and 6.3 g N,N'-carbonyldiimidazole are added. The reaction mixture is stirred for 5 hours at ambient temperature, mixed with water and the product is extracted with ethyl acetate. 3.9 g product are obtained as a solid.

14.6 2-chloro-4-methoxy-1-methyl-1H-benzimidazole

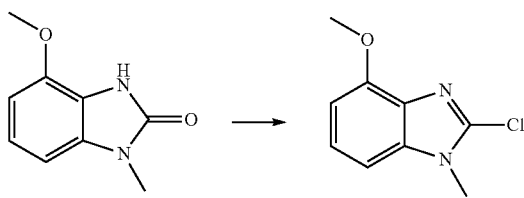

3.7 g 4-methoxy-1-methyl-1,3-dihydrobenzimidazol-2-one are suspended in 15 ml phosphorus oxychloride. The reaction mixture is stirred for 3 hours at reflux temperature, slowly combined with ice water and made alkaline with conc. ammonia. The precipitated product is suction filtered. 3.6 g product are obtained as a solid. M.p=118-119° C.

14.7 4-methoxy-1-methyl-2-piperazin-1-yl-1-benzimidazole (V-5)

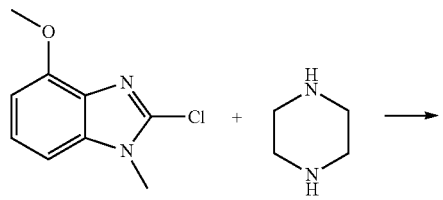

2 g 2-chloro-4-methoxy-1-methyl-1H-benzimidazole and 4.4 g piperazine are suspended in 20 ml n-butanol and stirred for 5 hours at reflux temperature. The reaction mixture is evaporated to dryness and the product is purified by chromatography (silica gel, dichloromethane/methanol 10:1). 1.6 g (V-5) are obtained as a solid. M.p=147° C.

14.8 (R)-2-{2-[4-(4-methoxy-1-methyl-1H-benzimidazol-2-yl)-piperazin-1-yl]-5-oxo-6,7-dihydro-5H-5λ⁴-thieno[3,2-d]pyrimidin-4-ylamino}-3-methylbutan-1-ol (Example 1.14)

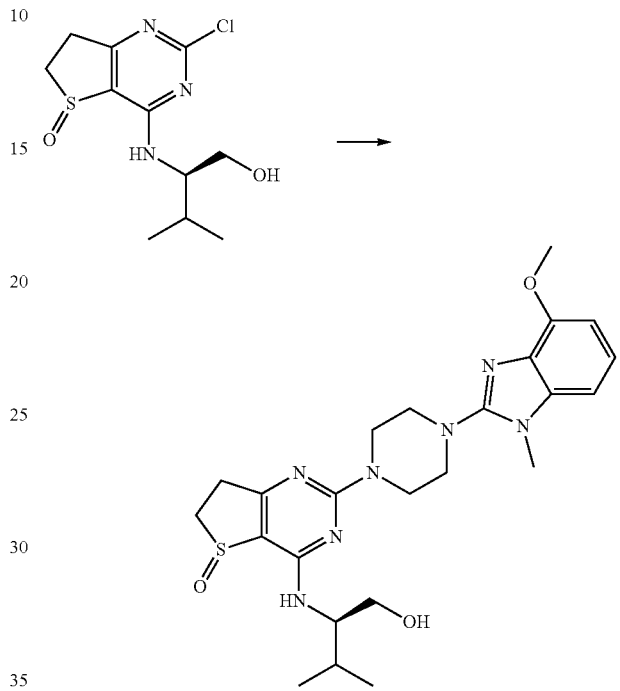

Example 1.14

Starting from (IV-2) (see 2.2) and (V-5) Example 1.14 is prepared and purified as the trifluoroacetate analogously to Example 1.10 (see 10.5). Analytical HPLC-MS (method C): RT=1.5 min.

15. SYNTHESIS OF (R)-2-{2-[4-(7-ETHYL-6,7,8,9-TETRAHYDRO-5H-PYRAZINO[2,3-d]AZEPIN-2-YL)-PIPERAZIN-1-YL]-5-OXO-6,7-DIHYDRO-5H-5λ⁴-THIENO[3,2-d]PYRIMIDIN-4-YLAMINO}-3-METHYLBUTAN-1-OL (EXAMPLE 1.15)

15.1 2-chloro-7-ethyl-6,7,8,9-tetrahydro-5H-pyrazino[2,3-d]azepine

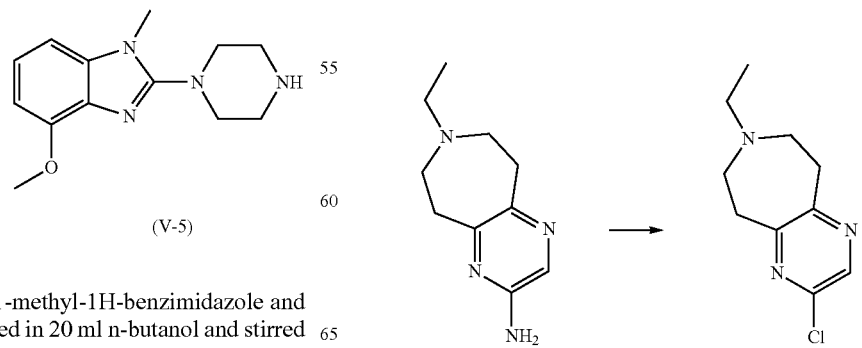

26.5 g of 7-ethyl-6,7,8,9-tetrahydro-5H-pyrazino[2,3-d]azepin-2-ylamine (U.S. Pat. No. 4,409,220) are suspended in 130 ml conc. hydrochloric acid, mixed with 0.1 g copper(I) bromide and cooled to −5° C. A suspension of 11 g sodium nitrite in 14 ml of water is slowly added dropwise. The reaction mixture is stirred for 15 hours at ambient temperature and evaporated almost to dryness. The residue is slowly added to ice water and potassium carbonate. The product is extracted with dichloromethane and precipitated as the hydrochloride with an ethereal HCl solution. 14.3 g product are obtained. M.p=258-262° C.

15.2 7-ethyl-2-piperazin-1-yl-6,7,8,9-tetrahydro-5H-pyrazino[2,3-d]azepine (V-6)

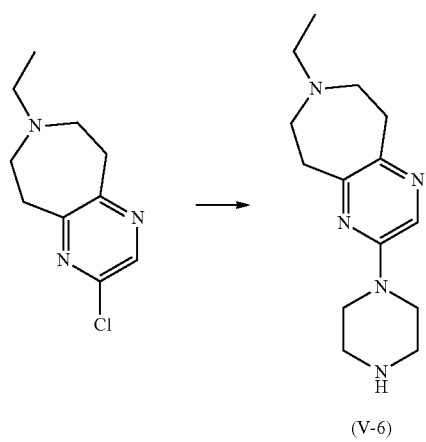 [SMILES: CCN1CCc2ncc(Cl)nc2CC1 ; CCN1CCc2ncc(N3CCNCC3)nc2CC1 ; "(V-6)"]

(V-6)

3 g 2-chloro-7-ethyl-6,7,8,9-tetrahydro-5H-pyrazino[2,3-d]azepine are combined with 23.3 g piperazine and heated to 145° C. for 5 hours. Excess piperazine is distilled off and the residue is treated with dichloromethane and methanol. Precipitated product is suction filtered and purified by chromatography (Alox, dioxane/toluene/methanol/NH₄OH 50/20/20/2). 1.95 g product are obtained.

15.3 (R)-2-{2-[4-(7-ethyl-6,7,8,9-tetrahydro-5H-pyrazino[2,3-d]azepin-2-yl)-piperazin-1-yl]-5-oxo-6,7-dihydro-5H-5λ⁴-thieno[3,2-d]pyrimidin-4-ylamino}-3-methylbutan-1-ol (Example 1.15)

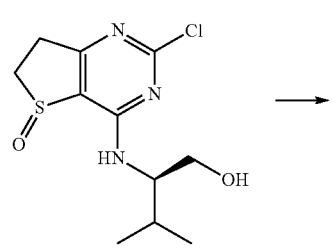

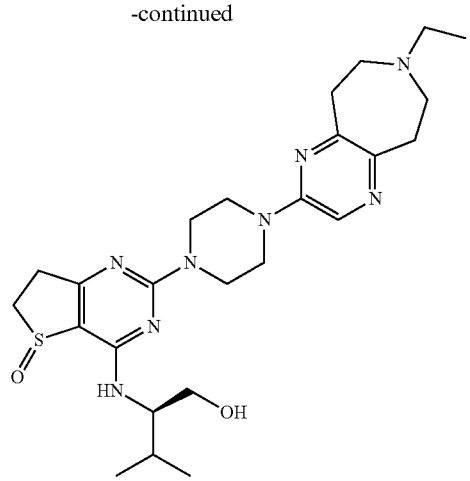

Example 1.15

Starting from (IV-2) (see 2.2) and (V-6) Example 1.15 is prepared and purified as the trifluoroacetate analogously to Example 1.10 (see 10.5). Analytical HPLC-MS (method C): RT=1.38 min.

16. SYNTHESIS OF (R)-3-METHYL-2-[5-OXO-2-(4-PYRIMIDIN-4-YL-PIPERAZIN-1-YL)-6,7-DIHYDRO-5H-5λ⁴-THIENO[3,2-d]PYRIMIDIN-4-YLAMINO]-BUTAN-1-OL (EXAMPLE 1.16)

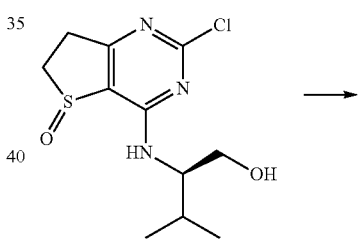

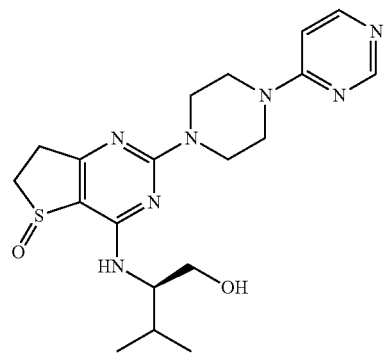

Example 1.16

Starting from (IV-2) (see 2.2) and 4-piperazin-1-yl-pyrimidine (J. Org. Chem. 1953, 1484) Example 1.16 is prepared and purified as the trifluoroacetate analogously to Example 1.10 (see 10.5). Analytical HPLC-MS (method C): RT=1.31 min.

17. SYNTHESIS OF 4-{4-[4-((R)-1-HYDROXYMETHYL-2-METHYLPROPYLAMINO)-5-OXO-6,7-DIHYDRO-5H-5λ⁴-THIENO[3,2-d]PYRIMIDIN-2-YL]-PIPERAZIN-1-YL}-PYRIDIN-2-OL (EXAMPLE 1.17)

17.1 4-(1-oxypyridin-4-yl)-piperazine-1-BOC

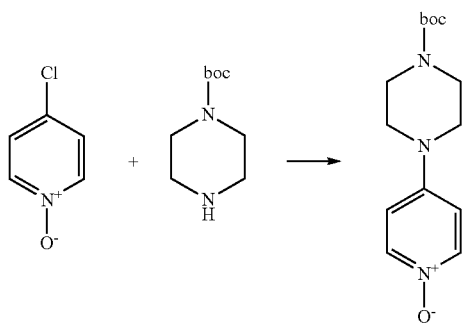

3 g 4-chloropyridine-N-oxide and 13.2 g piperazine-1-BOC are heated to 90° C. for 4 hours. The product is purified by chromatography (silica gel, dichloromethane/methanol/ammonia 90/10/1). 2.9 g product are obtained as a solid.

17.2 4-(2-hydroxypyridin-4-yl)-piperazine-1-BOC

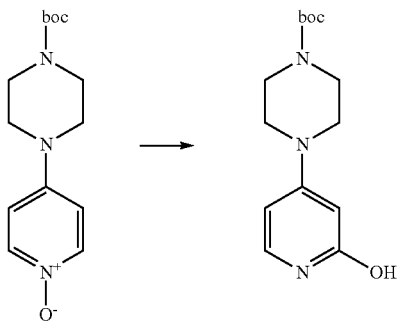

1.75 g 4-(1-oxypyridin-4-yl)-piperazine-1-BOC are suspended in 15 ml acetic anhydride and heated to 150° C. for 24 h. The reaction mixture is evaporated to dryness and the product is purified by chromatography (silica gel, ethyl acetate/methanol/ammonia 95/5/0.5). 0.51 g product are obtained as a solid 17.3 4-piperazin-1-yl-pyridin-2-ol (V-7)

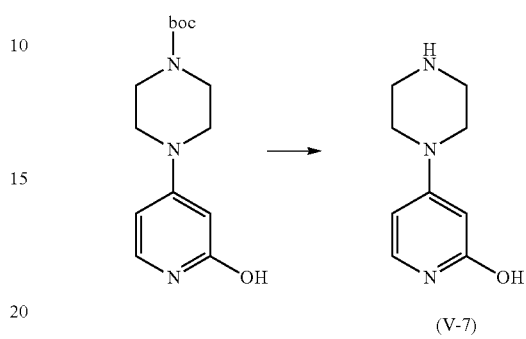

0.51 g 4-(2-hydroxypyridin-4-yl)-piperazin-1-BOC and 2 ml trifluoroacetic acid are suspended in 15 ml dichloromethane and stirred for 2 hours at ambient temperature. The reaction mixture is evaporated to dryness. 1 g (V-7) are obtained as an oil. ¹H NMR (400 MHz, DMSO): 7.30 (1H, d); 5.99 (1H, dd); 5.34 (1H, d).

17.4 4-{4-[4-((R)-1-hydroxymethyl-2-methylpropylamino)-5-oxo-6,7-dihydro-5H-5λ⁴-thieno[3,2-d]pyrimidin-2-yl]-piperazin-1-yl}-pyridin-2-ol (Example 1.17)

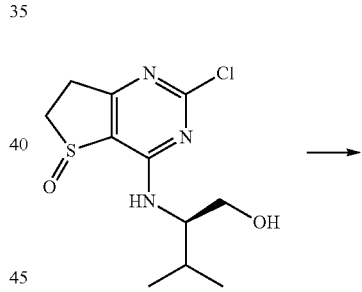

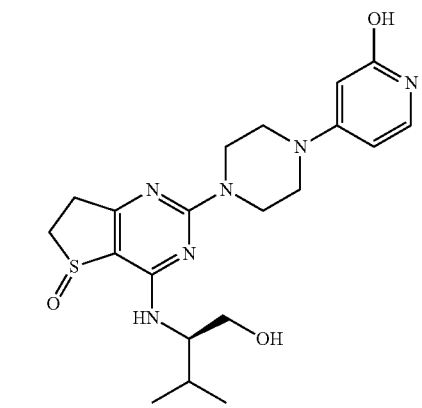

Example 1.17

Starting from (IV-2) (see 2.2) and (V-7) Example 1.17 is prepared and purified analogously to Example 1.10 (see 10.5). Analytical HPLC-MS (method C): RT=1.37 min.

18. SYNTHESIS OF (R)-3-METHYL-2-[5-OXO-2-(4-PYRIDIN-4-YL-PIPERAZIN-1-YL)-6,7-DIHYDRO-5H-5λ⁴-THIENO[3,2-d]PYRIMIDIN-4-YLAMINO]-BUTAN-1-OL TRIFLUOROACETATE (EXAMPLE 1.18)

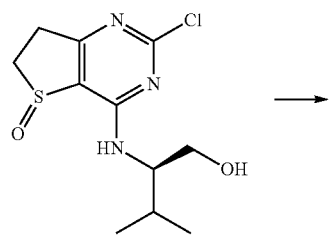

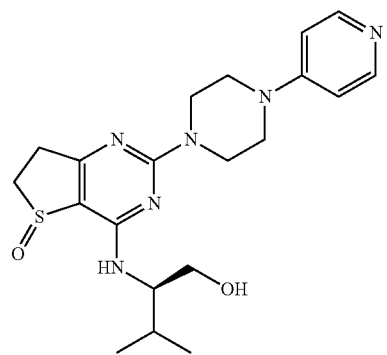

Example 1.18

Starting from (IV-2) (see 2.2) and 1-pyridin-4-yl-piperazine Example 1.18 is prepared and purified as the trifluoroacetate analogously to Example 1.10 (see 10.5). Analytical HPLC-MS (method C): RT=1.33 min.

19. SYNTHESIS OF (R)-2-{2-[4-(3-DIMETHYLAMINOPYRIDAZIN-4-YL)-PIPERAZIN-1-YL]-5-OXO-6,7-DIHYDRO-5H-5λ⁴-THIENO[3,2-d] PYRIMIDIN-4-YLAMINO}-3-METHYLBUTAN-1-OL (EXAMPLE 1.19)

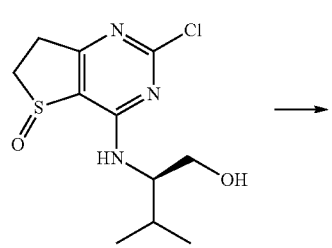

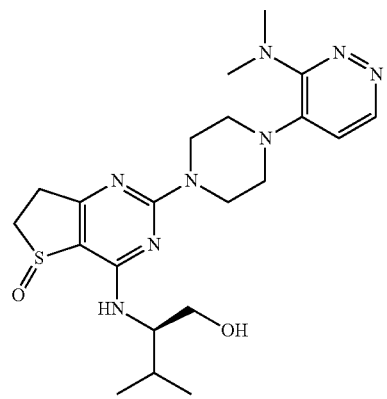

Example 1.19

Starting from (IV-2) (see 2.2) and (V-1) (see 10.4) Example 1.19 is prepared and purified as the trifluoroacetate analogously to Example 1.10 (see 10.5). Analytical HPLC-MS (method C): RT=1.37 min.

20. SYNTHESIS OF 6-CHLORO-4-{4-[4-((R)-1-HYDROXYMETHYL-2-METHYLPROPYLAMINO)-5-OXO-6,7-DIHYDRO-5H-5λ⁴-THIENO[3,2-d]PYRIMIDIN-2-YL]-PIPERAZIN-1-YL}-PYRIDAZIN-3-OL (EXAMPLE 1.20)

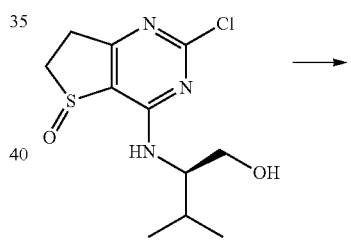

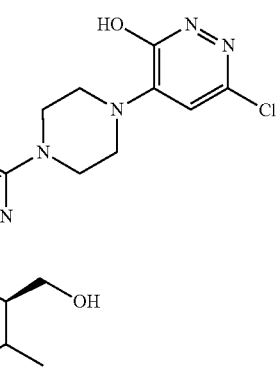

Example 1.20

Starting from (IV-2) (see 2.2) and (V-2) (see 11.2) Example 1.20 is prepared and purified analogously to Example 1.10 (see 10.5). Analytical HPLC-MS (method C): RT=1.55 min.

21. SYNTHESIS OF (R)-2-(2-{4-[6-(2-ETHOXY-ETHOXY)-PYRIDAZIN-3-YL]-PIPERAZIN-1-YL}-5-OXO-6,7-DIHYDRO-5H-5λ⁴-THIENO[3,2-d]PYRIMIDIN-4-YLAMINO)-3-METHYLBUTAN-1-OL (EXAMPLE 1.21)

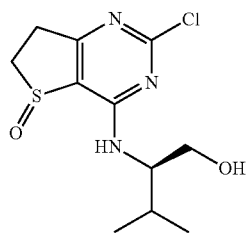

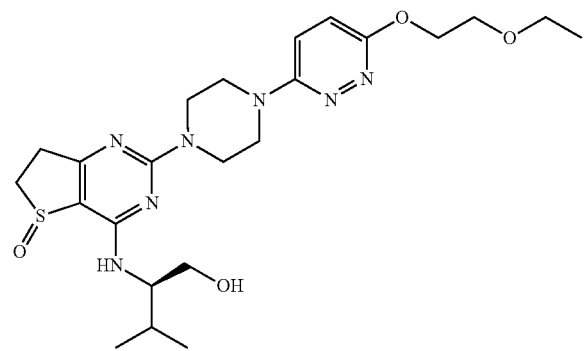

Example 1.21

Starting from (IV-2) (see 2.2) and (V-3) (see 12.1) Example 1.21 is prepared and purified as the trifluoroacetate analogously to Example 1.10 (see 10.5). Analytical HPLC-MS (method C): RT=1.45 min.

22. SYNTHESIS OF (R)-3-METHYL-2-[5-OXO-2-(4-PYRIDAZIN-4-YL-PIPERAZIN-1-YL)-6,7-DIHYDRO-5H-5λ⁴-THIENO[3,2-d]PYRIMIDIN-4-YLAMINO]-BUTAN-1-OL (EXAMPLE 1.22)

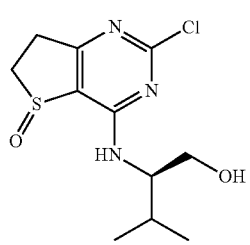

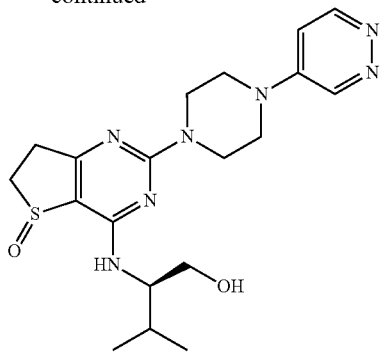

Example 1.22

Starting from (IV-2) (see 2.2) and (V-4) (see 13.1) Example 1.22 is prepared and purified as trifluoroacetate analogously to Example 1.10 (see 10.5). Analytical HPLC-MS (method C): RT=0.56 min.

23. SYNTHESIS OF {1-[5-OXO-2-(4-PYRIMIDIN-4-YL-PIPERAZIN-1-YL)-6,7-DIHYDRO-5H-5λ⁴-THIENO[3,2-d]PYRIMIDIN-4-YLAMINO]-CYCLOPROPYL}-METHANOL TRIFLUOROACETATE (EXAMPLE 1.23)

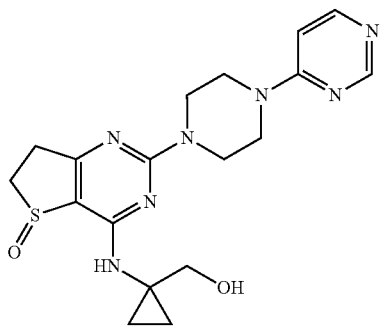

Example 1.23

Starting from (IV-4) (see 8.4) and 4-piperazin-1-yl-pyrimidine (J. Org. Chem. 1953, 1484) Example 1.23 is prepared and purified as the trifluoroacetate analogously to Example 1.10 (see 10.5). Analytical HPLC-MS (method C): RT=1.29 min.

24 SYNTHESIS OF {1-[5-OXO-2-(4-PYRIDIN-4-YL-PIPERAZIN-1-YL)-6,7-DIHYDRO-5H-5λ⁴-THIENO[3,2-d]PYRIMIDIN-4-YLAMINO]-CYCLOPROPYL}-METHANOL TRIFLUOROACETATE (EXAMPLE 1.24)

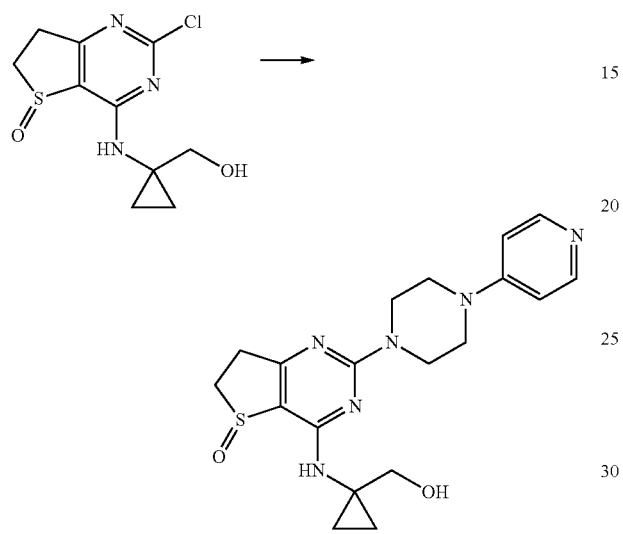

Example 1.24

Starting from (IV-4) (see 8.4) and 1-pyridin-4-yl-piperazine Example 1.24 is prepared and purified as the trifluoroacetate analogously to Example 1.10 (see 10.5). Analytical HPLC-MS (method C): RT=1.29 min.

25. SYNTHESIS OF (S)-1-METHYL-5-[5-OXO-2-(4-PYRIMIDIN-4-YL-PIPERAZIN-1-YL)-6,7-DIHYDRO-5H-5λ⁴-THIENO[3,2-d]PYRIMIDIN-4-YLAMINO]-PIPERIDIN-2-ONE (EXAMPLE 1.25)

25.1 (S)-5-dibenzylaminopiperidin-2-one

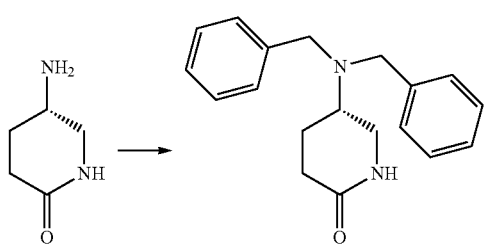 [SMILES: N[C@H]1CCC(=O)NC1 ; O=C1CC[C@H](N(Cc2ccccc2)Cc2ccccc2)CN1]

0.600 g 4-(S)-amino-delta-valerolactam hydrochloride, 0.970 ml benzylbromide and 1.5 g sodium hydrogen carbonate are suspended in 30 ml of ethanol. The reaction mixture is then stirred for 8 hours at 80° C. and then evaporated to dryness. The residue is suspended in water and the product is extracted with dichloromethane and purified by chromatography (silica gel, dichloromethane/methanol 100/0 to 95/5). 0.500 g of the product are obtained as an oil. Analytical HPLC-MS (method A): RT=1.01 min.

25.2 (S)-5-dibenzylamino-1-methylpiperidin-2-one

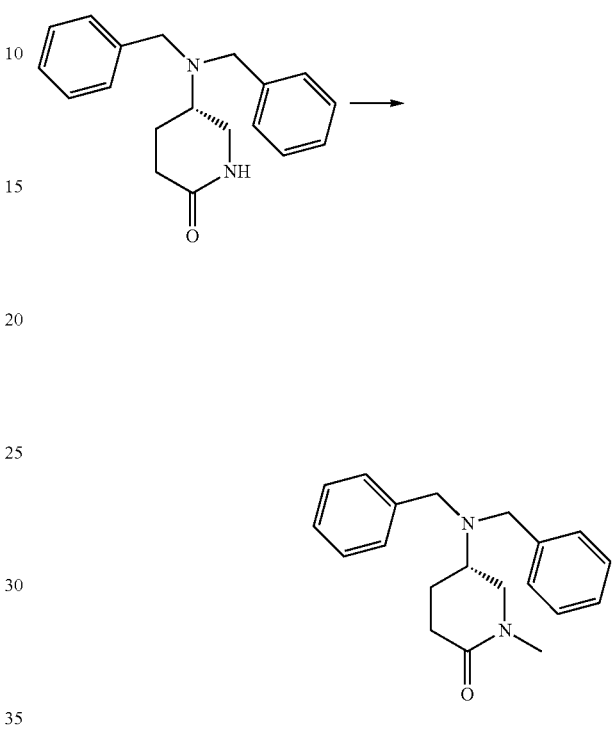

0.500 g (S)-5-dibenzylaminopiperidin-2-one are suspended in 15 ml of tetrahydrofuran. While cooling with the ice bath 0.175 g potassium-tert-butoxide are added. The reaction mixture is then stirred for 30 minutes at ambient temperature. While cooling with the ice bath 0.095 ml methyl iodide are added. The reaction mixture is then stirred for 48 hours at ambient temperature and then combined with a saturated NaCl solution. The product is extracted with ethyl acetate. 0.450 g of the product are obtained as an oil. Analytical HPLC-MS (method A): RT=1.07 min.

25.3 (S)-5-amino-1-methylpiperidin-2-one

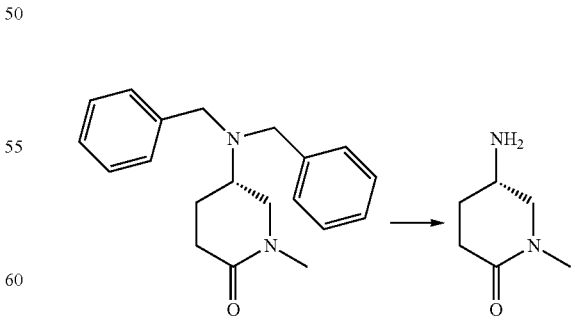

0.450 g (S)-5-dibenzylamino-1-methylpiperidin-2-one are suspended in 25 ml of methanol and hydrogenated with 0.150 g Pd/C 10% at a pressure of 3 bar and a temperature of 60° C. After 16 hours the catalyst is suction filtered and the filtrate is evaporated to dryness. 0.190 g of the product are obtained as an oil. ¹H NMR (400 MHz, DMSO): 2.76 (3H, s).

25.4 (S)-5-(2-chloro-6,7-dihydrothieno[3,2-d]pyrimidin-4-ylamino)-1-methylpiperidin-2-one (III-5)

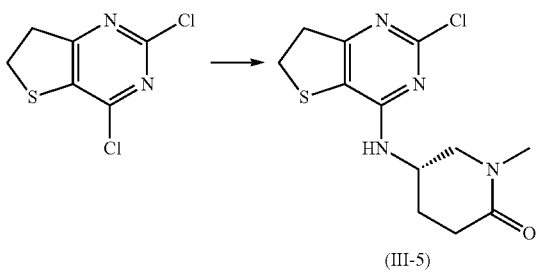 [SMILES: Clc1nc(Cl)c2c(n1)CCS2 ; CN1C[C@@H](Nc2nc(Cl)nc3c2SCC3)CCC1=O ; "(III-5)"]

(III-5)

0.27 g (II) are placed in 3 ml dioxane, then 0.45 ml diisopropylethylamine and 0.25 g (S)-5-amino-1-methylpiperidin-2-one are added. The reaction mixture is heated to 130° C. until there is no further reaction, cooled and then evaporated down. The product is extracted with dichloromethane and purified by chromatography (preparative HPLC, method B). 0.26 g (III-5) are obtained as a solid. Analytical HPLC-MS (method A): RT=1.06 min.

25.5 (S)-5-(2-chloro-5-oxo-6,7-dihydro-5H-5λ⁴-thieno[3,2-d]pyrimidin-4-ylamino)-1-methylpiperidin-2-one (IV-5)

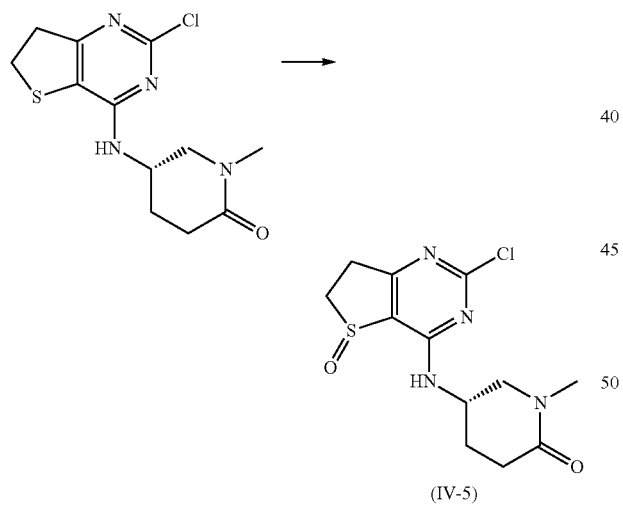

(IV-5)

0.04 g S-(−)-1,1′-bi-2-naphthol are placed in 5 ml chloroform under argon, then 0.02 ml titanium(IV)isopropoxide and 0.025 ml of water are added. The reaction mixture is stirred for 1 hour at ambient temperature. Then a suspension of 0.2 g (III-5) in 4 ml dichloromethane is added. The reaction mixture is cooled to −5° C. and after 20 minutes 0.12 ml tert-butylhydroperoxide 5-6 M in decane are added dropwise. The reaction mixture is stirred further at −5° C. until there is no further reaction, and made basic with NH₄OH. The product is extracted with dichloromethane and purified by chromatography (silica gel, ethyl acetate/methanol 100/0 to 60/40). 0.09 g (IV-5) are obtained as a solid. Analytical HPLC-MS (method A): RT=0.83 min.

25.6 (S)-1-methyl-5-[5-oxo-2-(4-pyrimidin-4-yl-piperazin-1-yl)-6,7-dihydro-5H-5λ⁴-thieno[3,2-d]pyrimidin-4-ylamino]-piperidin-2-one (Example 1.25)

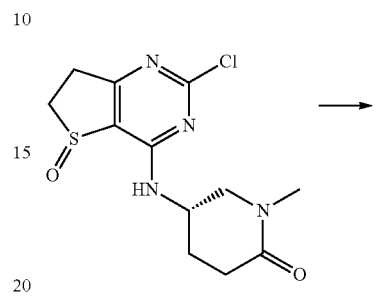

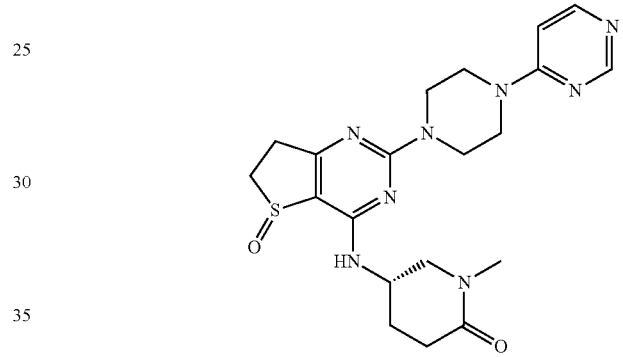

Example 1.25

Starting from (IV-5) and 4-piperazin-1-yl-pyrimidine (*J. Org. Chem.* 1953, 1484) Example 1.25 is prepared and purified as the trifluoroacetate analogously to Example 1.10 (see 10.5). Analytical HPLC-MS (method C): RT=1.28 min.

26. SYNTHESIS OF {2-[4-(5-FLUORO-1-METHYL-1H-BENZIMIDAZOL-2-YL)-PIPERAZIN-1-YL]-5-OXO-6,7-DIHYDRO-5H-5λ⁴-THIENO[3,2-d]PYRIMIDIN-4-YL}-(TETRAHYDROPYRAN-4-YL)-AMINE (EXAMPLE 1.26)

26.1 (4-fluoro-2-nitrophenyl)-methylamine

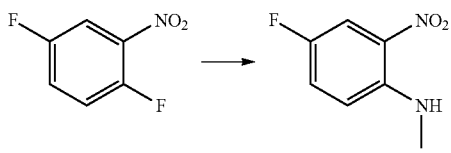

7.3 g of 1,4-difluoro-2-nitrobenzene are slowly added to 30 ml of a 40% aqueous methylamine solution whilst cooling with ice and the reaction mixture is stirred for 1 hour at ambient temperature. The precipitated product is suction filtered and recrystallised from water and ethanol. 6.3 g product are obtained as a solid. M.p=74-76° C.

26.2 4-fluoro-$N^1$-methylbenzene-1,2-diamine

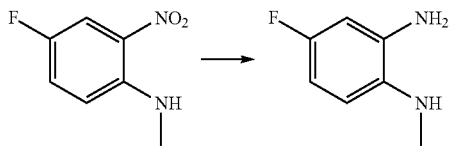

6.2 g (4-fluoro-2-nitrophenyl)-methylamine are suspended in 200 ml of ethyl acetate and hydrogenated with 1 g of Raney nickel at a pressure of 5 bar and ambient temperature. After 4.5 hours the catalyst is suction filtered and the filtrate is evaporated to dryness. 3.9 g product are obtained as an oil.

26.3
5-fluoro-1-methyl-1,3-dihydrobenzimidazol-2-one

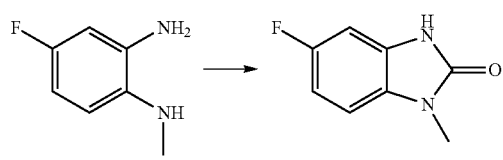

6 g of 4-fluoro-N1-methylbenzene-1,2-diamine are suspended in 200 ml of tetrahydrofuran and 7.1 g N,N'-carbonyldiimidazole are added. The reaction mixture is stirred for 48 hours at ambient temperature and the precipitated product is suction filtered and recrystallised from dioxane. 3.9 g product are obtained as a solid. M.p=207° C.

26.4 2-chloro-5-fluoro-1-methyl-1H-benzimidazole

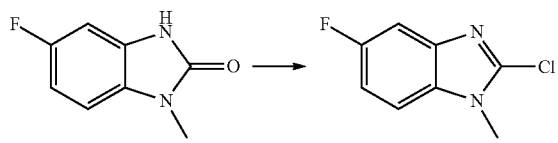

3.9 g 5-fluoro-1-methyl-1,3-dihydro-benzimidazole-2-one are suspended in 80 ml phosphorus oxychloride and the reaction mixture is stirred for 2 hours at reflux temperature. 50 ml diethylaniline are added. The reaction mixture is stirred for a further 10 minutes at reflux temperature and slowly mixed with ice water. The product is extracted with dichloromethane and purified by chromatography (silica gel, cyclohexane, methylene chloride/acetone 20/1). 1.4 g product are obtained as a solid. M.p=138-141° C.

26.5 5-fluoro-1-methyl-2-piperazin-1-yl-1H-benzimidazole (V-8)

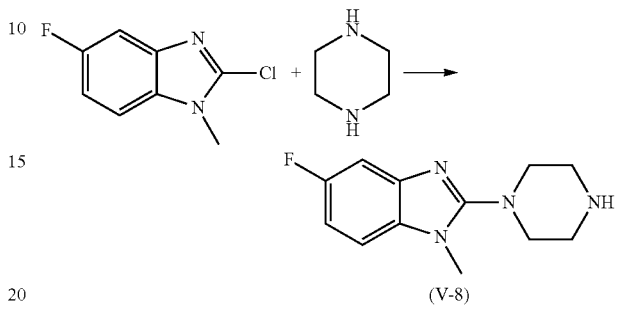

0.7 g 2-chloro-5-fluoro-1-methyl-1H-benzimidazole and 1.3 g piperazine are suspended in 10 ml n-butanol and stirred for 48 hours at ambient temperature. The reaction mixture is evaporated to dryness and the product is purified by chromatography (aluminium oxide, methylene chloride/methanol 10/1). 0.73 g (V-8) are obtained as a solid. $^1$H NMR (400 MHz, DMSO): 6.9 (1H, t); 3.6 (3H, s).

26.6 {2-[4-(5-fluoro-1-methyl-1H-benzoimidazol-2-yl)-piperazin-1-yl]-5-oxo-6,7-dihydro-5H-5$\lambda^4$-thieno[3,2-d]pyrimidin-4-yl}-(tetrahydropyran-4-yl)-amine (Example 1.26)

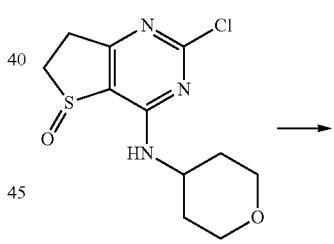

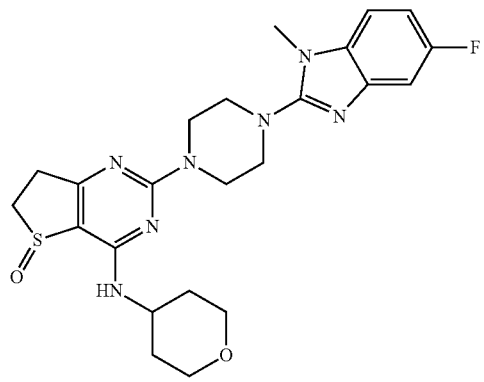

Example 1.26

Starting from (IV-3) (see 4.2) and (V-8) Example 1.26 is prepared and purified analogously to Example 1.10 (see 10.5). Analytical HPLC-MS (method C): RT=1.48 min.

27. SYNTHESIS OF [5-OXO-2-(4-PYRIDIN-4-YL-PIPERAZIN-1-YL)-6,7-DIHYDRO-5H-5λ⁴-THIENO[3,2-d]PYRIMIDIN-4-YL]-(TETRAHYDROPYRAN-4-YL)-AMINE (EXAMPLE 1.27)

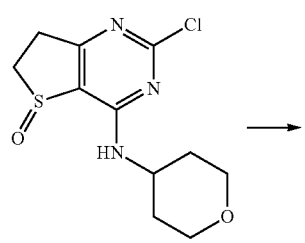

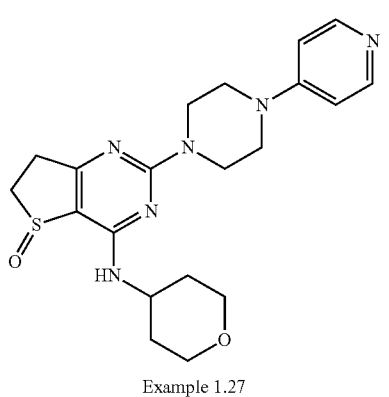

Example 1.27

Starting from (IV-3) (see 4.2) and 1-pyridin-4-yl-piperazine Example 1.27 is prepared and purified as the trifluoroacetate analogously to Example 15 (see 10.5). Analytical HPLC-MS (method C): RT=1.32 min.

28. SYNTHESIS OF (3-FLUOROPHENYL)-{2-[4-(4-METHOXY-1-METHYL-1H-BENZIMIDAZOL-2-YL)-PIPERAZIN-1-YL]-5-OXO-6,7-DIHYDRO-5H-5λ⁴-THIENO[3,2-d]PYRIMIDIN-4-YL}-AMINE (EXAMPLE 1.28)

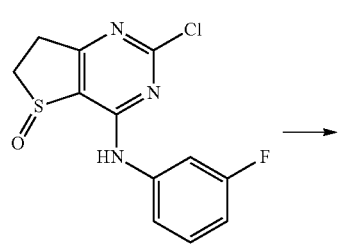

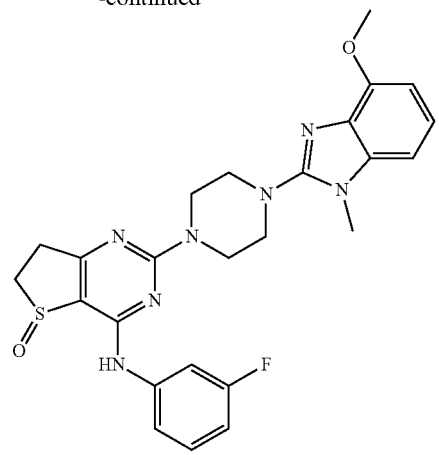

Example 1.28

Starting from (IV-1) (see 1.2) and (V-5) (see 14.7) Example 1.28 is prepared and purified as the trifluoroacetate analogously to Example 1.10 (see 10.5). Analytical HPLC-MS (method C): RT=1.73 min.

29. SYNTHESIS OF {2-[4-(7-ETHYL-6,7,8,9-TETRAHYDRO-5H-PYRAZINO[2,3-d]AZEPIN-2-YL)-PIPERAZIN-1-YL]-5-OXO-6,7-DIHYDRO-5H-5λ⁴-THIENO[3,2-d]PYRIMIDIN-4-YL}-(3-FLUOROPHENYL)-AMINE (EXAMPLE 1.29)

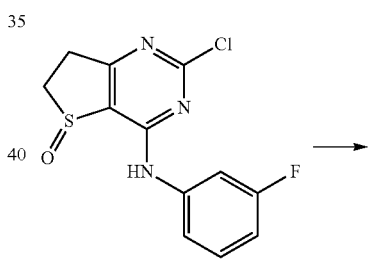

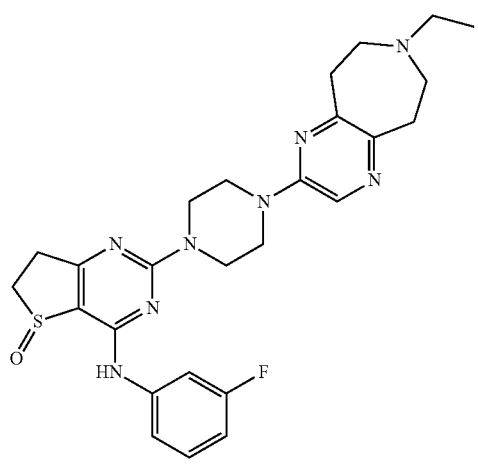

Example 1.29

Starting from (IV-1) (see 1.2) and (V-6) (see 15.2) Example 1.29 is prepared and purified as the trifluoroacetate analogously to Example 1.10 (see 10.5). Analytical HPLC-MS (method C): RT=1.6 min.

30. SYNTHESIS OF (3-FLUOROPHENYL)-[5-OXO-2-(4-PYRIMIDIN-4-YL-PIPERAZIN-1-YL)-6,7-DIHYDRO-5H-5λ⁴-THIENO[3,2-d]PYRIMIDIN-4-YL]-AMINE (EXAMPLE 1.30)

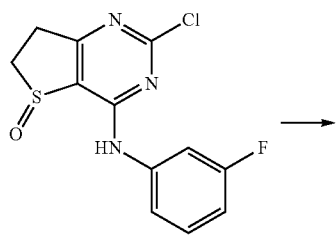

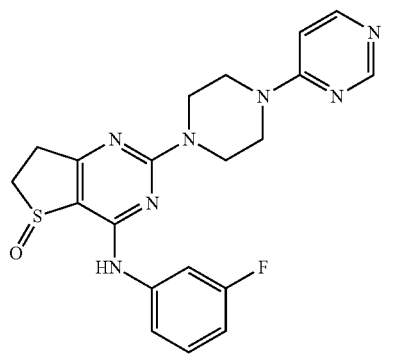

Example 1.30

Starting from (IV-1) (see 1.2) and 4-piperazin-1-yl-pyrimidine (*J. Org. Chem.* 1953, 1484) Example 1.30 is prepared and purified as the trifluoroacetate analogously to Example 1.10 (see 10.5). Analytical HPLC-MS (method C): RT=1.56 min.

31. SYNTHESIS OF 4-{4-[4-(3-FLUOROPHENYLAMINO)-5-OXO-6,7-DIHYDRO-5H-5λ⁴-THIENO[3,2-d]PYRIMIDIN-2-YL]-PIPERAZIN-1-YL}-PYRIDIN-2-OL (EXAMPLE 1.31)

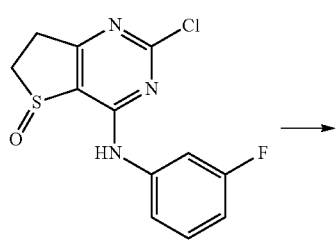

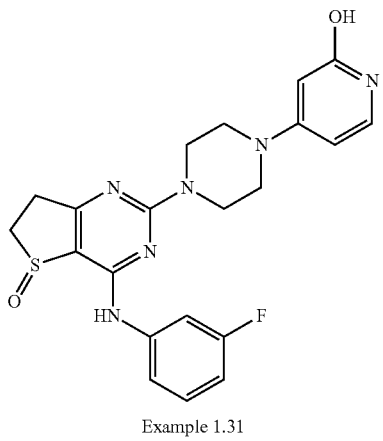

Example 1.31

Starting from (IV-1) (see 1.2) and (V-7) (see 17.3) Example 1.31 is prepared and purified analogously to Example 1.10 (see 10.5). Analytical HPLC-MS (method C): RT=1.61 min.

32. SYNTHESIS OF (3-FLUOROPHENYL)-[5-OXO-2-(4-PYRIDIN-4-YL-PIPERAZIN-1-YL)-6,7-DIHYDRO-5H-5λ⁴-THIENO[3,2-d]PYRIMIDIN-4-YL]-AMINE (EXAMPLE 1.32)

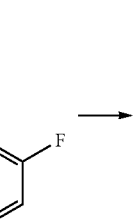

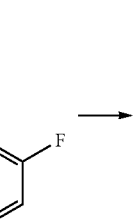

Example 1.32

Starting from (IV-1) (see 1.2) and 1-pyridin-4-yl-piperazine Example 1.32 is prepared and purified analogously to Example 1.10 (see 10.5). Analytical HPLC-MS (method C): RT=1.56 min.

33. SYNTHESIS OF (3-FLUOROPHENYL)-(2-{4-[4-(4-FLUOROPHENYL)-THIAZOL-2-YL]-PIPERAZIN-1-YL}-5-OXO-6,7-DIHYDRO-5H-5λ⁴-THIENO[3,2-d]PYRIMIDIN-4-YL)-AMINE (EXAMPLE 1.33)

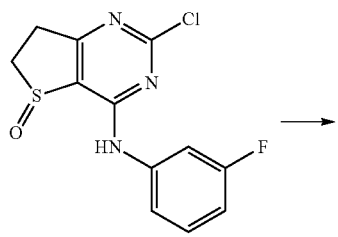

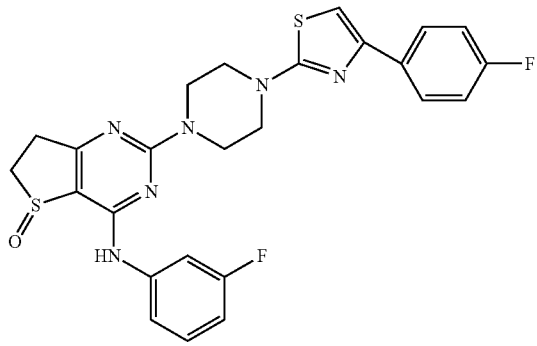

Example 1.33

Starting from (IV-1) (see 1.2) and 1-[4-(4-fluorophenyl)-thiazol-2-yl]-piperazine Example 1.33 is prepared and purified analogously to Example 1.10 (see 10.5). Analytical HPLC-MS (method C): RT=2.42 min.

34. SYNTHESIS OF [2-(4-BENZO[d]ISOXAZOL-3-YL-PIPERAZIN-1-YL)-5-OXO-6,7-DIHYDRO-5H-5λ⁴-THIENO[3,2-d]PYRIMIDIN-4-YL]-(3-FLUOROPHENYL)-AMINE (EXAMPLE 1.34)

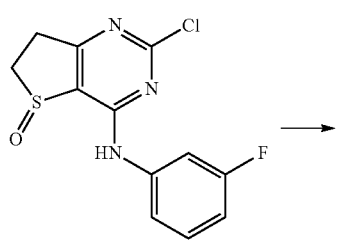

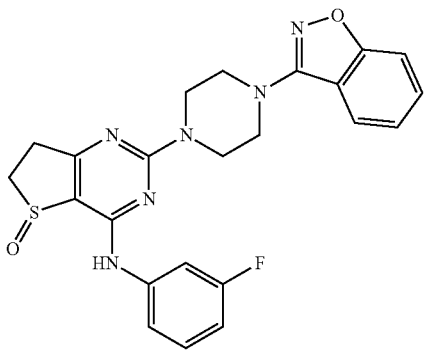

Example 1.34

Starting from (IV-1) (see 1.2) and 3-piperazin-1-yl-benzo[d]isoxazole Example 1.34 is prepared and purified analogously to Example 1.10 (see 10.5). Analytical HPLC-MS (method C): RT=2.19 min.

35. SYNTHESIS OF (R)-2-(2-{4-[4-(4-FLUOROPHENYL)-THIAZOL-2-YL]-PIPERAZIN-1-YL}-5-OXO-6,7-DIHYDRO-5H-5λ⁴-THIENO[3,2-d]PYRIMIDIN-4-YLAMINO)-3-METHYLBUTAN-1-OL (EXAMPLE 1.35)

Example 1.35

Starting from (IV-2) (see 2.2) and 1-[4-(4-fluorophenyl)-thiazol-2-yl]-piperazine Example 1.35 is prepared and purified analogously to Example 1.10 (see 10.5). Analytical HPLC-MS (method C): RT=1.91 min.

36. SYNTHESIS OF (R)-2-[2-(4-BENZO[d]ISOXAZOL-3-YL-PIPERAZIN-1-YL)-5-OXO-6,7-DIHYDRO-5H-5λ⁴-THIENO[3,2-d]PYRIMIDIN-4-YLAMINO]-3-METHYLBUTAN-1-OL (EXAMPLE 1.36)

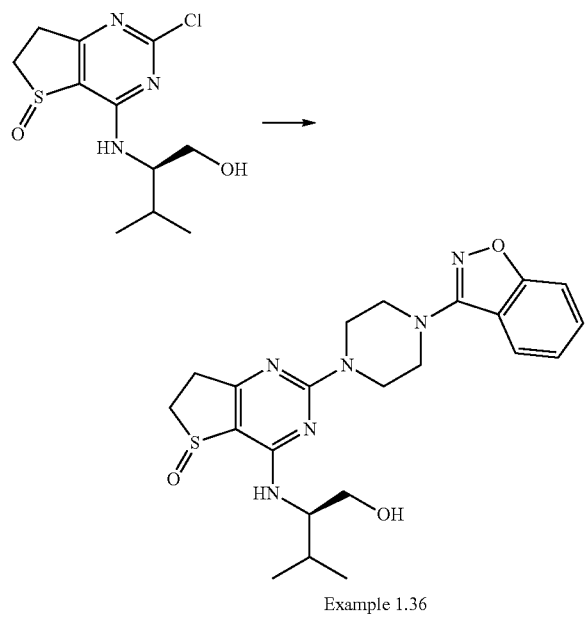

Example 1.36

Starting from (IV-2) (see 2.2) and 3-piperazin-1-yl-benzo[d]isoxazole Example 1.36 is prepared and purified analogously to Example 1.10 (see 10.5). Analytical HPLC-MS (method C): RT=1.76 min.

Methods of Chromatography

The Example compounds prepared according to the synthesis schemes shown above were characterised by the following chromatographic methods, which—if used—are individually specified in Table A.

Analytical HPLC-MS, Method A

Waters ZMD mass spectrometer (positive ionisation (ESI+)), Alliance 2690/2695 HPLC (diode array detector, wavelength range: 210 to 500 nm), Waters 2700 Autosampler, Waters 996/2996.

A: water with 0.10% TFA
B: acetonitrile with 0.10% TFA

| time in min | % A | % B | flow rate in ml/min |
|---|---|---|---|
| 0.00 | 95 | 5 | 2.50 |
| 0.20 | 95 | 5 | 2.50 |
| 1.50 | 2 | 98 | 2.50 |
| 1.70 | 2 | 98 | 2.50 |
| 1.90 | 95 | 5 | 2.50 |
| 2.20 | 95 | 5 | 2.50 |

The stationary phase used is a Merck Chromolith™ Flash RP-18e column, 4.6 mm×25 mm (column temperature: constant at 25° C.).

Analytical HPLC-MS, Method B

Waters ZMD mass spectrometer (positive ionisation (ESI+)), Alliance 2690/2695 HPLC (diode array detector, wavelength range: 210 to 500 nm), Waters 2700 Autosampler, Waters 996/2996.

A: water with 0.10% NH₃
B: acetonitrile with 0.10% NH₃

| time in min | % A | % B | flow rate in ml/min |
|---|---|---|---|
| 0.00 | 95 | 5 | 3.00 |
| 0.20 | 95 | 5 | 3.00 |
| 1.50 | 2 | 98 | 3.00 |
| 1.90 | 2 | 98 | 3.00 |
| 2.00 | 2 | 98 | 3.00 |

The stationary phase used is Waters, X-Bridge, C18, 3.5 nm, 4.6×20 mm, ambient temperature Analytical HPLC-MS, Method C Waters ZQ2000 mass spectrometer (positive ionisation (ESI+)), HP1100 HPLC (DAD, wavelength range: 210 to 500 nm), and Gilson 215 Autosampler.

A: water with 0.10% TFA
B: acetonitrile with 0.10% TFA

| time in min | % A | % B | flow rate in ml/min |
|---|---|---|---|
| 0.00 | 95 | 5 | 1.50 |
| 2.00 | 0 | 100 | 1.50 |
| 2.50 | 0 | 100 | 1.50 |
| 2.60 | 95 | 5 | 1.50 |

The stationary phase used is a Sunfire C18 column, 4.6×50 mm, 3.5 µm, column temperature 40° C.

Analytical HPLC, Method A

Agilent 1100, .diode array detection is carried out in the wavelength range 210-380 nm.

A: water with 0.10% TFA
B: acetonitrile with 0.13% TFA

| time in min | % A | % B | flow rate in ml/min |
|---|---|---|---|
| 0.00 | 95 | 5 | 1.50 |
| 0.60 | 95 | 5 | 1.50 |
| 3.40 | 2 | 98 | 1.50 |
| 3.90 | 2 | 98 | 1.50 |
| 4.20 | 95 | 5 | 1.50 |
| 4.90 | 95 | 5 | 1.50 |

The stationary phase used is a Varian Microsorb column, RP C18, 3 µm, 100 A, ambient temperature.

Preparative HPLC-MS, Method A

Waters ZQ2000 mass spectrometer (positive ionisation (ESI+)), HP1100 HPLC (DAD, wavelength range: 210-500 nm), and Gilson 215 Autosampler.

A: water with 0.10% TFA
B: acetonitrile

| time in min | % A | % B | flow rate in ml/min |
|---|---|---|---|
| 0.00 | 90 | 10 | 50 |
| 1.50 | 90 | 10 | 50 |
| 8.00 | 40 | 60 | 50 |
| 10.00 | 40 | 60 | 50 |
| 11.00 | 90 | 10 | 50 |

The stationary phase used is a Sunfire C18 column, 30×100 mm, 5 µm, ambient temperature.

Preparative HPLC, Method A

Gilson HPLC with Gilson UV-VIS-155 Detektor, 231 XL sampling injector.

The wavelength given is the substance-specific UV maximum.

A: water with 0.1% ammonia 35%
B: acetonitrile

| time in min | % A | % B | flow rate in ml/min |
|---|---|---|---|
| 0.00 | 95 | 5 | 180 |
| 1.40 | 95 | 5 | 180 |
| 17.00 | 2 | 98 | 180 |
| 18.50 | 2 | 98 | 180 |
| 18.70 | 95 | 5 | 180 |
| 20.-50 | 95 | 5 | 180 |

The stationary phase used is a Pursuit XRS RP 18 column, 10 µm, 50×150 mm, ambient temperature.

Preparative HPLC, Method B

Gilson HPLC with Gilson UV-VIS-155 detector, 231 XL sampling injector.

The wavelength given is the substance-specific UV maximum.

A: water with 0.13% TFA
B: acetonitrile with 0.1% TFA

| time in min | % A | % B | flow rate in ml/min |
|---|---|---|---|
| 0.00 | 95 | 5 | 165 |
| 1.30 | 95 | 5 | 165 |
| 8.90 | 2 | 98 | 165 |
| 10.00 | 2 | 98 | 165 |
| 10.50 | 95 | 5 | 165 |
| 11.60 | 95 | 5 | 165 |

The stationary phase used is a Microsorb RP 18 column, 8 µm, 50×65 mm, ambient temperature.

Indications

As has been found, the combinations according to the invention containing a PDE4 inhibitor, preferably a PDE4 inhibitor of formula 1 and at least one EP4 receptor antagonist are characterised by their wide range of applications in the therapeutic field. Particular mention should be made of those applications for which the combinations according to the invention are preferably suited on account of their pharmaceutical efficacy as PDE4 inhibitors. Examples include respiratory or gastrointestinal diseases or complaints, inflammatory diseases of the joints, skin or eyes, cancers, and also diseases of the peripheral or central nervous system.

Particular mention should be made of the prevention and treatment of diseases of the airways or of the lung which are accompanied by increased mucus production, inflammations and/or obstructive diseases of the airways. Examples include acute, allergic or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, paediatric asthma, bronchiectases, pulmonary fibrosis, ARDS (acute adult respiratory distress syndrome), bronchial oedema, pulmonary oedema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis or mucoviscidosis, or alpha1-antitrypsin deficiency.

Also deserving special mention is the treatment of inflammatory diseases of the gastrointestinal tract. Examples include acute or chronic inflammatory changes in gall bladder inflammation, Crohn's disease, ulcerative colitis, inflammatory pseudopolyps, juvenile polyps, colitis cystica profunda, pneumatosis cystoides intestinales, diseases of the bile duct and gall bladder, e.g. gallstones and conglomerates, for the treatment of inflammatory diseases of the joints such as rheumatoid arthritis or inflammatory diseases of the skin and eyes.

Preferential mention should also be made of the treatment of cancers. Examples include all forms of acute and chronic leukaemias such as acute lymphatic and acute myeloid leukaemia, chronic lymphatic and chronic myeloid leukaemia, and bone tumours such as osteosarcoma and all types of glioma such as oligodendroglioma and glioblastoma.

Preferential mention should also be made of the prevention and treatment of diseases of the peripheral or central nervous system. Examples of these include depression, bipolar or manic depression, acute and chronic anxiety states, schizophrenia, Alzheimer's disease, Parkinson's disease, acute and chronic multiple sclerosis or acute and chronic pain as well as injuries to the brain caused by stroke, hypoxia or craniocerebral trauma.

Particularly preferably the present invention relates to the use of the combinations according to the invention for preparing a medicament for the treatment of inflammatory or obstructive diseases of the upper and lower respiratory tract including the lungs, such as for example allergic rhinitis, chronic rhinitis, bronchiectasis, cystic fibrosis, idiopathic pulmonary fibrosis, fibrosing alveolitis, COPD, chronic bronchitis, chronic sinusitis, asthma, Crohn's disease, ulcerative colitis, particularly COPD, chronic bronchitis and asthma.

Also preferred is the use of the combinations according to the invention for the treatment of diseases of the peripheral or central nervous system such as depression, bipolar or manic depression, acute and chronic anxiety states, schizophrenia, Alzheimer's disease, Parkinson's disease, acute and chronic multiple sclerosis, amyotropic lateral sclerosis (ALS) or acute and chronic pain conditions and brain damage caused by stroke, hypoxia or cerebro-cranial trauma.

It is most preferable to use the combinations according to the invention for the treatment of inflammatory and obstructive diseases such as COPD, chronic bronchitis, chronic sinusitis, asthma, Crohn's disease, ulcerative colitis, particularly COPD, chronic bronchitis and asthma.

An outstanding aspect of the formulations according to the invention containing a combination of one (or more) PDE4 inhibitors, preferably the PDE4 inhibitors of formula 1, and at least one EP4 receptor antagonist is their reduced profile of side effects compared with formulations that contain the same PDE4 inhibitors in the same amount in the absence of an EP4 receptor antagonist. Side effects that frequently occur when taking a PDE4 inhibitor preferentially include, inter alia, diarrhoea, nausea and vomiting. In the rat model further side effects were observed after the administration of PDE4 inhibitor, such as for example weight loss, loss of spleen weight, leukocytosis and neutrophilia, diarrhoea and the occurrence of mesenteric vasculitis.

By a reduced profile of side effects is meant, within the scope of the invention, in particular being able to administer a therapeutically effective dose of a PDE4 inhibitor in a pharmaceutical composition according to the invention without inducing to any appreciable extent in the patient the or at least one of the side effects commonly observed when PDE4 inhibitors are administered (diarrhoea, nausea, vomiting, weight loss, loss of spleen weight, leukocytosis and neutrophilia and the occurrence of mesenteric vasculitis). It is particularly preferable to administer a therapeutically effective amount of a PDE4 inhibitor in the composition according to the invention at every stage of the course of the disease without triggering the typical PDE4 inhibitor-mediated side effects of diarrhoea, weight loss, leukocytosis, neutrophilia or mesenteric vasculitis. In a particular aspect the present invention relates to the administration of a therapeutically effective amount of the pharmaceutical composition according to the invention at every stage of the course of the disease without triggering the typical PDE4 inhibitor-mediated side effect of mesenteric vasculitis to any appreciable degree.

Experiments on the rat model described hereinafter show that the pharmaceutical compositions according to the invention containing a PDE4 inhibitor and at least one EP4 receptor antagonist substantially reduce or even totally prevent many of the side effects which occur when the corresponding PDE4 inhibitor is administered on its own.

Experimental Method:

Experiment 1: Diclofenac Provides Protection Against Roflumilast-Mediated Effects Such as Weight Loss, Loss of Spleen Weight, Neutrophilia and Mesenteric Vasculitis Six male Wistar rats in each group were treated for four days with the following substances (all substances are given p.o.=orally):

Group 1 ("control group"): Six male Wistar rats were given a daily dose of 0.5% Natrosol (placebo) at the times 0800, 1300 and 1700 hours.

Group 2 ("diclofenac group"): Six male Wistar rats were given a daily dose of 1 mg/kg of diclofenac (NSAID) at the times 0800 and 1700 hours and 0.5% Natrosol (placebo) at 1300 hours.

Group 3 ("roflumilast group"): Six male Wistar rats were given a daily dose of 0.5% Natrosol (placebo) at 0800 and 1700 hours and 10 mg/kg roflumilast (PDE4 inhibitor) at 1300 hours.

Group 4 ("roflumilast+diclofenac group"): Six male Wistar rats were given a daily dose of 1 mg/kg diclofenac (NSAID) at the times 0800 and 1700 hours and 10 mg/kg roflumilast (PDE4 inhibitor) at 1300 hours.

For pharmacokinetic analysis (determining the plasma levels of the substances) on day 4 one rat from each group was used; these rats were no longer available for other parameters under investigation. The same applied to one rat from the roflumilast group which died between day 4 and day 5 of the experiment.

During the experiment the body weights of the animals were determined and the differences in the body weights of the rats from the different groups towards the end of the experiment were shown as a percentage change from the time of the first administration (=day 1, 0800 hours (=time $t_0$)). The average±standard deviation of the body weights at time $t_0$ was 355±17 g.

At the end of the experiment (day 5, 95 hours after $t_0$ ($t_0$=the time of the first administration on day 1, 0800)) the proportion of neutrophils (in % of white blood cells, FIG. 2) were determined from the blood of 4 or 5 of the rats from the individual groups. In addition, the weights of the animals' spleens were measured and the mesenteries were dissected for histopathological investigation for vasculitis (multifocal perivascular mononuclear/polymorphonuclear infiltration).

Figure 1:
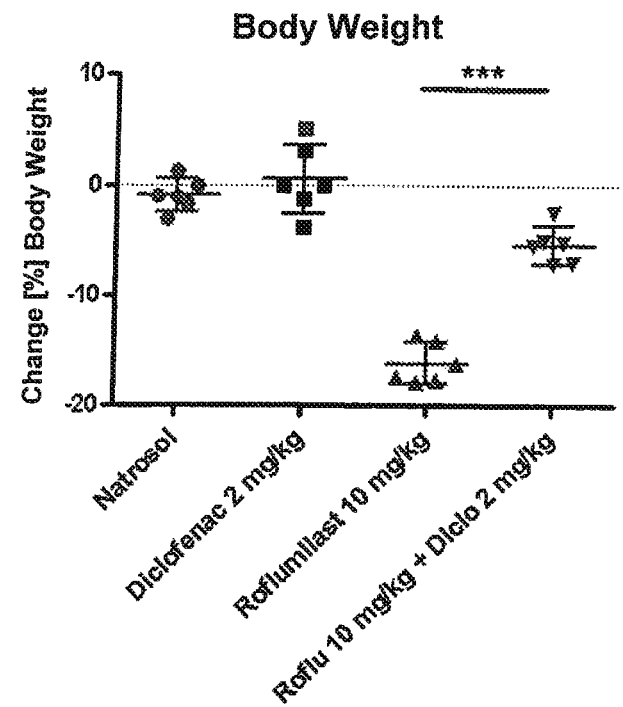
FIG. 1 shows the changes in the body weight measured after the respective administrations to the control (Natrosol) group, the diclofenac group, the roflumilast group and the roflumilast+diclofenac group (statistics: Two-way analysis of variance; ***=p<0.001).
Figure 2:
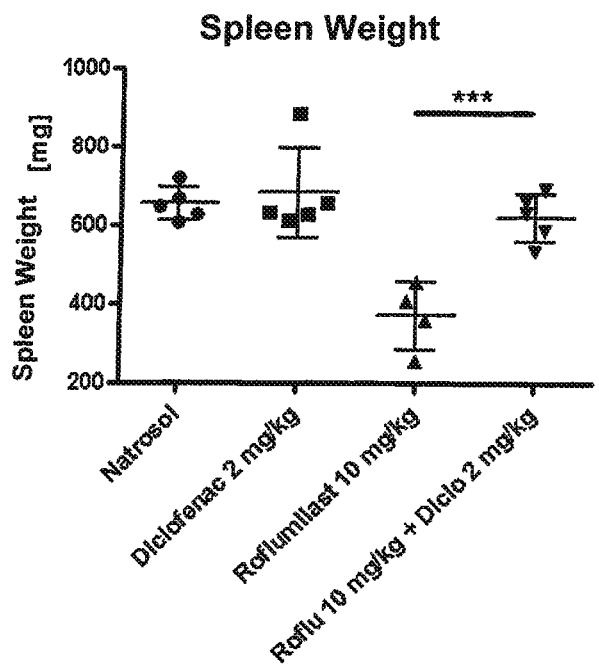
FIG. 2 shows the changes in the spleen weight measured after the respective administrations to the control (Natrosol) group, the diclofenac group, the roflumilast group and the roflumilast+diclofenac group (statistics: Two-way analysis of variance; ***=p<0.001).
Figure 3:
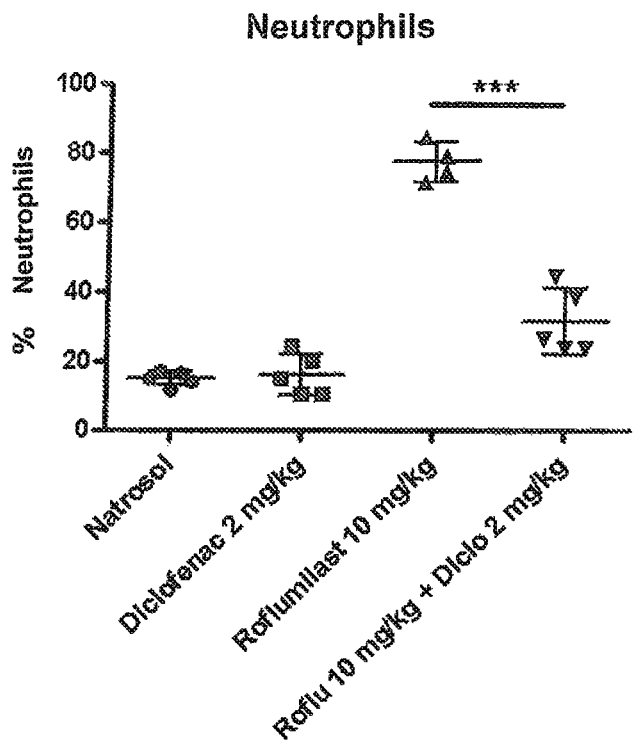
FIG. 3 shows the percentage of neutrophils in the blood after the respective administrations to the control (Natrosol) group, the diclofenac group, the roflumilast group and the roflumilast+diclofenac group (statistics: Two-way analysis of variance; ***=p<0.001).
Figure 4:
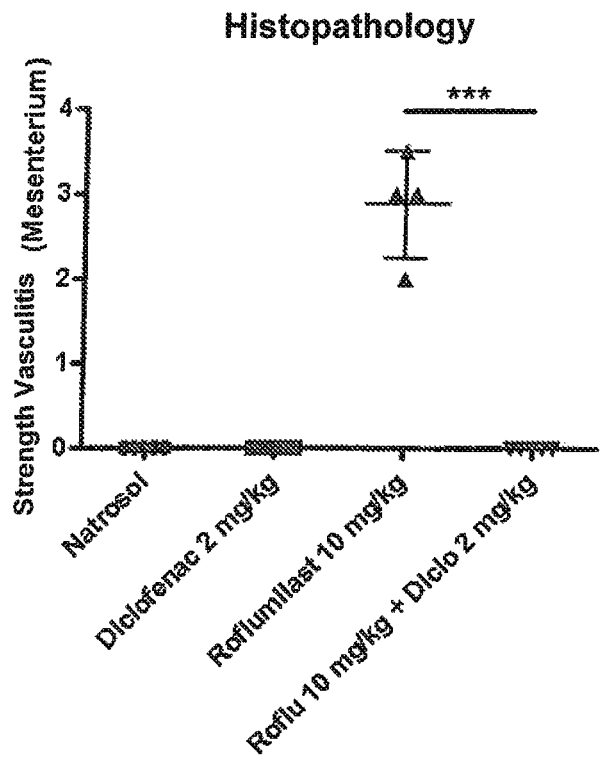
FIG. 4 shows the increase in the vasculitis observed in the mesentery after the respective administrations to the control (Natrosol) group, the diclofenac group, the roflumilast group and the roflumilast+diclofenac group (statistics: Two-way analysis of variance; ***=p<0.001).

To summarise, it can be stated that the PDE4 inhibitor-mediated side effects observed in the Roflumilast group such as loss of body weight (FIG. 1), loss of spleen weight (FIG. 2), neutrophilia (FIG. 3) and mesenteric vasculitis (monocyte/polymorphonuclear infiltration into the mesentery, FIG. 4) can be substantially reduced or prevented (may even be reduced almost to the levels for the control group), if an NSAID such as for example diclofenac is co-administered simultaneously or only offset by a few hours (see Roflumilast+Diclofenac group). The parameters measured after the administration of diclofenac on its own appeared to be very similar to the control groups.

On the one hand, during the treatment of COPD and asthma patients with a PDE4 inhibitor the simultaneous administration of an NSAID such as for example diclofenac therefore has major advantages, as the NSAID can substantially reduce or even prevent the PDE4-receptor-mediated side effects. On the other hand, it has long been known that NSAIDs such as diclofenac when taken regularly have their own side effects, such as for example potent gastrointestinal side effects, particularly the formation of gastric ulcers. However, it would be necessary to take these NSAIDs regularly in order to reduce the PDE4-mediated side effects, as the treatment of COPD and asthma patients with PDE4-inhibitors generally indicates long-term therapy. Consequently, the question arises regarding alternatives to the PDE4 inhibitor/NSAID combined therapy which have a lower side effect profile.

Experiment 2: The COX-2 Selective Inhibitor Lumiracoxib, but not the COX-1 Selective Inhibitor SC-560, Protects Against Roflumilast-Mediated Effects Such as Loss of Body Weight, Loss of Spleen Weight, Neutrophilia and Mesenteric Vasculitis Six male Wistar rats in each group were treated for four days with the following substances (all drugs were given p.o.=orally):

group 1 ("control group"): Six male Wistar rats were given a daily dosage of 0.5% Natrosol (Placebo) at the times 0800, 1300 and 1700 hours.

group 2 ("SC-560 group"): Six male Wistar rats were given a daily dosage of in each case 2 mg/kg SC-560 (NSAID, selective for Cox-1) at the times 0800 and 1700 hours and 0.5% Natrosol at 1300 hours.

group 3 ("Lumiracoxib group"): Six male Wistar rats were given a daily dosage of in each case 2 mg/kg Lumiracoxib (NSAID, selective for Cox-2) at the times 0800 and 1700 hours and 0.5% Natrosol at 1300 hours.

group 4 ("Roflumilast group"): Six male Wistar rats were given a daily dosage of 0.5% Natrosol (Placebo) in each case at the times 0800 and 1700 hours and 10 mg/kg Roflumilast (PDE4 inhibitor) at 1300 hours.

group 5 ("Roflumilast+SC-560 group"): Six male Wistar rats were given a daily dosage of in each case 2 mg/kg SC-560 (NSAID, selective for COX-1) at the times 0800 and 1700 hours and 10 mg/kg Roflumilast (PDE4 inhibitor) at 1300 hours.

group 6 ("Roflumilast+Lumiracoxib group"): Six male Wistar rats were given a daily dosage of in each case 2 mg/kg Lumiracoxib (NSAID, selective for COX-2) at the times 0800 and 1700 hours and 10 mg/kg Roflumilast (PDE4 inhibitor) at 1300 hours. For pharmacokinetic analysis (determining plasma levels of the substances) one rat from each group was used on day 4; these rats were no longer available for the investigation of other parameters.

During the experiment the body weights of the animals were determined and the differences in the body weights of the rats from the different groups were given at the end of the experiment as a change in % based on the 1st administration time (=day 1, 0800 (=time $t_0$)). The average value±standard deviation in the body weights at time $t_0$ was 306±11 g. At the end of the experiment (day 5, 95 hours after $t_0$ ($t_0$=time of the first administration on day 1, 0800)) the proportion of neutrophils (in % of white blood cells, FIG. 2) were determined from the blood of 4 or 5 of the rats from the individual groups. In addition, the weights of the animals' spleens were measured and the mesenteries were dissected for histopathological investigation for vasculitis (multifocal perivascular mononuclear/polymorphonuclear infiltration).

Figure 5:
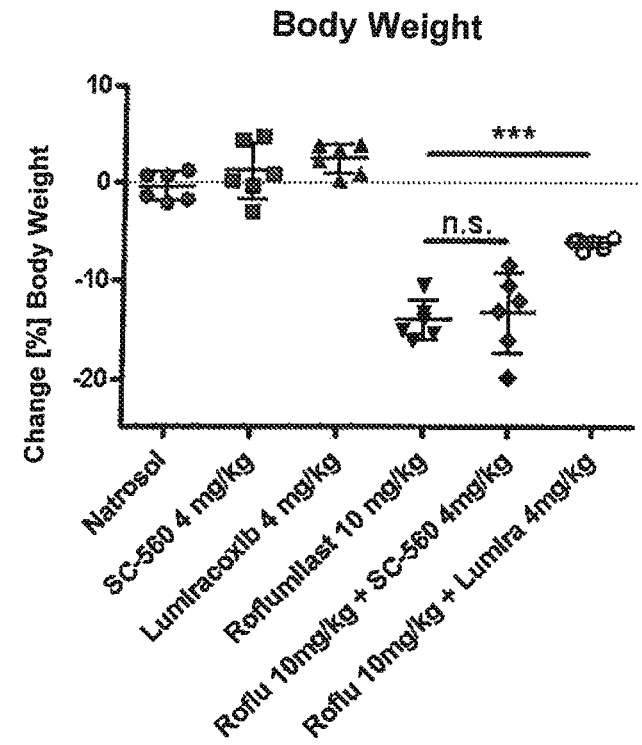

FIG. 5 shows the change in the body weight measured after the respective administrations to the control (Natrosol) group, the SC 560 group, the Lumiracoxib group, the Roflumilast group, the Roflumilast+SC 560 group and the Roflumilast+Lumiracoxib group (statistics: One-way analysis of variance; ns=not significant; *=p<0.05; ***=p<0.001).

Figure 6:
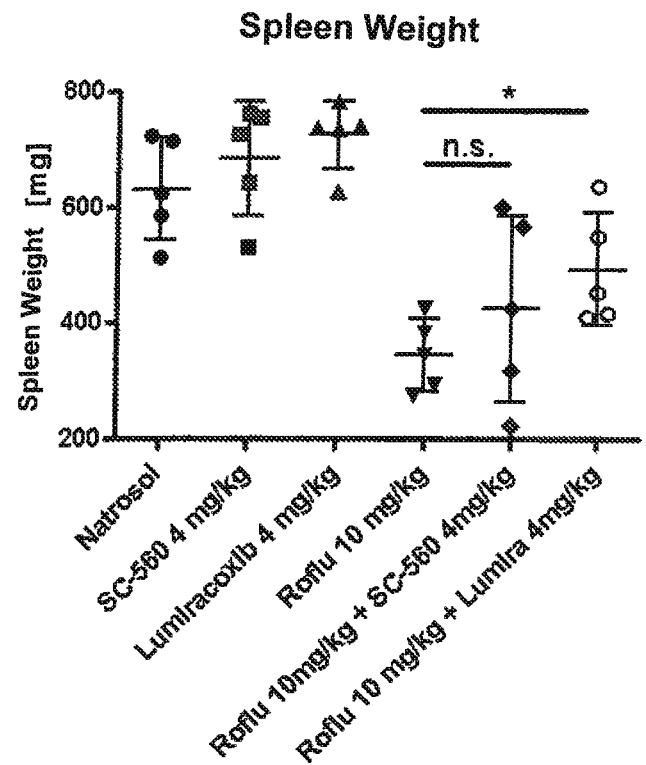

FIG. 6 shows the change in the spleen weight measured after the respective administrations to the control (Natrosol) group, the SC 560 group, the Lumiracoxib group, the Roflumilast group, the Roflumilast+SC 560 group and the Roflumilast+Lumiracoxib group (statistics: One-way analysis of variance; ns=not significant; *=p<0.05; ***=p<0.001).

Figure 7:
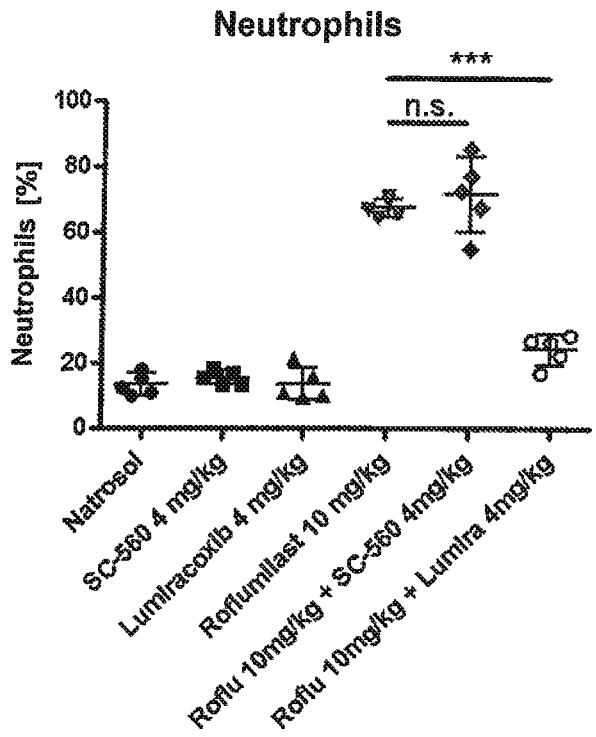

FIG. 7 shows the percentage of neutrophils measured in the blood after the respective administrations to the control (Natrosol) group, the SC 560 group, the Lumiracoxib group, the Roflumilast group, the Roflumilast+SC 560 group and the Roflumilast+Lumiracoxib group (statistics: One-way analysis of variance; ns=not significant; *=p<0.05; ***=p<0.001).

Figure 8:
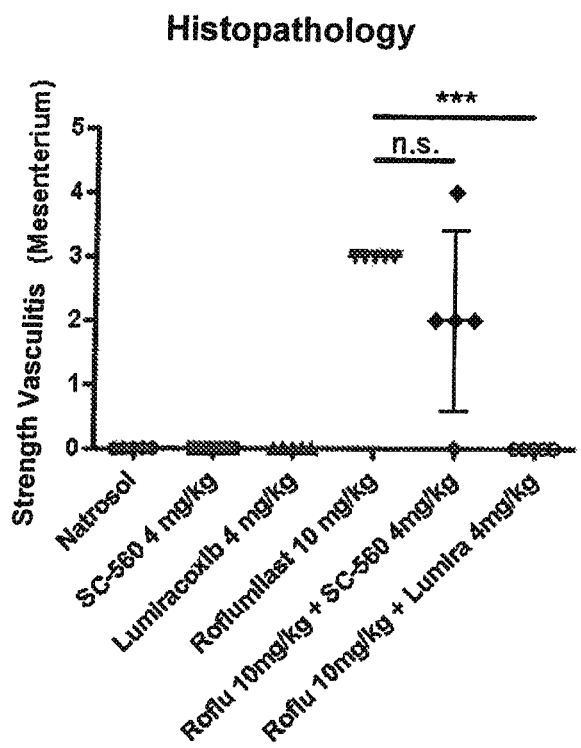

FIG. 8 shows the increase in the vasculitis observed in the mesentery after the respective administrations to the control (Natrosol) group, the 560 group, the Lumiracoxib group, the Roflumilast group, the Roflumilast+SC 560 group and the Roflumilast+Lumiracoxib-group (statistics: One-way analysis of variance; ns=not significant; *=p<0.05; ***=p<0.001).

To summarise, it can be stated that the PDE4 inhibitor-mediated side effects observed in the Roflumilast group such as loss of body weight (FIG. 5), loss of spleen weight (FIG. 6), neutrophilia (FIG. 7) and mesenteric vasculitis (monocyte/polymorphonuclear perivascular infiltration into the mesentery as a measurement of vasculitis, FIG. 8) can be substantially reduced or prevented (may even be reduced almost to the levels for the control group), if a COX-2-selective NSAID such as Lumiracoxib is co-administered simultaneously or only offset by a few hours (see Roflumilast+Lumiracoxib).

The COX-1 selective NSAID SC-560 has no protective effect on loss of body weight, loss of spleen weight, neutrophilia and the monocyte/polymorphonuclear perivascular infiltration as a measurement of vasculitis. The parameters measured after the administration of SC-560 or Lumiracoxib on its own appeared to be very similar to the control groups.

All in all it can be concluded that the protective effect of an NSAID on the PDE4-inhibitor-mediated side effects is based on inhibiting COX-2.

On the one hand, during the treatment of COPD and asthma patients with a PDE4 inhibitor the simultaneous administration of a COX-2 inhibitor such as Lumiracoxib for example has major advantages, as the NSAID can substantially reduce or even prevent the PDE4-receptor-mediated side effects, and on the other hand, no potent gastrointestinal side effects need to be feared from the COX-2 inhibitor (as is the case with NSAIDs). On the other hand, however, it has long been known that COX-2 inhibitors such as Lumiracoxib when taken regularly have cardiovascular side effects (myocardial infarction, thromboses, stroke) (cf. Clark et al; The Journal of Pharmacology and Experimental Therapeutics; 325; p. 425-434). However, it would be necessary to take these NSAIDs regularly in order to reduce the PDE4-mediated side effects, as the treatment of COPD and asthma patients with PDE4-inhibitors generally constitutes long-term therapy. Consequently, the question arises regarding alternatives to the PDE4 inhibitor/COX-2 inhibitor combined therapy which have a lower side effect profile.

Experiment 3: The EP4-receptor-selective inhibitor MF498 (N-{[4-(5,9-diethoxy-6-oxo-6,8-dihydro-7H-pyrrolo(3,4-g)quinolin-7-yl)-3-methylbenzyl)sulphonyl}-2-(2-methoxyphenyl)acetamide, also referred to as compound 2.1) protects against Roflumilast-mediated effects such as loss of body weight, loss of spleen weight, neutrophilia and mesenteric vasculitis Six male Wistar rats per group were treated for four days with the following substances (all substances are given p.o.=orally):

group 1 ("control group"): Six male Wistar rats were given a daily dosage of 0.5% Natrosol (Placebo) at 1300 hours.

group 2 ("MF-498 group"): Six male Wistar rats were given a daily dosage of 20 mg/kg MF-498 (EP4 antagonist) in each case at 1300 hours.

group 3 ("Roflumilast group"): Six male Wistar rats were given a daily dosage of 10 mg/kg Roflumilast (PDE4 inhibitor) at 1300 hours.

group 4 ("Roflumilast+MF-498 group"): Six male Wistar rats were given a daily dosage of 20 mg/kg MF-498 (EP4 antagonist) and 10 mg/kg Roflumilast (PDE4 inhibitor) at 1300 hours.

For pharmakokinetic analyses (determining the plasma levels of the substances) one rat per group was used on day 4; these rats were no longer available for other parameters under investigation.

During the experiment the body weights of the animals were determined and the differences in the body weights of the rats from the different groups at the end of the experiment were shown as a percentage change from the time of the first administration (=day 1, 0800 hours (=time $t_0$)). The average±standard deviation of the body weights at time $t_0$ was 283±6 g. At the end of the experiment (day 5, 95 hours after $t_0$ ($t_0$=the time of the first administration on day 1, 0800)) the proportion of neutrophils (in % of white blood cells, FIG. 2) were determined from the blood of 4 or 5 of the rats from the individual groups. In addition, the weights of the animals' spleens were measured and the mesenteries were dissected for histopathological investigation for vasculitis (multifocal perivascular mononuclear/polymorphonuclear infiltration).

Figure 9:
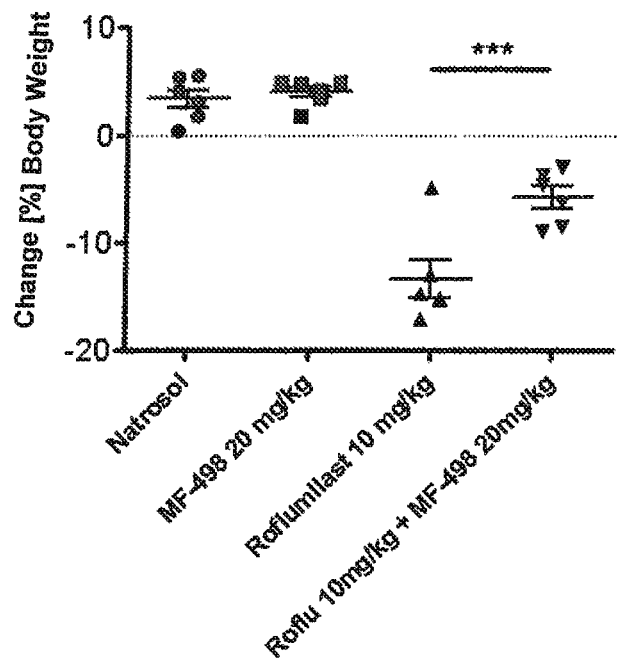

FIG. 9 shows the change in the body weight measured after the respective administrations to the control (Natrosol) group, the MF-498 group, the Roflumilast group and the Roflumilast+MF-498 group (statistics: Two-way analysis of variance; ns=nicht significant; =p<0.01, *=p<0.001).

Figure 10:
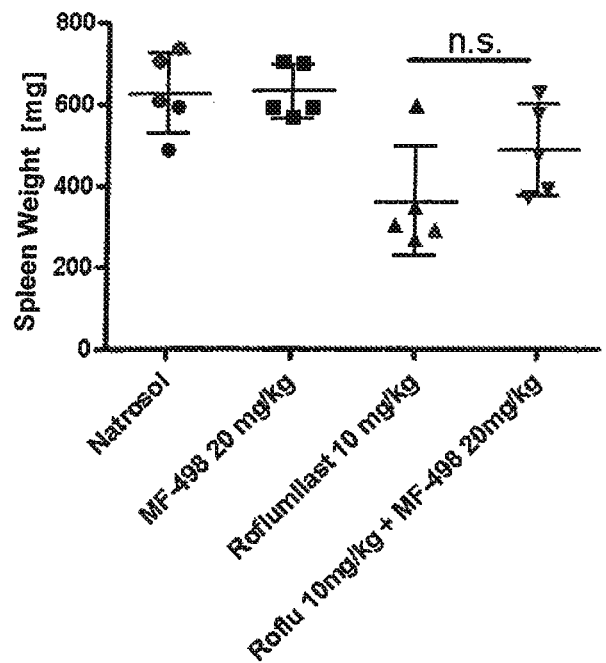

FIG. 10 shows the change in the spleen weight measured after the respective administrations in the control (Natrosol) group, the MF-498 group, the Roflumilast group and the Roflumilast+MF-498 group (statistics: Two-way analysis of variance; ns=not significant; =p<0.01, *=p<0.001).

Figure 11:
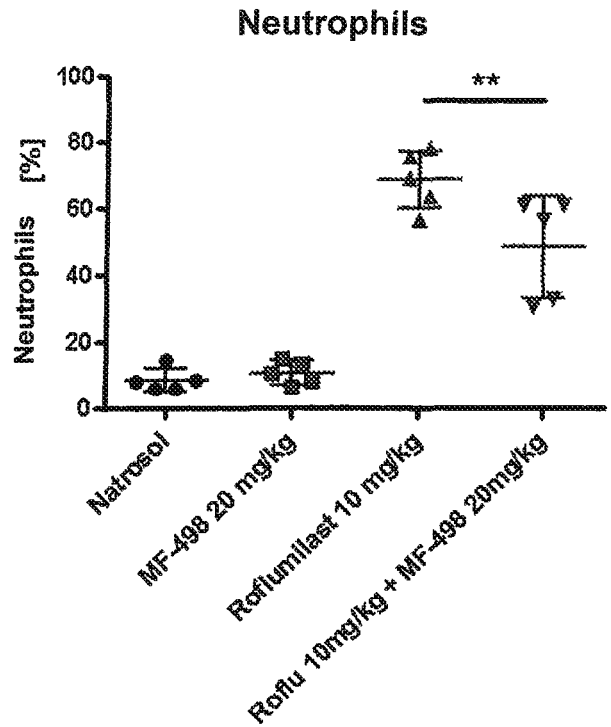

FIG. 11 shows the percentage of neutrophils in the blood after the respective administrations to the control (Natrosol) group, the MF-498 group, the Roflumilast group and the Roflumilast+MF-498 group (statistics: Two-way analysis of variance; ns=not significant; =p<0.01, *=p<0.001).

Figure 12:
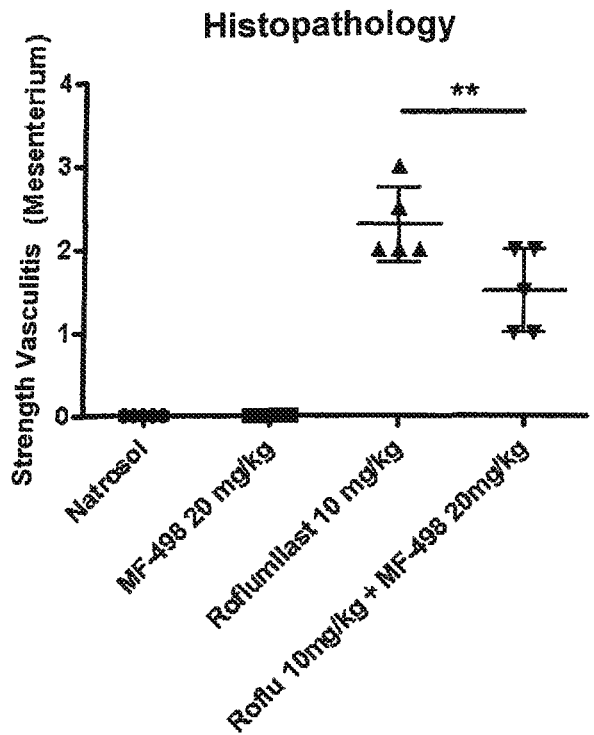

FIG. 12 shows the increase in the vasculitis observed in the mesentery after the respective administrations to the control (Natrosol) group, the MF-498 group, the Roflumilast group and the Roflumilast+MF-498 group (statistics: Two-way analysis of variance; ns=not significant; =p<0.01, *=p<0.001).

To summarise, it can be stated that the PDE4 inhibitor-mediated side effects observed in the Roflumilast group such as loss of body weight (FIG. 9), loss of spleen weight (FIG. 10), neutrophilia (FIG. 11) and mesenteric vasculitis (monocyte/polymorphonuclear perivascular infiltration into the mesentery as a measurement of vasculitis, FIG. 12) can be substantially reduced if a selective EP4 antagonist is co-administered simultaneously (see Roflumilast+MF-498). The differences in the weight of the spleen between the Roflumilast group and the Roflumilast+MF-498 group do not achieve statistical significance, as in this experiment an animal displayed an unusually small loss of spleen weight in the Roflumilast group. The parameters measured after the administration of MF-498 on its own appeared to be very similar to the control group.

All in all it can be concluded that the protective effect of an NSAID or a COX-2 inhibitor on the PDE4-inhibitor-mediated side effects is based at least partly on reducing the prostaglandin E2 synthesis of the COX-2 enzyme, which mediates the side effects through the EP4 receptor further on down the signal chain. Therefore the side effects can also be reduced by blocking the EP4 receptor. What is important in this context is that the EP4 receptor itself signals into the cell through an increase in the messenger molecule cAMP and cAMP is the substrate for the PDE4 enzymes that are inhibited by roflumilast. Therefore the influence of the PDE4 inhibitor is doubled, firstly resulting from the increase in the expression of cyclooxygenase-2, and concomitantly with that an increased production of prostaglandin E2 (PGE2) and at the same time an intensification of the PGE2/EP4-mediated signal (cAMP) in the affected cells as a result of the prevention of cAMP degradation.

Experiment 4: The EP2-receptor-preferential inhibitor AH6809
(6-isopropoxy-9-oxoxanthene-2-carboxylic acid), does not protect against Roflumilast-mediated effects such as loss of body weight, loss of spleen weight, neutrophilia and mesenteric vasculitis Six male Wistar rats per group were treated for four days with the following substances (all substances are given p.o.=orally):

group 1 ("control group"): Six male Wistar rats were given a daily dosage of 0.5% Natrosol (Placebo) at 1300 hours.

group 2 ("AH-6809 group"): Six male Wistar rats were given a daily dosage of 10 mg/kg AH-6809 (preferential EP2 antagonist) at 1300 hours.

group 3 ("Roflumilast group"): Six male Wistar rats were given a daily dosage of 10 mg/kg Roflumilast (PDE4 inhibitor) at 1300 hours.

group 4 ("Roflumilast+AH-6809 group"): Six male Wistar rats were given a daily dosage of mg/kg AH-6809 (preferential EP2 antagonist) and 10 mg/kg Roflumilast (PDE4 inhibitor) at 1300 hours.

For pharmakokinetic analyses (determining the plasma levels of the substances) one rat per group was used on day 4; these rats were no longer available for other parameters under investigation.

During the experiment the body weights of the animals were determined and the differences in the body weights of the rats from the different groups at the end of the experiment were shown as a percentage change from the time of the first administration (=day 1, 0800 hours (=time $t_0$)). The average±standard deviation of the body weights at time $t_0$ was 284±9 g. At the end of the experiment (day 5, 95 hours after $t_0$ ($t_0$=the time of the first administration on day 1, 0800)) the proportion of neutrophils (in % of white blood cells, FIG. 2) were determined from the blood of 4 or 5 of the rats from the individual groups. In addition, the weights of the animals' spleens were measured and the mesenteries were dissected for histopathological investigation for vasculitis (multifocal perivascular mononuclear/polymorphonuclear infiltration).

Figure 13:
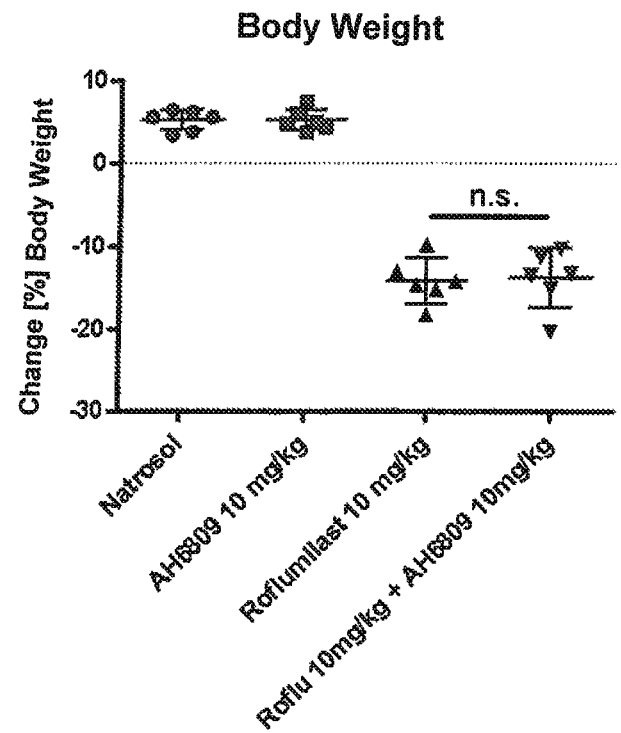

FIG. 13 shows the change in the body weight measured after the respective administrations in the control (Natrosol) group, the AH6809 group, the Roflumilast group and the Roflumilast+AH6809 group (statistics: Two-way analysis of variance; ns=not significant).

Figure 14:
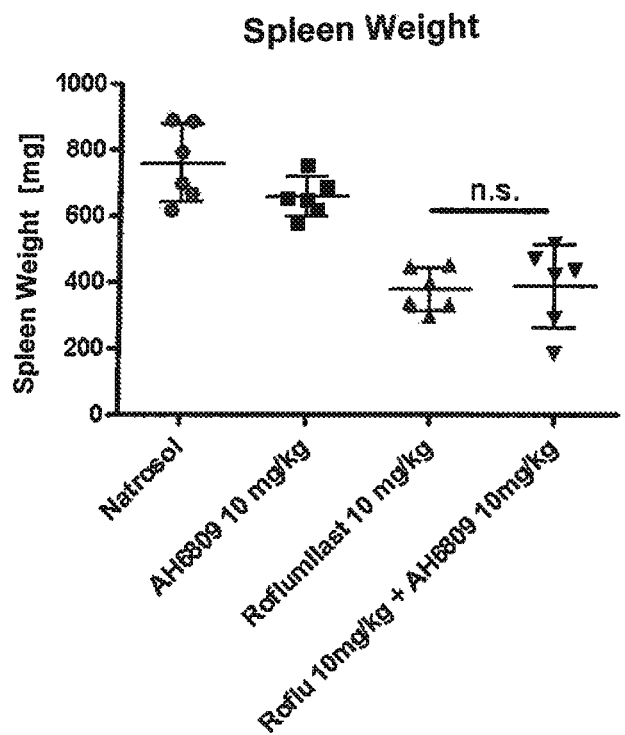

FIG. 14 shows the change in the spleen weight measured after the respective administrations in the control (Natrosol) group, the AH6809 group, the Roflumilast group and the Roflumilast+AH6809 group (statistics: Two-way analysis of variance; ns=not significant).

Figure 15:
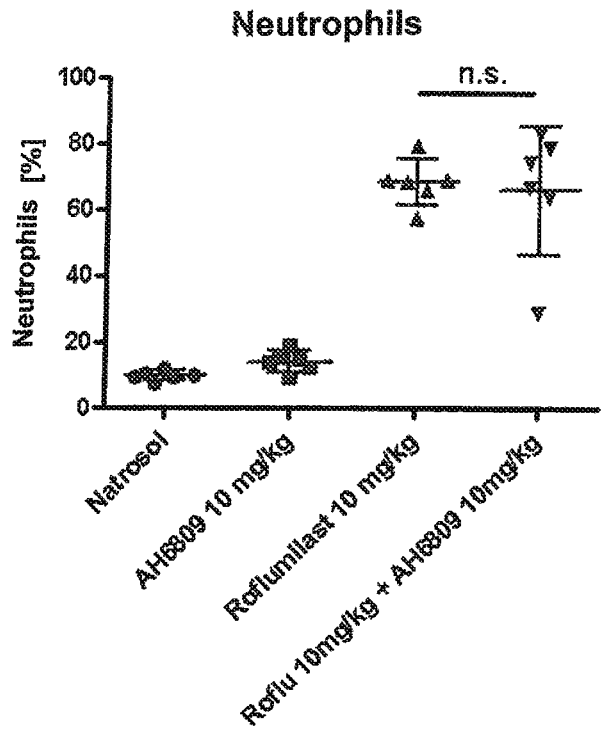

FIG. 15 shows the percentage of neutrophils in the blood after the respective administrations in the control (Natrosol) group, the AH6809 group, the Roflumilast group and the Roflumilast+AH6809 group (statistics: Two-way analysis of variance; ns=not significant).

Figure 16:
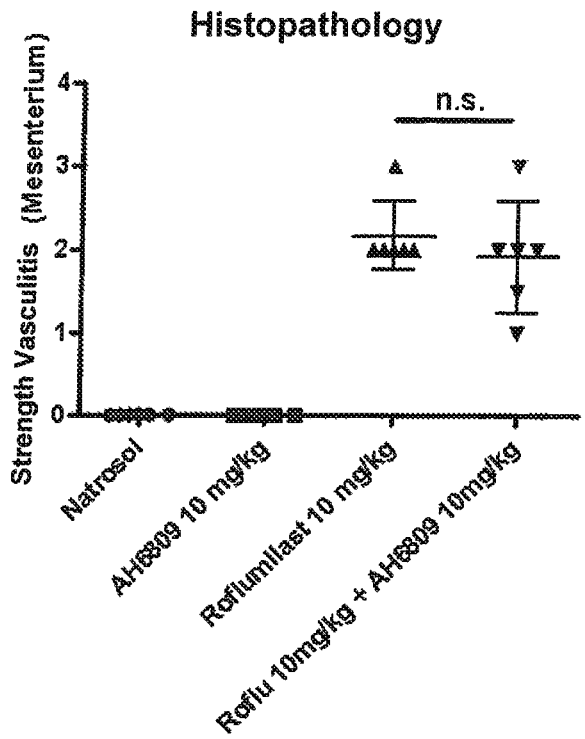

FIG. 16 shows the increase in the vasculitis observed in the mesentery after the respective administrations in the control (Natrosol) group, the AH6809 group, the Roflumilast group and the Roflumilast+AH6809 group (statistics: Two-way analysis of variance; ns=not significant).

To summarise, it can be stated that there were no indications that the EP2 preferential receptor antagonist AH-809 had any influence on the PDE4 inhibitor-mediated side effects observed in the Roflumilast group such as loss of body weight (FIG. 13), loss of spleen weight (FIG. 14), neutrophilia (FIG. 15) and mesenteric vasculitis (monocyte/polymorphonuclear perivascular infiltration in the mesentery as a measurement of vasculitis, FIG. 16). The parameters measured after the administration of AH6809 on its own appeared to be very similar to the control group.

All in all it can be concluded that the protective effect of an NSAID or a COX-2 inhibitor on the PDE4-inhibitor-mediated side effects is based at least partly on reducing the prostaglandin E2 synthesis of the COX-2 enzyme, which mediates the side effects through the EP4 receptor further on down the signal chain. Therefore the side effects can also be reduced by blocking the EP4 receptor. What is important in this context is that the EP4 receptor itself signals into the cell through an increase in the messenger molecule cAMP and cAMP is the substrate for the PDE4 enzymes that are inhibited by roflumilast. Therefore the influence of the PDE4 inhibitor is doubled, firstly resulting from the increase in the expression of cyclooxygenase-2, and concomitantly with that an increased production of prostaglandin E2 (PGE2) and at the same time an intensification of the PGE2/EP4-mediated signal (cAMP) in the affected cells as a result of the prevention of cAMP degradation. Blockage of the second cAMP-coupled prostaglandin E2 receptor EP2 by the EP2 preferential antagonist AH-6809 shows no effect on the parameters measured, in this context.

Thus, in the treatment of COPD and asthma patients with a PDE4 inhibitor, the simultaneous administration of an EP4 receptor antagonist such as MP498, for example, has major advantages, as on the one hand this EP4-receptor-antagonist can substantially reduce or even prevent the PDE4-receptor-mediated side effects and on the other hand, when an EP4 receptor antagonist is administered, in contrast to NSAID and COX-2 inhibitors, no appreciable side effects of its own are to be expected, even in long-term therapy.

Formulations

The active substance combinations of 1 and 2 are preferably administered orally. For this purpose the ingredients (1) and (2) have to be presented in suitable oral preparations.

Suitable oral forms for administration are for example tablets, capsules, solutions, syrups or emulsions. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension.

It is particularly preferable if the preparations are administered once or twice a day. Suitable tablets may be obtained, for example, by mixing the active substance(s) with known excipients, for example inert diluents such as calcium carbonate, calcium phosphate, microcrystalline cellulose, sorbitol, mannitol, isomaltose or lactose, disintegrants such as corn starch, crosslinked polyvinyl pyrrolidone, crosslinked sodium carboxymethylcellulose, sodium starch glycolate or alginic acid, binders such as starch, hydroxypropylmethylcellulose, polyvinylpyrrolidone or gelatine, lubricants, such as magnesium stearate or talc, and/or agents for delaying release, such as hydroxypropylcellulose, hydroxypropylmethylcellulose, ethylcellulose, aminomethacrylate, polyvinylpyrrolidone-polyvinylacetate copolymer, carboxymethylcellulose or polyvinylacetate. The tablets may also comprise several layers.

Coated tablets or film-coated tablets may be prepared accordingly by coating cores produced analogously to the tablets with substances normally used for tablet or film coatings, for example collidone or shellac, gum arabic, talc, titanium dioxide, sugar, hydroxypropylmethyl cellulose, ethylcellulose, cellulose acetate phthalate, polymethacrylate, polyethyleneglycol, polyvinylalcohol, polyvinylalcohol-polyethyleneglycol copolymers or polyvinylacetate. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

Examples of Formulations:

The following formulation examples for combined formulations are intended to serve to illustrate the invention without restricting it thereto. In particular, the active substances 1 and 2 may also be present in separate formulations and administered separately within a time window of not more than 6 hours.

| 1) | 5.00 mg | active substance 2.1 |
|---|---|---|
| | 25.00 mg | lactose |
| | 202.40 mg | microcrystalline cellulose |
| | 7.50 mg | polyvinylpyrrolidone |
| | 7.50 mg | crosslinked polyvinylpyrrolidone |
| | 2.50 mg | magnesium stearate |
| | 250 mg | |

| 2) | 0.10 mg | active substance 1 |
|---|---|---|
| | 6.00 mg | active substance 2.1 |
| | 25.00 mg | lactose |
| | 201.40 mg | microcrystalline cellulose |
| | 7.50 mg | crosslinked polyvinylpyrrolidone |
| | 7.50 mg | polyvinylpyrrolidone |
| | 2.50 mg | magnesium stearate |
| | 250 mg | |

| 3) | 0.10 mg | active substance 1 |
|---|---|---|
| | 7.00 mg | active substance 2.1 |
| | 25.00 mg | lactose |
| | 200.40 mg | microcrystalline cellulose |
| | 7.50 mg | crosslinked polyvinylpyrrolidone |
| | 7.50 mg | polyvinylpyrrolidone |
| | 2.50 mg | magnesium stearate |
| | 250 mg | |

| 4) | 0.10 mg | active substance 1 |
|---|---|---|
| | 8.00 mg | active substance 2.1 |
| | 25.00 mg | lactose |
| | 199.40 mg | microcrystalline cellulose |
| | 7.50 mg | crosslinked polyvinylpyrrolidone |
| | 7.50 mg | polyvinylpyrrolidone |
| | 2.50 mg | magnesium stearate |
| | 250 mg | |

| 5) | 0.10 mg | active substance 1 |
|---|---|---|
| | 9.00 mg | active substance 2.1 |
| | 25.00 mg | lactose |
| | 198.40 mg | microcrystalline cellulose |
| | 7.50 mg | crosslinked polyvinylpyrrolidone |
| | 7.50 mg | polyvinylpyrrolidone |
| | 2.50 mg | magnesium stearate |
| | 250 mg | |

| 6) | 0.50 mg | active substance 1 |
|---|---|---|
| | 25.00 mg | active substance 2.1 |
| | 25.00 mg | lactose |
| | 182.00 mg | microcrystalline cellulose |
| | 7.50 mg | polyvinylpyrrolidone |
| | 7.50 mg | crosslinked polyvinylpyrrolidone |
| | 2.50 mg | magnesium stearate |
| | 250 mg | |

| 7) | 0.50 mg | active substance 1 |
|---|---|---|
| | 30.00 mg | active substance 2.1 |
| | 25.00 mg | lactose |
| | 177.00 mg | microcrystalline cellulose |
| | 7.50 mg | crosslinked polyvinylpyrrolidone |
| | 7.50 mg | polyvinylpyrrolidone |
| | 2.50 mg | magnesium stearate |
| | 250 mg | |

| 8) | 0.50 mg | active substance 1 |
|---|---|---|
| | 35.00 mg | active substance 2.1 |
| | 25.00 mg | lactose |
| | 172.00 mg | microcrystalline cellulose |
| | 7.50 mg | crosslinked polyvinylpyrrolidone |
| | 7.50 mg | polyvinylpyrrolidone |
| | 2.50 mg | magnesium stearate |
| | 250 mg | |

| 9) | 0.50 mg | active substance 1 |
|---|---|---|
| | 40.00 mg | active substance 2.1 |
| | 25.00 mg | lactose |
| | 167.00 mg | microcrystalline cellulose |
| | 7.50 mg | crosslinked polyvinylpyrrolidone |
| | 7.50 mg | polyvinylpyrrolidone |
| | 2.50 mg | magnesium stearate |
| | 250 mg | |

| 10) | 0.50 mg | active substance 1 |
|---|---|---|
| | 45.00 mg | active substance 2.1 |
| | 25.00 mg | lactose |
| | 162.00 mg | microcrystalline cellulose |
| | 7.50 mg | crosslinked polyvinylpyrrolidone |
| | 7.50 mg | polyvinylpyrrolidone |
| | 2.50 mg | magnesium stearate |
| | 250 mg | |

| 11) | 1.00 mg | active substance 1 |
|---|---|---|
| | 50.00 mg | active substance 2.1 |
| | 25.00 mg | lactose |
| | 156.50 mg | microcrystalline cellulose |
| | 7.50 mg | polyvinylpyrrolidone |
| | 7.50 mg | crosslinked polyvinylpyrrolidone |
| | 2.50 mg | magnesium stearate |
| | 250 mg | |

| 12) | 1.00 mg | active substance 1 |
|---|---|---|
| | 60.00 mg | active substance 2.1 |
| | 25.00 mg | lactose |
| | 146.50 mg | microcrystalline cellulose |
| | 7.50 mg | crosslinked polyvinylpyrrolidone |
| | 7.50 mg | polyvinylpyrrolidone |
| | 2.50 mg | magnesium stearate |
| | 250 mg | |

| 13) | 1.00 mg | active substance 1 |
|---|---|---|
| | 70.00 mg | active substance 2.1 |
| | 25.00 mg | lactose |
| | 136.50 mg | microcrystalline cellulose |
| | 7.50 mg | crosslinked polyvinylpyrrolidone |
| | 7.50 mg | polyvinylpyrrolidone |
| | 2.50 mg | magnesium stearate |
| | 250 mg | |

| 14) | 1.00 mg | active substance 1 |
|---|---|---|
| | 80.00 mg | active substance 2.1 |
| | 25.00 mg | lactose |
| | 126.50 mg | microcrystalline cellulose |
| | 7.50 mg | crosslinked polyvinylpyrrolidone |
| | 7.50 mg | polyvinylpyrrolidone |
| | 2.50 mg | magnesium stearate |
| | 250 mg | |

| 15) | 1.00 mg | active substance 1 |
| --- | --- | --- |
| | 90.00 mg | active substance 2.1 |
| | 25.00 mg | lactose |
| | 116.50 mg | microcrystalline cellulose |
| | 7.50 mg | crosslinked polyvinylpyrrolidone |
| | 7.50 mg | polyvinylpyrrolidone |
| | 2.50 mg | magnesium stearate |
| | 250 mg | |

| 16) | 5.00 mg | active substance 1 |
| --- | --- | --- |
| | 250.00 mg | active substance 2.1 |
| | 50.00 mg | lactose |
| | 160.00 mg | microcrystalline cellulose |
| | 15.00 mg | polyvinylpyrrolidone |
| | 15.00 mg | crosslinked polyvinylpyrrolidone |
| | 5.00 mg | magnesium stearate |
| | 500 mg | |

| 17) | 5.00 mg | active substance 1 |
| --- | --- | --- |
| | 300.00 mg | active substance 2.1 |
| | 50.00 mg | lactose |
| | 110.00 mg | microcrystalline cellulose |
| | 15.00 mg | crosslinked polyvinylpyrrolidone |
| | 15.00 mg | polyvinylpyrrolidone |
| | 5.00 mg | magnesium stearate |
| | 500 mg | |

| 18) | 5.00 mg | active substance 1 |
| --- | --- | --- |
| | 350.00 mg | active substance 2.1 |
| | 50.00 mg | lactose |
| | 60.00 mg | microcrystalline cellulose |
| | 15.00 mg | crosslinked polyvinylpyrrolidone |
| | 15.00 mg | polyvinylpyrrolidone |
| | 5.00 mg | magnesium stearate |
| | 500 mg | |

| 19) | 5.00 mg | active substance 1 |
| --- | --- | --- |
| | 400.00 mg | active substance 2.1 |
| | 60.00 mg | lactose |
| | 93.00 mg | microcrystalline cellulose |
| | 18.00 mg | crosslinked polyvinylpyrrolidone |
| | 18.00 mg | polyvinylpyrrolidone |
| | 6.00 mg | magnesium stearate |
| | 600 mg | |

| 20) | 5.00 mg | active substance 1 |
| --- | --- | --- |
| | 450.00 mg | active substance 2.1 |
| | 60.00 mg | lactose |
| | 43.00 mg | microcrystalline cellulose |
| | 18.00 mg | crosslinked polyvinylpyrrolidone |
| | 18.00 mg | polyvinylpyrrolidone |
| | 6.00 mg | magnesium stearate |
| | 600 mg | |

The invention claimed is:

1. A medicament comprising an EP4 receptor antagonist and a PDE4 inhibitor of formula 1

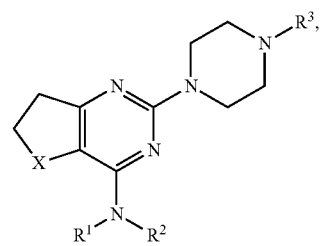

wherein:

X is SO or $SO_2$;

$R^1$ is H, $C_{1-6}$-alkyl;

$R^2$ is H or a group selected from $C_{1-10}$-alkyl and $C_{2-6}$-alkenyl, each optionally substituted by one or more groups selected from halogen and $C_{1-3}$-fluoroalkyl or optionally substituted by one or more groups selected from $OR^{2.1}$, $COOR^{2.1}$, $CONR^{2.2}R^{2.3}$, $SR^{2.1}$, $SO-R^{2.1}$, $SO_2-R^{2.1}$, $C_{6-10}$-aryl, a het, a hetaryl, a mono- or bicyclic $C_{3-10}$-cycloalkyl, $CH_2-NR^{2.2}R^{2.3}$, and $NR^{2.2}R^{2.3}$, each optionally be substituted by one or more groups selected from OH, halogen, $OR^{2.1}$, oxo, $CF_3$, $CHF_2$, $CH_2F$, $C_{1-6}$-alkyl, $C_{1-6}$-alkanol, $C_{6-10}$-aryl, $COOR^{2.1}$, $CH_2-NR^{2.2}R^{2.3}$, and $NR^{2.2}R^{2.3}$, wherein $R^{2.1}$ is H or a group selected from $C_{1-6}$-alkyl, $C_{1-6}$-alkanol, $C_{1-3}$-haloalkyl, mono- or bicyclic $C_{3-10}$-cycloalkyl, $C_{6-10}$-aryl-$C_{1-6}$-alkylene, mono- or bicyclic hetaryl-$C_{1-6}$-alkylene, het-$C_{1-6}$-alkylene, $C_{3-10}$-cycloalkyl-$C_{1-6}$-alkylene, a mono- or bicyclic $C_{6-10}$-aryl, a hetaryl, and a het, each optionally substituted by one or more groups selected from OH, O—($C_{1-3}$-alkyl), halogen, $C_{1-6}$-alkyl, and $C_{6-10}$-aryl, wherein $R^{2.2}$ and $R^{2.3}$ are independently H or a group selected from $C_{1-6}$-alkyl, mono- or bicyclic $C_{3-10}$ cycloalkyl, $C_{6-10}$-aryl-$C_{1-6}$-alkylene, hetaryl-$C_{1-6}$-alkylene, mono- or bicyclic $C_{6-10}$-aryl, het, hetaryl, $CO-NH_2$, $CO-NHCH_3$, $CO-N(CH_3)_2$, $SO_2-(C_1-C_2$-alkyl), $CO-R^{2.1}$, and $COOR^{2.1}$, each optionally substituted by one or more groups selected from OH, halogen, $C_{1-6}$-alkyl, $C_{6-10}$-aryl, and $COOR^{2.1}$, wherein het is a three- to eleven-membered, mono- or bicyclic, saturated or partly saturated, optionally annellated or optionally bridged heterocyclic group, which contains 1, 2, 3, or 4 heteroatoms independently selected from N, S, or O, hetaryl is a five- to eleven-membered, mono- or bicyclic, optionally annellated heteroaryl, which contains 1, 2, 3, or 4 heteroatoms independently selected from N, S, or O, and cycloalkyl is saturated or partly saturated, or $R^2$ is a mono- or polycyclic $C_{3-10}$ cycloalkyl optionally singly or multiply bridged by $C_{1-3}$-alkyl groups and which is optionally substituted by a group selected from branched or unbranched $C_{1-6}$-alkanol, $C_{1-3}$-fluoroalkyl, $C_{1-3}$-alkylene-$OR^{2.1}$, $OR^{2.1}$, $COOR^{2.1}$, $SO_2-NR^{2.2}R^{2.3}$, het, $C_{6-10}$-aryl, $C_{1-6}$-alkyl, $C_{6-10}$-aryl-$C_{1-6}$-alkylene, hetaryl-$C_{1-6}$-alkylene, mono- or bicyclic $C_{3-10}$ cycloalkyl, and $NR^{2.2}R^{2.3}$, each optionally substituted by one or more groups selected from OH, $OR^{2.1}$, oxo, halogen, $CF_3$, $CHF_2$, $CH_2F$, $C_{1-6}$-alkyl, $C_{6-10}$-aryl, and $NR^{2.2}R^{2.3}$, or $R^2$ is a mono- or polycyclic $C_{6-10}$-aryl optionally substituted by OH, SH, or halogen or by one or more groups selected from $OR^{2.1}$, $COOR^{2.1}$, $NR^{2.2}R^{2.3}$, $CH_2$—$NR^{2.2}R^{2.3}$, $C_{3-10}$-cycloalkyl, het, —$C_{1-6}$-alkyl, $C_{1-3}$-fluoroalkyl, $C_{6-10}$-aryl-$C_{1-6}$-alkylene, het-$C_{1-6}$-alkylene, hetaryl-$C_{1-6}$-alkylene, $C_{6-10}$-aryl, $SO_2$—$CH_3$, $SO_2$—$CH_2CH_3$, and $SO_2$—$NR^{2.2}R^{2.3}$, each optionally substituted by one or more selected from OH, $OR^{2.1}$, $CF_3$, $CHF_2$, $CH_2F$, oxo, halogen, $CF_3$, $CHF_2$, $CH_2F$, $C_{1-6}$-alkyl, $C_{6-10}$-aryl, and $NR^{2.2}R^{2.3}$, or $R^2$ is a group selected from het and hetaryl, each optionally substituted by one or more groups selected from halogen, OH, oxo, $CF_3$, $CHF_2$ and $CH_2F$ or by one or more groups selected from $OR^{2.1}$, $C_{1-3}$-alkylene-$OR^{2.1}$, $SR^{2.1}$, SO—$R^{2.1}$ and $SO_2$—$R^{2.1}$, $COOR^{2.1}$, $COR^{2.1}$, $C_{1-6}$-alkanol, $C_{3-10}$-cycloalkyl, $C_{6-10}$-aryl, $C_{1-6}$-alkyl, $C_{6-10}$-aryl-$C_{1-6}$-alkylene, hetaryl-$C_{1-6}$-alkylene, het, hetaryl, $C_{1-3}$-alkylene-$OR^{2.1}$, and $NR^{2.2}R^{2.3}$, each optionally substituted by one or more groups selected from OH, $OR^{2.1}$, oxo, halogen, $CF_3$, $CHF_2$, $CH_2F$, $C_{1-6}$-alkyl, $C_{6-10}$-aryl, and $NR^{2.2}R^{2.3}$, or wherein $NR^1R^2$ together are a heterocyclic four- to seven-membered ring optionally bridged, which contains 1, 2, or 3 heteroatoms selected from N, O, and S and which is optionally substituted by one or more groups selected from OH, $OR^{2.1}$, $C_{1-3}$-alkylene-$O^{R.1}$, oxo, halogen, $C_{1-6}$-alkyl, $C_{6-10}$-aryl, $COOR^{2.1}$, $CH_2$—$NR^{2.2}$—COO—$R^{2.1}$, $CH_2$—$NR^{2.2}$—CO—$R^{2.1}$, $CH_2$—$NR^{2.2}$—CO—$CH_2$—$NR^{2.2}R^{2.3}$, $CH_2$—$NR^{2.2}$—$SO_2$—$C_{1-3}$-alkyl, $CH_2$—$NR^{2.2}$—$SO_2$—$NR^{2.2}R^{2.3}$, $CH_2$—$NR^{2.2}$—CO—$NR^{2.2}R^{2.3}$, CO—$NR^{2.2}R^{2.3}$, $CH_2$—$NR^{2.2}R^{2.3}$, and $NR^{2.2}R^{2.3}$, and $R^3$ is a group selected from a het and a hetaryl, each optionally substituted by one or more groups selected from halogen, $C_{1-3}$-fluoroalkyl, CN, OH, oxo, —$C_{1-6}$-alkyl, —O—$R^{2.1}$, —$COOR^{2.1}$, SO—$R^{2.1}$, $SO_2$—$R^{2.1}$, $C_{6-10}$-aryl, $C_{1-3}$-alkylene-$C_{6-10}$-aryl, —$C_{1-3}$-alkylene-$NR^{2.2}R^{2.3}$, —$NR^{2.2}R^{2.3}$, a $C_{3-10}$-cycloalkyl, a $C_{1-3}$-alkylene-$C_{3-10}$-cycloalkyl, a het, a hetaryl, $C_{1-3}$-alkylene-hetaryl, and $C_{1-3}$-alkylene-het, each optionally substituted by one or more groups selected from OH, halogen, —$C_{1-3}$-fluoroalkyl, $C_{1-6}$-alkyl, $C_{6-10}$-aryl, —COO($C_{1-3}$-alkyl), and O—($C_{1-3}$-alkyl).

2. The medicament according to claim 1, wherein the EP4-receptor antagonist is an EP4-specific antagonist.

3. The medicament according to claim 1, the EP4-receptor antagonist is:

[N-{[4-(5,9-diethoxy-6-oxo-6,8-dihydro-7H-pyrrolo[3,4-g]quinolin-7-yl)-3-methylbenzyl]sulphonyl}-2-(2-methoxyphenyl)acetamide] (2.1);

5-butyl-2,4-dihydro-4-[[2'-[N-(3-methyl-2-thiophenecarbonyl)sulphamoyl]biphenyl-4-yl]methyl]-2-[(2-trifluoromethyl)phenyl]-1,2,4-triazol-3-one (2.2);

(4-{(1S)-1-[({5-chloro-2-[(4-fluorophenyl)oxy]phenyl}carbonyl)amino]ethyl}benzoic acid (2.3);

N-[({2-[4-(2-ethyl-4,6-dimethyl-1H-imidazo[4,5-c]pyridin-1-yl)phenyl]ethyl}-amino)carbonyl]-4-methylbenzene sulphonamide (2.4);

4-[[4-(5-methoxy-2-pyridinyl)phenoxy]methyl]-5-methyl-N-[(2-methylphenyl)sulphonyl]-2-furancarboxamide (2.5);

methyl-11α,15α-dihydroxy-16-(3-methoxymethylphenyl)-9-oxo-17,18,19,20-tetranor-5-thia-13(E) prostanoate (2.6);

4-cyano-2-[[2-(4-fluoro-1-naphthalenyl)-1-oxopropyl]amino]-benzenebutanoic acid (2.7); or N-{2-[4-(4,9-diethoxy-1-oxo-1,3-dihydro-2H-benzo[f]isoindol-2-yl)phenyl]acetyl}-benzene sulphonamide (2.8).

4. The medicament according to claim 1, wherein:

X is SO;

$R^1$ is H;

$R^2$ is H or $C_{1-6}$-alkyl optionally be substituted by one or more groups selected from F, $CF_3$, $CHF_2$, or $CH_2F$ or optionally substituted by one or more groups selected from $OR^{2.1}$, $COOR^{2.1}$, $CONR^{2.2}R^{2.3}$, $SR^{2.1}$, SO—$R^{2.1}$, $SO_2$—$R^{2.1}$, phenyl, a het, a hetaryl, a monocyclic $C_{3-7}$-cycloalkyl, $CH_2$—$NR^{2.2}R^{2.3}$, and $NR^{2.2}R^{2.3}$, each optionally be substituted by one or more groups selected from OH, F, Cl, Br, $CF_3$, $CHF_2$, $CH_2F$, $OR^{2.1}$, oxo, methyl, ethyl, propyl, isopropyl, $C_{1-2}$-alkanol, phenyl, $COOR^{2.1}$, $CH_2$—$NR^{2.2}R^{2.3}$, and $NR^{2.2}R^{2.3}$, wherein $R^{2.1}$ is H or a group selected from methyl, ethyl, propyl, isopropyl, monocyclic $C_{3-7}$ cycloalkyl, phenyl-$C_{1-2}$-alkylene, hetaryl-$C_{1-2}$-alkylene, het-$C_{1-2}$-alkylene, $C_{3-7}$-cycloalkyl-$C_{1-2}$-alkylene, phenyl, a hetaryl, and a het, each optionally substituted by one or more groups selected from OH, halogen, methyl, ethyl, propyl, isopropyl, O-methyl, O-ethyl, O-propyl, O-isopropyl, and phenyl, wherein $R^{2.2}$ and $R^{2.3}$ are each independently H or a group selected from methyl, ethyl, propyl, isopropyl, monocyclic $C_{3-7}$-cycloalkyl, phenyl-$C_{1-3}$-alkylene, hetaryl-$C_{1-3}$-alkylene, phenyl, het, hetaryl, CO—$NH_2$, CO—$NHCH_3$, $CON(CH_3)_2$, $SO_2$—($C_1$-$C_2$-alkyl), CO—$R^{2.1}$, and $COOR^{2.1}$, each optionally substituted by one or more groups selected from OH, F, Cl, Br, methyl, ethyl, propyl, isopropyl, phenyl, and $COOR^{2.1}$, wherein het is a three- to seven-membered, monocyclic, saturated or partly saturated heterocyclic group which contains 1, 2, or 3 heteroatoms independently selected from N, S, or O, and wherein hetaryl is a five- to six-membered, monocyclic, aromatic heteroaryl, which contains 1, 2, or 3 heteroatoms independently selected from N, S, or O, and cycloalkyl is saturated or partly saturated, or $R^2$ is a monocyclic $C_{3-7}$ cycloalkyl optionally substituted by a group selected from branched or unbranched $C_{1-2}$-alkanol, $C_{1-3}$-fluoroalkyl, $C_{1-3}$-alkylene-$OR^{2.1}$, $OR^{2.1}$, $COOR^{2.1}$, $SO_2$—$NR^{2.2}R^{2.3}$, het, methyl, ethyl, propyl, isopropyl, phenyl, phenyl-$C_{1-2}$-alkylene, hetaryl-$C_{1-2}$-alkylene, monocyclic $C_{3-7}$ cycloalkyl, and $NR^{2.2}R^{2.3}$, each optionally substituted by one or more groups selected from OH, $OR^{2.1}$, oxo, halogen, $CF_3$, $CHF_2$, $CH_2F$, methyl, ethyl, propyl, isopropyl, phenyl, and $NR^{2.2}R^{2.3}$, or $R^2$ is a phenyl optionally substituted by OH, SH, F, Cl, or Br or by one or more groups selected from $OR^{2.1}$, $COOR^{2.1}$, $NR^{2.2}R^{2.3}$, $CH_2$—$NR^{2.2}R^{2.3}$, $C_{3-7}$-cycloalkyl, het, methyl, ethyl, propyl, isopropyl, $CF_3$, $CHF_2$, $CH_2F$, phenyl-$C_{1-2}$-alkylene, het-$C_{1-2}$-alkylene, hetaryl-$C_{1-2}$-alkylene, phenyl, $SO_2$—$CH_3$, $SO_2$—$CH_2CH_3$, and $SO_2$—$NR^{2.2}R^{2.3}$, each optionally substituted by one or more or several groups selected from OH, $OR^{2.1}$, oxo, F, Cl, Br, $CF_3$, $CHF_2$, $CH_2F$, methyl, ethyl, propyl, isopropyl, phenyl, and $NR^{2.2}R^{2.3}$, or $R^2$ is a group selected from a het and a hetaryl, each optionally substituted by one or more groups selected from F, Cl, Br, OH, oxo, $CF_3$, $CHF_2$, $CH_2F$ and SH or by one or more groups selected from $OR^{2.1}$, $C_{1-3}$-alkylene-$OR^{2.1}$, $SR^{2.1}$, SO—$R^{2.1}$, $SO_2$—$R^{2.1}$, $COOR^{2.1}$, $COR^{2.1}$, $C_{1-2}$- alkanol, $C_{3-10}$-cycloalkyl, phenyl, methyl, ethyl, propyl, isopropyl, phenyl-$C_{1-2}$-alkylene, hetaryl-$C_{1-2}$-alkylene, het, hetaryl, $C_{1-2}$-alkanol, and $NR^{2.2}R^{2.3}$, each optionally substituted by one or more groups selected from OH, $OR^{2.1}$, oxo, F, Cl, Br, $CF_3$, $CHF_2$, $CH_2F$, $C_{1-6}$-alkyl, phenyl, and $NR^{2.2}R^{2.3}$, and $R^3$ is a group selected from a saturated or partly saturated, monocyclic three- to seven-membered heterocyclic group, a saturated or partly saturated, bicyclic five- to eleven-membered heterocyclic group, a monocyclic, five- to six-membered heteroaryl, and a bicyclic, seven- to eleven-membered heteroaryl, which contains in each case 1, 2, 3, or 4 heteroatoms independently selected from N, O, and S, each optionally substituted in each case by one or more groups selected from halogen, $C_{1-3}$-fluoroalkyl, CN, OH, oxo, $C_{1-6}$ alkyl, —O—$R^{2.1}$, —$COOR^{2.1}$, SO—$R^{2.1}$, $SO_2$—$R^{2.1}$, $C_{6-10}$-aryl, $C_{1-3}$-alkylene-$C_{6-10}$-aryl, —$C_{1-3}$-alkylene-$NR^{2.2}R^{2.3}$, —$NR^{2.2}R^{2.3}$, a $C_{3-10}$-cycloalkyl, a $C_{1-3}$-alkylene-$C_{3-10}$-cycloalkyl, het, a hetaryl, $C_{1-3}$-alkylene-hetaryl, and $C_{1-3}$-alkylene-het, each optionally substituted by one or more groups selected from OH, halogen, —$C_{1-3}$-fluoroalkyl, $C_{1-6}$-alkyl, $C_{6-10}$-aryl, —$COO(C_{1-3}$-alkyl), and O—($C_{1-3}$-alkyl).

5. The medicament according to claim 4, wherein:
$R^2$ is a group according to formula 3

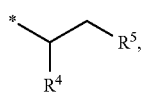

$R^5$ is OH or $NH_2$, and
$R^4$ is a group selected from $C_{1-4}$-alkyl, hetaryl, and phenyl, each optionally substituted by one or more groups selected from OH, F, Br, $OR^{2.1}$, oxo, methyl, ethyl, $C_{1-2}$-alkanol, phenyl, $COOR^{2.1}$, $CH_2$—$NR^{2.2}R^{2.3}$, and $NR^{2.2}R^{2.3}$.

6. The medicament according to claim 5, wherein:
$R^4$ is methyl, ethyl, propyl, or isopropyl.

7. The medicament according to claim 4, wherein:
$R^2$ is a monocyclic three, four, five, six, or seven-membered cycloalkyl ring optionally substituted in the spiro position by a group selected from —$CH_2$—$OR^{2.1}$, branched or unbranched $C_{2-6}$-alkylene-$OR^{2.1}$, methyl, ethyl, propyl, isopropyl, butyl, isobutyl, cyclopropyl, —$CF_3$, $CHF_2$, $CH_2F$, and $C_{2-4}$-fluoroalkyl, and
$R^{2.1}$ is methyl, ethyl, propyl, isopropyl, butyl, or isobutyl.

8. The medicament according to claim 4, wherein:
$R^2$ is a phenyl optionally substituted in one or both meta positions by one or more groups selected from methyl, ethyl, propyl, isopropyl, cyclopropyl, F, Cl, Br, OH, $OR^{2.1}$, $COOR^{2.1}$, $CF_3$, $CHF_2$, $CH_2F$, $NH_2$, and $N(CH_3)_2$, wherein $R^{2.1}$ is H, methyl or ethyl.

9. The medicament according to claim 4, wherein:
$R^2$ is a monocyclic, saturated three-, four-, five-, six-, or seven-membered heterocyclic group with 1, 2, or 3 heteroatoms selected in each case from N, O, and S, each optionally substituted by one or more groups selected from fluorine, chlorine, bromine, $CF_3$, $CHF_2$, $CH_2F$, OH, oxo, and SH or by one or more groups selected from $OR^{2.1}$, $C_{1-3}$-alkylene-$OR^{2.1}$, $SR^{2.1}$, SO—$R^{2.1}$, $SO_2$—$R^{2.1}$, $COOR^{2.1}$, $COR^{2.1}$, $C_{1-6}$-alkanol, $C_{3-10}$-cycloalkyl, phenyl, $C_{1-6}$-alkyl, phenyl-$C_{1-6}$-alkylene, hetaryl-$C_{1-6}$-alkylene, het, hetaryl, and $NR^{2.2}R^{2.3}$, each optionally substituted by one or more groups selected from OH, $OR^{2.1}$, oxo, F, Cl, $CF_3$, $CHF_2$, $CH_2F$, $C_{1-6}$-alkyl, phenyl, and $NR^{2.2}R^{2.3}$.

10. The medicament according to claim 9, wherein:
$R^2$ is a monocyclic, saturated, six-membered heterocyclic group with a heteroatom selected from N, O, and S, optionally substituted by one or more groups selected from F, Cl, Br, $CF_3$, $CHF_2$, $CH_2F$, OH, oxo, $NH_2$, $NHCH_3$, $N(CH_3)_2$, methyl, ethyl, propyl, isopropyl, cyclopropyl, methoxy, and ethoxy.

11. The medicament according to claim 10, wherein:
$R^2$ is a group selected from piperidine or tetrahydropyran, each optionally substituted by one or more groups selected from F, Cl, Br, OH, $CF_3$, $CHF_2$, $CH_2F$, $NH_2$, $NHCH_3$, $N(CH_3)_2$, oxo, methyl, and methoxy.

12. The medicament according to claim 10, wherein:
$R^3$ is a monocyclic five- or six-membered heteroaryl ring optionally substituted by one or more groups selected from F, Cl, Br, $CF_3$, $CHF_2$, $CH_2F$, CN, OH, methyl, ethyl, propyl, isopropyl, —O-methyl, O-ethyl, —COOmethyl, —COOethyl, $SO_2$—($CH_3$), SO—($CH_3$), $SO_2$—($CH_2CH_3$), SO—($CH_2CH_3$), phenyl, -methylene-phenyl, -ethylene-phenyl, —$NH_2$, —NH($CH_3$), $N(CH_3)_2$, -methylene-$NH_2$, -methylene-NH($CH_3$), -methylene-N($CH_3$)$_2$, a $C_{3-6}$-cycloalkyl, a methylene-$C_{3-6}$-cycloalkyl, a saturated or partly saturated, five- to six-membered heterocyclic group, a five- or six-membered heteroaryl, -methylene-hetaryl, and -methylene-het, each optionally substituted by one or more groups selected from OH, F, Cl, Br, $CF_3$, $CHF_2$, $CH_2F$, methyl, ethyl, propyl, isopropyl, phenyl, —$COO(CH_3)$, —O-methyl, and —O-ethyl.

13. The medicament according to claim 10, wherein:
$R^3$ is a bicyclic 9- to 11-membered saturated, unsaturated or partly saturated heterocyclic group, each optionally substituted by one or more groups selected from F, Cl, Br, $CF_3$, $CHF_2$, $CH_2F$, CN, OH, -methyl, ethyl, propyl, isopropyl, —O-methyl, O-ethyl, —COOmethyl, —COOethyl, $SO_2$—($CH_3$), SO—($CH_3$), $SO_2$—($CH_2CH_3$), SO—($CH_2CH_3$), phenyl, -methylene-phenyl, -ethylene-phenyl, —NH2, —NH($CH_3$), $N(CH_3)_2$, -methylene-$NH_2$, -methylene-NH($CH_3$), -methylene-N($CH_3$)$_2$, a —$C_{3-6}$-cycloalkyl, a -methylene-$C_{3-6}$-cycloalkyl, a saturated, partly unsaturated or unsaturated 5- to 6-membered heterocyclic group, a 5- to 6-membered heteroaryl, -methylene-hetaryl, and -methylene-het, each optionally substituted by one or more groups selected from OH, F, Cl, Br, $CF_3$, $CHF_2$, $CH_2F$, methyl, ethyl, propyl, isopropyl, phenyl, —$COO(CH_3)$, —O-methyl, and —O-ethyl.

14. The medicament according to claim 12, wherein:
$R^3$ is a monocyclic five- or six-membered heteroaryl ring selected from pyrrole, pyrazole, furan, thiophene, thiazole, imidazole, oxazole, pyridazine, pyrimidine, pyrazine, thiadiazole, oxadiazole, triazine, isoxazole, isothiazole, and pyridine, each optionally substituted by one or more groups selected from F, Cl, Br, $CF_3$, $CHF_2$, $CH_2F$, CN, OH, -methyl, ethyl, propyl, isopropyl, —O-methyl, O-ethyl, —COOmethyl, —COOethyl, $SO_2$—($CH_3$), $SO_2$—($CH_2CH_3$), phenyl, -methylene-phenyl, -ethylene-phenyl, —$NH_2$, —NH($CH_3$), $N(CH_3)_2$, -methylene-$NH_2$, -methylene-NH($CH_3$), -methylene-N($CH_3$)$_2$, a $C_{3-6}$-cycloalkyl, a methylene-$C_{3-6}$-cycloalkyl, a het, a hetaryl, -methylene-hetaryl, and -methylene-het, each optionally substituted by one or more groups selected from OH, F, Cl, Br, CF$_3$, CHF$_2$, CH$_2$F, methyl, ethyl, propyl, isopropyl, phenyl, —COO(CH$_3$), —O-methyl, and —O-ethyl.

15. The medicament according to claim 13, wherein:
R$^3$ is a bicyclic 9- to 11-membered heterocyclic group selected from benzoxazole, benzodioxole, dihydrobenzodioxin, benzodioxin, benzisoxazole, benzothiazole, benzisothiazole, thienopyrimidine, furopyrimidine, thienopyridine, furopyridine, indole, isoindole, quinoxaline, naphthyridine, pyridopyrazine, pyridopyrimidine, quinoline, isoquinoline, benzoimidazole, 6,7,8,9-tetrahydro-5H-pyrazino[2,3-d]azepin, benzothiophene, benzofuran, quinazoline, indazole, isobenzofuran, and pteridine, each optionally substituted by one or more groups selected from F, Cl, Br, CF$_3$, CHF$_2$, CH$_2$F, CN, OH, -methyl, ethyl, propyl, isopropyl, —O-methyl, O-ethyl, —COOmethyl, —COOethyl, SO$_2$—(CH$_3$), SO$_2$—(CH$_2$CH$_3$), phenyl, -methylene-phenyl, -ethylene-phenyl, —NH$_2$, —NH(CH$_3$), N(CH$_3$)$_2$, -methylene-NH$_2$, -methylene-NH(CH$_3$), -methylene-N(CH$_3$)$_2$, a C$_{3-6}$-cycloalkyl, a methylene-C$_{3-6}$-cycloalkyl, a het, a hetaryl, -methylene-hetaryl, and -methylene-het, each optionally substituted by one or more groups selected from OH, F, Cl, Br, CF$_3$, CHF$_2$, CH$_2$F, methyl, ethyl, propyl, isopropyl, phenyl, —COO(CH$_3$), —O-methyl, and —O-ethyl.

16. The medicament according to claim 1, wherein:
R$^1$ is H,
R$^2$ is a group selected from

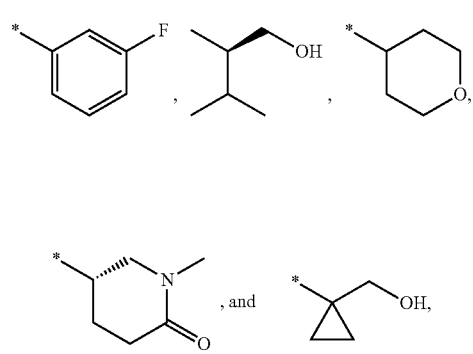

R$^3$ is a group selected from

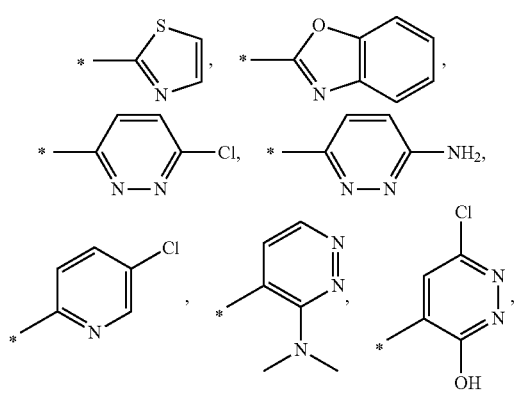

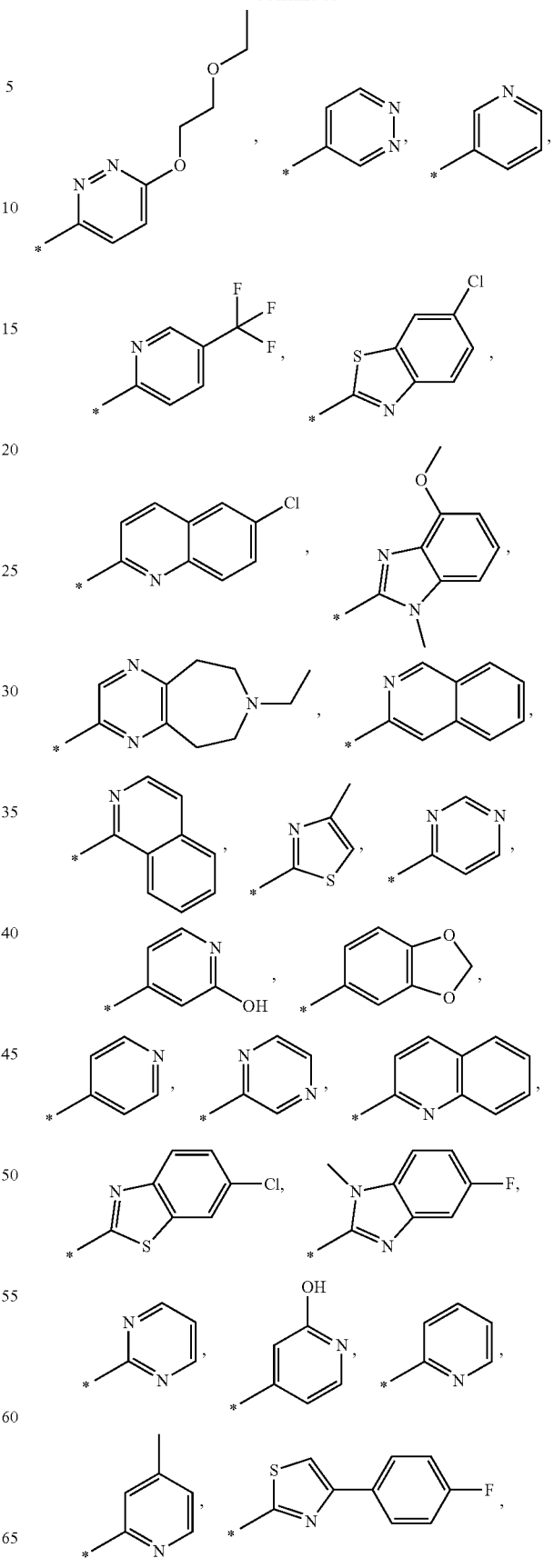

-continued

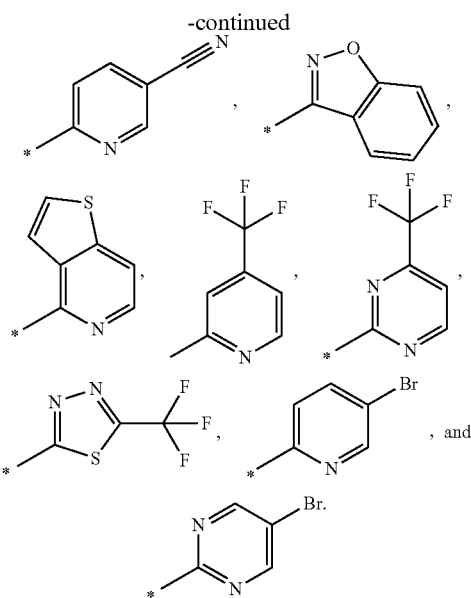

17. The medicament according to claim 1, wherein the PDE4 inhibitor of general formula 1 is selected from:

1.1 (3-fluorophenyl)-[5-oxo-2-(4-thiazol-2-yl-piperazin-1-yl)-6,7-dihydro-5H-5λ⁴-thieno[3,2-d]pyrimidin-4-yl]-amine;
1.2 (R)-3-methyl-2-[5-oxo-2-(4-thiazol-2-yl-piperazin-1-yl)-6,7-dihydro-5H-5λ⁴-thieno[3,2-d]pyrimidin-4-ylamino]-butan-1-ol;
1.3 [2-(4-benzoxazol-2-yl-piperazin-1-yl)-5-oxo-6,7-dihydro-5H-5λ⁴-thieno[3,2-d]pyrimidin-4-yl]-(3-fluorophenyl)-amine;
1.4 [2-(4-benzoxazol-2-yl-piperazin-1-yl)-5-oxo-6,7-dihydro-5H-5λ⁴-thieno[3,2-d]pyrimidin-4-yl]-(tetrahydropyran-4-yl)-amine;
1.5 (R)-2-{2-[4-(6-chloropyridazin-3-yl)-piperazin-1-yl]-5-oxo-6,7-dihydro-5H-5λ⁴-thieno[3,2-d]pyrimidin-4-ylamino}-3-methylbutan-1-ol;
1.6 {2-[4-(6-chloropyridazin-3-yl)-piperazin-1-yl]-5-oxo-6,7-dihydro-5H-5λ⁴-thieno[3,2-d]pyrimidin-4-yl}-(3-fluorophenyl)-amine;
1.7 (R)-2-[2-(4-benzoxazol-2-yl-piperazin-1-yl)-5-oxo-6,7-dihydro-5H-5λ⁴-thieno[3,2-d]pyrimidin-4-ylamino]-3-methylbutan-1-ol;
1.8 (1-{2-[4-(5-chloropyridin-2-yl)-piperazin-1-yl]-5-oxo-6,7-dihydro-5H-5λ⁴-thieno[3,2-d]pyrimidin-4-ylamino}-cyclopropyl)-methanol;
1.9 {2-[4-(5-chloropyridin-2-yl)-piperazin-1-yl]-5-oxo-6,7-dihydro-5H-5λ⁴-thieno[3,2-d]pyrimidin-4-yl}-(tetrahydropyran-4-yl)-amine;
1.10 {2-[4-(3-dimethylaminopyridazin-4-yl)-piperazin-1-yl]-5-oxo-6,7-dihydro-5H-5λ⁴-thieno[3,2-c]pyrimidin-4-yl}-(3-fluorophenyl)-amine;
1.11 6-chloro-4-{4-[4-(3-fluorophenylamino)-5-oxo-6,7-dihydro-5H-5λ⁴-thieno[3,2-d]pyrimidin-2-yl]-piperazin-1-yl}-pyridazin-3-ol;
1.12 2-{4-[6-(2-ethoxyethoxy)-pyridazin-3-yl]-piperazin-1-yl}-5-oxo-6,7-dihydro-5H-5λ⁴-thieno[3,2-d]pyrimidin-4-yl)-(3-fluorophenyl)-amine;
1.13 (3-fluorophenyl)-[5-oxo-2-(4-pyridazin-4-yl-piperazin-1-yl)-6,7-dihydro-5H-5λ⁴-thieno[3,2-d]pyrimidin-4-yl]-amine;
1.14 (R)-2-{2-[4-(4-methoxy-1-methyl-1H-benzimidazol-2-yl)-piperazin-1-yl]-5-oxo-6,7-dihydro-5H-5λ⁴-thieno[3,2-d]pyrimidin-4-ylamino}-3-methylbutan-1-ol;
1.15 (R)-2-{2-[4-(7-ethyl-6,7,8,9-tetrahydro-5H-pyrazino[2,3-d]azepin-2-yl)-piperazin-1-yl]-5-oxo-6,7-dihydro-5H-5λ⁴-thieno[3,2-d]pyrimidin-4-ylamino}-3-methylbutan-1-ol;
1.16 (R)-3-methyl-2-[5-oxo-2-(4-pyrimidin-4-yl-piperazin-1-yl)-6,7-dihydro-5H-5λ⁴-thieno[3,2-d]pyrimidin-4-ylamino]-butan-1-ol;
1.17 4-{4-[4-((R)-1-hydroxymethyl-2-methylpropylamino)-5-oxo-6,7-dihydro-5H-5λ⁴-thieno[3,2-d]pyrimidin-2-yl]-piperazin-1-yl}-pyridin-2-ol;
1.18 (R)-3-methyl-2-[5-oxo-2-(4-pyridin-4-yl-piperazin-1-yl)-6,7-dihydro-5H-5λ⁴-thieno[3,2-d]pyrimidin-4-ylamino]-butan-1-ol;
1.19 (R)-2-{2-[4-(3-dimethylaminopyridazin-4-yl)-piperazin-1-yl]-5-oxo-6,7-dihydro-5H-5λ⁴-thieno[3,2-d]pyrimidin-4-ylamino}-3-methylbutan-1-ol;
1.20 6-chloro-4-{4-[4-((R)-1-hydroxymethyl-2-methylpropylamino)-5-oxo-6,7-dihydro-5H-5λ⁴-thieno[3,2-d]pyrimidin-2-yl]-piperazin-1-yl}-pyridazin-3-ol;
1.21 (R)-2-(2-{4-[6-(2-ethoxyethoxy)-pyridazin-3-yl]-piperazin-1-yl}-5-oxo-6,7-dihydro-5H-5λ⁴-thieno[3,2-d]pyrimidin-4-ylamino)-3-methylbutan-1-ol;
1.22 (R)-3-methyl-2-[5-oxo-2-(4-pyridazin-4-yl-piperazin-1-yl)-6,7-dihydro-5H-5λ⁴-thieno[3,2-d]pyrimidin-4-ylamino]-butan-1-ol;
1.23 {1-[5-oxo-2-(4-pyrimidin-4-yl-piperazin-1-yl)-6,7-dihydro-5H-5λ⁴-thieno[3,2-d]pyrimidin-4-ylamino]-cyclopropyl}-methanol;
1.24 {1-[5-oxo-2-(4-pyridin-4-yl-piperazin-1-yl)-6,7-dihydro-5H-5λ⁴-thieno[3,2-d]pyrimidin-4-ylamino]-cyclopropyl}-methanol;
1.25 (S)-1-methyl-5-[5-oxo-2-(4-pyrimidin-4-yl-piperazin-1-yl)-6,7-dihydro-5H-5λ⁴-thieno[3,2-d]pyrimidin-4-ylamino]-piperidin-2-one;
1.26 {2-[4-(5-fluoro-1-methyl-1H-benzoimidazol-2-yl)-piperazin-1-yl]-5-oxo-6,7-dihydro-5H-5λ⁴-thieno[3,2-d]pyrimidin-4-yl}-(tetrahydropyran-4-yl)-amine;
1.27 [5-oxo-2-(4-pyridin-4-yl-piperazin-1-yl)-6,7-dihydro-5H-5λ⁴-thieno[3,2-d]pyrimidin-4-yl]-(tetrahydropyran-4-yl)-amine;
1.28 (3-fluorophenyl)-{2-[4-(4-methoxy-1-methyl-1H-benzimidazol-2-yl)-piperazin-1-yl]-5-oxo-6,7-dihydro-5H-5λ⁴-thieno[3,2-d]pyrimidin-4-yl}-amine;
1.29 {2-[4-(7-ethyl-6,7,8,9-tetrahydro-5H-pyrazino[2,3-d]azepin-2-yl)-piperazin-1-yl]-5-oxo-6,7-dihydro-5H-5λ⁴-thieno[3,2-d]pyrimidin-4-yl}-(3-fluorophenyl)-amine;
1.30 (3-fluorophenyl)-[5-oxo-2-(4-pyrimidin-4-yl-piperazin-1-yl)-6,7-dihydro-5H-5λ⁴-thieno[3,2-d]pyrimidin-4-yl]-amine;
1.31 4-{4-[4-(3-fluorophenylamino)-5-oxo-6,7-dihydro-5H-5λ⁴-thieno[3,2-d]pyrimidin-2-yl]-piperazin-1-yl}-pyridin-2-ol;
1.32 (3-fluorophenyl)-[5-oxo-2-(4-pyridin-4-yl-piperazin-1-yl)-6,7-dihydro-5H-5λ⁴-thieno[3,2-d]pyrimidin-4-yl]-amine;
1.33 (3-fluorophenyl)-(2-{4-[4-(4-fluorophenyl)-thiazol-2-yl]-piperazin-1-yl}-5-oxo-6,7-dihydro-5H-5λ⁴-thieno[3,2-d]pyrimidin-4-yl)-amine;
1.34 [2-(4-benzo[d]isoxazol-3-yl-piperazin-1-yl)-5-oxo-6,7-dihydro-5H-5λ⁴-thieno[3,2-d]pyrimidin-4-yl]-(3-fluorophenyl)-amine;

1.35 (R)-2-(2-{4-[4-(4-fluorophenyl)-thiazol-2-yl]-piperazin-1-yl}-5-oxo-6,7-dihydro-5H-5λ$^4$-thieno[3,2-d]pyrimidin-4-ylamino)-3-methylbutan-1-ol; and 1.36 (R)-2-[2-(4-benzo[d]isoxazol-3-yl-piperazin-1-yl)-5-oxo-6,7-dihydro-5H-5λ$^4$-thieno[3,2-d]pyrimidin-4-ylamino]-3-methylbutan-1-ol.

18. The medicament according to claim 1, wherein the PDE4 inhibitor is contained in a daily dose of 0.01 mg to 50 mg.

19. The medicament according to claim 1, wherein the EP4-receptor antagonist is used in a daily dose of 0.001 to 100 mg/kg body weight.

20. The medicament according to claim 1, wherein the EP4-receptor antagonist and the PDE4 inhibitor are used in a ratio by weight of 1:1 to 200:1.

* * * * *